United States Patent
Angibaud et al.

(10) Patent No.: US 7,173,040 B2
(45) Date of Patent: *Feb. 6, 2007

(54) FARNESYL TRANSFERASE INHIBITING 6-[(SUBSTITUTED PHENYL)METHYL]-QUINOLINE AND QUINAZOLINE DERINAZOLINE DERIVATIVES

(75) Inventors: Patrick René Angibaud, Fontaine-Bellenger (FR); Marc Gaston Venet, Le Mesnil-Esnard (FR); Ashis Kumar Saha, Harleysville, PA (US); Laurence Anne Mevellec, Louviers (FR)

(73) Assignee: Janssen Pharmaceutica N.V. (BE)

( * ) Notice: Subject to any disclaimer, the term of this patent is extended or adjusted under 35 U.S.C. 154(b) by 199 days.

This patent is subject to a terminal disclaimer.

(21) Appl. No.: 10/381,556

(22) PCT Filed: Sep. 18, 2001

(86) PCT No.: PCT/EP01/10895

§ 371 (c)(1), (2), (4) Date: Mar. 24, 2003

(87) PCT Pub. No.: WO02/24683

PCT Pub. Date: Mar. 28, 2002

(65) Prior Publication Data

US 2004/0048882 A1 Mar. 11, 2004

(30) Foreign Application Priority Data

Sep. 25, 2000 (EP) .................................. 00203366

(51) Int. Cl.
C07D 403/06 (2006.01)
A61K 31/47 (2006.01)
C07D 215/227 (2006.01)

(52) U.S. Cl. .................... 514/266.21; 514/266.23; 514/267; 544/252; 544/284

(58) Field of Classification Search ........... 544/252, 544/284; 514/266.21, 266.23, 267
See application file for complete search history.

(56) References Cited

U.S. PATENT DOCUMENTS 6,458,800 B1 * 10/2002 Angibaud et al. .......... 514/267
6,914,066 B2 * 7/2005 Angibaud et al. .......... 514/267

FOREIGN PATENT DOCUMENTS

| EP | 0371564 B1 | 6/1990 |
|---|---|---|
| WO | WO 97/16443 A2 | 5/1997 |
| WO | WO 97/21701 A1 | 6/1997 |
| WO | WO 98/40383 A1 | 9/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |

OTHER PUBLICATIONS

Simone, Oncology: Introduction, Cecil Textbook of Medicine, 20th Edition, vol. 1, pp. 1004-1010, 1996.*
Nielsen et al., Combination Therapy with the Farnesyl Protein Transferase Inhibitor SCH66336 and SCH58500 (p53 Adenovirus) in Preclinical Cancer Models, Cancer Research, 59, pp. 5896-5901, Dec. 1999.*
Tagawa, PubMed Abstract (Curr Pharm Des. 6(6):681-99) Apr. 2000.*
Kohl et al., "Selective Inhibition of ras-Dependent Transformation by a Farnesyltransferase Inhibitor." Science, 1993, pp. 1934-1937, vol. 260, No. 5116.
Rak et al., "Mutant ras Oncogenes Upregulate VEGF/VPF Expression: Implications for Induction and Inhibition of Tumor Angiogenesis." Cancer Research, 1995, pp. 4575-4580, vol. 55, No. 20.

* cited by examiner

*Primary Examiner*—Deepak Rao

(57) ABSTRACT

This invention comprises the compounds of formula (I):

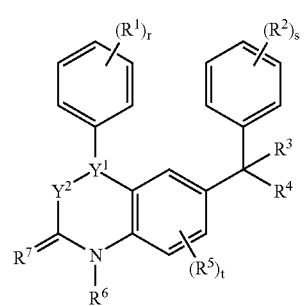

wherein r, s, t, $Y^1$–$Y^2$, $R^1$, $R^2$, $R^3$, $R^4$, $R^5$, $R^6$ and $R^7$ have defined meanings, having farnesyl transferase inhibiting activity; their preparation, compositions containing them and their use as a medicine.

8 Claims, No Drawings

FARNESYL TRANSFERASE INHIBITING 6-[(SUBSTITUTED PHENYL)METHYL]-QUINOLINE AND QUINAZOLINE DERINAZOLINE DERIVATIVES

CROSS REFERENCE TO RELATED APPLICATIONS

This application is the national stage of Application No. PCT/EP01/10895, filed Sep. 18, 2001 which application claims priority from EP 00203366.0 filed Sep. 25, 2000.

The present invention is concerned with novel 6-[(substituted phenyl)methyl]-quinoline and quinazoline derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499 and 00/47574.

Unexpectedly, it has been found that the present novel 6-[(substituted phenyl)methyl]-quinoline and quinazoline compounds show farnesyl protein transferase inhibiting activity.

The present invention concerns compounds of formula (I):

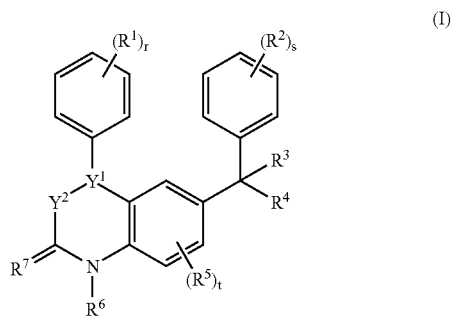

or a pharmaceutically acceptable salt or N-oxide or stereochemically isomeric form thereof, wherein
r and s are each independently 0, 1, 2, 3, 4 or 5;
t is 0, 1, 2 or 3;
$>Y^1—Y^2—$ is a trivalent radical of formula $>C=N—$          (y-1)

$>C=CR^9—$          (y-2)

$>CH—NR^9—$          (y-3)

$>CH—CHR^9—$          (y-4)

wherein $R^9$ is hydrogen, halo, cyano, $C_{1-6}$alkyl, hydroxy$C_{1-6}$alkyl, $C_{1-6}$alkyloxy$C_{1-6}$alkyl, $—(CR^{20}R^{21})_p—C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alkyloxycarbonyl, aryl or a group of formula $—NR^{22}R^{23}$, $—C_{1-6}$alkyl-$NR^{22}R^{23}$, $—C_{2-6}$alkenyl-$NR^{22}R^{23}$, $—CONR^{22}R^{23}$ or $—NR^{22}—C_{1-6}$alkyl-$NR^{22}R^{23}$;

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or $—(CR^{20}R^{21})_p—C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, OCF$_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;

$R^1$ is azido, hydroxy, halo, cyano, nitro, $C_{1-6}$alkyl, $—(CR^{20}R^{21})_p—C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}$S $C_{1-6}$alkyl, trihalomethyl, aryl$C_{1-6}$alkyl, Het$^2C_{1-6}$alkyl, $—C_{1-6}$alkyl-$NR^{22}R^{23}$, $—C_{1-6}$alkyl$NR^{22}C_{1-6}$alkyl-$NR^{22}R^{23}$, $—C_{1-6}$alkyl$NR^{22}COC_{1-6}$alkyl, $—C_{1-6}$alkyl$NR^{22}COAlkAr^2$, $—C_{1-6}$alkyl$NR^{22}COAr^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, $—OC_{1-6}$alkyl-$NR^{22}R^{23}$, trihalomethoxy, arylC$_{1-6}$alkyloxy, Het$^2$C$_{1-6}$alkyloxy, C$_{1-6}$alkylthio, C$_{2-6}$alkenyl, cyanoC$_{2-6}$alkenyl, —C$_{2-6}$alkenyl-NR$^{22}$R$^{23}$, hydroxycarbonylC$_{2-6}$alkenyl, C$_{1-6}$alkyloxycarbonylC$_{2-6}$ alkenyl, C$_{2-6}$alkynyl, —CHO, C$_{1-6}$alkylcarbonyl, hydroxyC$_{1-6}$alkylcarbonyl, hydroxycarbonyl, C$_{1-6}$aklkyoxycarbonyl, —CONR$^{22}$R$^{23}$, —CONR$^{22}$—C$_{1-6}$alkyl-NR$^{22}$R$^{23}$, —CONR$^{22}$—C$_{1-6}$ alkyl-Het$^2$, —CONR$^{22}$—C$_{1-6}$ alkyl-Ar$^2$, —CONR$^{22}$—Het$^2$, —CONR$^{22}$Ar$^2$, —CONR$^{22}$—O—C$_{1-6}$alkyl, —CONR$^{22}$—C$_{1-6}$alkenyl, —NR$^{22}$R$^{23}$, —OC(O)R$^{24}$, —CR$^{24}$=NR$^{25}$, —CR$^{24}$=N—OR$^{25}$, —NR$^{24}$C(O)NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, aryloxy, Het$^2$-oxy, or a group of formula -Z, —CO-Z or —CO—NR$^y$-Z in which R$^y$ is hydrogen or C$_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, —COOR$^{24}$, aminocarbonyl, C$_{1-6}$alkylthio, hydroxy, —NR$^{22}$R$^{23}$, C$_{1-6}$alkylsulphonylamino, C$_{1-6}$alkyl, haloC$_{1-6}$alkyl,C$_{1-6}$allyloxy or phenyl; or two R$^1$ substituents adjacent to one another on the phenyl ring may form together a bivalent radical of formula —O—CH$_2$—O— (a-1)

—O—CH$_2$—CH$_2$—O— (a-2)

—O—CH=CH— (a-3)

—O—CH$_2$—CH$_2$— (a4)

—O—CH$_2$—CH$_2$—CH$_2$— (a-5)

—CH=CH—CH=CH— (a-6)

R$^{24}$ and R$^{25}$ are independently hydrogen, C$_{1-6}$ alkyl, —(CR$_{20}$R$_{21}$)p—C$_{3-10}$cycloallcyl or arylC$_{1-6}$alkyl;

R$^{26}$, R$^{27}$ and R$^{28}$ are independently hydrogen and C$_{1-6}$alkyl or C(O)C$_{1-6}$alkyl;

R$^2$ is azido, nitro, —(CR$^{20}$R$^{21}$)$_p$—C$_{3-10}$cycloalkyl, cyanoC$_{1-6}$alkyl, mono- or di-haloC$_{1-6}$alkyl, hydroxyC$_{1-6}$alkyl, C$_{1-6}$alkyloxyC$_{1-6}$alkyl, hydroxycarbonylC$_{1-6}$alkyloxyC$_{1-6}$alkyl, R$^{24}$SC$_{1-6}$alkyl, Het$^2$C$_{1-6}$alkyl (in which the C$_{1-6}$alkyl moiety is optionally substituted by hydroxy), Het$^2$SC$_{1-6}$ alkyl), —C$_{1-6}$alkylNR$^{22}$-Het$^2$, —C$_{1-6}$alkylNR$^{22}$—C$_{1-6}$alkyloxyC$_{1-6}$alkyl, —C$_{1-6}$alkylNR$^{22}$—C$_{1-6}$alkyl-S—C$_{1-6}$alkyl-Ar$^2$, —C$_{1-6}$alkylNR$^{22}$—C$_{1-6}$alkyl-S—C$_{1-6}$alkyl, —C$_{1-6}$alkylNR$^{22}$—C$_{1-6}$alkyl (in which the terminal C$_{1-6}$ alkyl moiety is substituted by hydroxy), —C$_{1-6}$ alkylNR$^{22}$C$_{2-6}$alkenyl, —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{2-6}$alkyl-Ar$^2$ (in which the C$_{1-6}$alkyl moiety adjacent to the Ar$^2$ is optionally substituted by C$_{1-6}$alkyloxycarbonyl), —C$_{1-6}$alkylNR$^{22}$C$_{1-6}$alkyl-Het$^2$, —C$_{1-6}$alkylNR$^{22}$COC$_{1-6}$alkyl, —C$_{1-6}$alkylNR$^{22}$C$_{1-6}$alkylC(O)OC$_{1-6}$alkyl, —C$_{1-6}$-alkylNR$^{22}$COAlkAr$^2$, —C$_{1-6}$alkylNR$^{22}$COAr$^2$, C$_{1-6}$alkylsulphonylaminoC$_{1-6}$alkyl, Het$^2$C$_{1-6}$alkyloxy, cyanoC$_{2-6}$alkenyl, —C$_{2-6}$alkenyl-NR$^{22}$R$^{23}$, hydroxycarbonylC$_{2-6}$alkenyl, C$_{1-6}$alkyloxycarbonylC$_{2-6}$alkenyl, C$_{2-6}$alkynyl, —CHO, C$_{1-6}$alkylcarbonyl, hydroxyC$_{1-6}$alkylcarbonyl, —CONR$^{22}$—C$_{1-6}$alkyl-NR$^{22}$R$^{23}$, —CONR$^{22}$—C$_{1-6}$alky-Het$^2$, —CONR$^{22}$—C$_{1-6}$alkyl-Ar$^2$, —CONR$^{22}$—O—C$_{1-6}$alkyl, —CONR$^{22}$—C$_{1-6}$ alkenyl, —NR$^{22}$R$^{23}$, —OC(O)R$^{24}$, —CR$^{24}$=NR$^{25}$, —CR$^{24}$=N—OR$^{25}$, —NR$^{24}$C(O)NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, Het$^2$-oxy, or a group of formula -Z, —CO-Z or —CO—NR$^y$-Z in which R$^y$ is hydrogen or C$_{1-4}$alkyl and Z is phenyl or a mono- or bicyclic heterocyclic ring containing one or more heteroatoms selected from oxygen, sulphur and nitrogen, the phenyl or heterocyclic ring being optionally substituted by one or two substituents each independently selected from halo, cyano, —COOR$^{24}$, aminocarbonyl, C$_{1-6}$alkylthio, hydroxy, —NR$^{22}$R$^{23}$, C$_{1-6}$alkylsulphonylamino, C$_{1-6}$alkyl, haloC$_{1-6}$alkyl,C$_{1-6}$alkyloxy or phenyl; and, when R$^4$ below represents a group of formula (c-3) or (c4), then R$^2$ may additionally represent hydrogen, halo, cyano, C$_{1-6}$alkyl, C$_{1-6}$alkyloxy, Ar$^2$ oxy, trihalomethyl, C$_{1-6}$alkylthio, di(C$_{1-6}$alkyl)amino, or two R$^2$ substituents adjacent to one another on the phenyl ring may together form a bivalent radical of formula —O—CH$_2$—O— (a-1), —O—CH$_2$—CH$_2$—O— (a-2)

—O—CH$_2$—CH$_2$— (a-4)

—CH=CH—CH=H— (a-6) or

—CH$_2$—O—CH$_2$ (a-7)

and when R$^7$ below represents oxygen or sulphur, then R$^2$ may additionally represent hydroxy, arylC$_{1-6}$alkyl, —C$_{1-6}$alkyl-NR$^{22}$R$^{23}$, hydroxyC$_{1-6}$alkyloxy, C$_{1-6}$alkyloxyC$_{1-6}$alkyloxy, —OC$_{1-6}$alkyl-NR$^{22}$R$^{23}$, trihalomethoxy, arylC$_{1-6}$alkyloxy, C$_{2-6}$alkenyl, hydroxycarbonyl, C$_{1-6}$alkyloxycarbonyl, —CONR$^{22}$R$^{23}$, or two R$^2$ substituents adjacent to one another on the phenyl ring may form together a bivalent radical of formula —O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

R$^{24}$ and R$^{25}$ are independently hydrogen, C$_{1-6}$alkyl, —(CR$_{20}$R$_{21}$)p—C$_{3-10}$cycloalklyl or arylC$_{1-6}$alkyl;

—R$^{26}$, R$^{27}$ and R$^{28}$ are independently hydrogen and C$_{1-6}$alkyl or C(O)C$_{1-6}$alkyl R$^3$ is hydrogen, halo, cyano, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, arylC$_{1-6}$alkyloxyC$_{1-6}$alkyl, C$_{1-6}$alkylthioC$_{1-6}$alkyl, hydroxycarbonylC$_{1-6}$alkyl, C$_{1-6}$alkylcarbonylC$_{1-6}$alkyl, C$_{1-6}$alkyloxycarbonylC$_{1-6}$alkyl, —C$_{1-6}$alkyl-NR$^{22}$R$^{23}$, —C$_1$alkyl-CONR$^{22}$R$^{23}$, arylC$_{1-6}$alkyl, Het$^2$C$_{1-6}$alkyl, C$_{2-6}$alkenyl, —C$_{2-6}$alkenylNR$^{22}$R$^{23}$, C$_{2-6}$alkynyl, hydroxycarbonyl, C$_{1-6}$alkyloxycarbonyl, aryl, or Het$^2$; or a radical of formula —O—R$^{10}$ (b-1)

—S—R$^{10}$ (b-2)

—NR$^{11}$R$^{12}$ (b-3) or

—N=CR$^{10}$R$^{11}$ (b-4)

wherein $R^{10}$ is hydrogen, $C_{1-6}$alkyl, $-(CR^{20}R^{21})_p-C_{3-10}$cycloalkyl, aryl$C_{1-6}$alkyl, $C_{2-6}$alkenyl, $C_{2-6}$alkynyl, $C_{1-6}$alkylcarbonyl, aryl, a group of formula $-NR^{22}R^{23}R$ or $-C_{1-6}$alkylC(O)OC$_{1-6}$alkyl $NR^{22}R^{23}$, or a radical of formula -Alk-OR$^{13}$ or -Alk-NR$^{14}$R$^{15}$;

$R^{11}$ is hydrogen, $C_{1-6}$alkyl, $-(CR^{20}R^{21})_p-C_{3-10}$cycloalkyl, $C_{2-6}$alkenyl, $C_{2-6}$alkynyl, aryl or aryl$C_{1-6}$alkyl;

$R^{12}$ is hydrogen, hydroxy, $C_{1-6}$alkyl, $-(CR^{20}R^{21})_p-C_{3-10}$cycloalkyl, $C_{1-6}$alkylcarbonyl$C_{1-6}$alkyl, aryl$C_{1-6}$alkyl, $C_{2-6}$alkenyl, $C_{2-6}$alkynyl, aryl, $C_{1-6}$alkyloxy, a group of formula $-NR^{22}R^{23}$, $C_{1-6}$alkylcarbonylamino, $C_{1-6}$alkylcarbonyl, halo$C_{1-6}$alkylcarbonyl, aryl$C_{1-6}$alkylcarbonyl, Het$^2$C$_{1-6}$alkylcarbonyl, arylcarbonyl, $C_{1-6}$alkyloxycarbonyl, trihalo$C_{1-6}$alkyloxycarbonyl, $C_{1-6}$alkyloxy$C_{1-6}$alkylcarbonyl, aminocarbonyl, mono- or di($C_{1-6}$alkyl)aminocarbonyl wherein the alkyl moiety may optionally be substituted by one or more substituents independently selected from aryl and Cieallyloxycarbonyl substituents;

aminocarbonylcarbonyl, mono- or di($C_{1-6}$alkyl)amino$C_{1-6}$alkylcarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl, $-(CR^{20}R^{21})_p-C_{3-10}$cycloalkyl, $C_{2-6}$alkenyl, $C_{2-6}$alkynyl, $C_{1-6}$alkylcarbonyl, hydroxy$C_{1-6}$alkyl, aryl or aryl$C_{1-6}$alkyl;

$R^{14}$ is hydrogen, $C_{1-6}$alkyl, $-(COR^{20}R^{21})_p-C_{3-10}$cycloalkyl, $C_{2-6}$alkenyl, $C_{2-6}$alkynyl, aryl or aryl$C_{1-6}$alkyl;

$R^{15}$ is hydrogen, $C_{1-6}$alkyl, $-(CR^{20}R^{21})_p-C_{3-10}$cycloakyl, $C_{2-6}$alkenyl, $C_{2-6}$alkynyl, $C_{1-6}$alkylcarbonyl, aryl or aryl$C_{1-6}$alkyl;

$R^4$ is a radical of formula

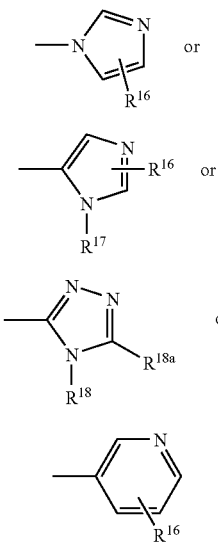

wherein $R^{16}$ is hydrogen, halo, cyano, $C_{1-6}$alkyl, $-(CR^{20}R^{21})_p-C_{3-10}$cycloalkyl, hydroxy$C_{1-6}$alkyl, $C_{1-6}$alkyloxy$C_{1-6}$alkyl, $C_{1-6}$alkylS(O)$_{0-2}$C$_{1-6}$alkyl, $C_{1-6}$alkyloxy, $C_{1-6}$alkylthio, a group of formula $-NR^{22}R^{23}$, hydroxycarbonyl, $C_{1-6}$alkyloxycarbonyl or aryl, $R^{17}$ is hydrogen, $C_{1-6}$alkyl, $-(CR^{20}R^{21})_p-C_{3-10}$cycloalkyl, hydroxy$C_{1-6}$alkyl, $C_{1-6}$alkyloxy$C_{1-6}$alkyl, aryl $C_{1-6}$alkyl, trifluoromethyl, trifluoromethyl$C_{1-6}$alkyl, hydroxycarbonyl$C_{1-6}$alkyl, $C_{1-6}$alkyloxycarbonyl$C_{1-6}$alkyl, mono- or di($C_{1-6}$alkyl)aminosulphonyl or $-C_{1-6}$alkyl P(O)OR$^{24}$OR$^{25}$;

$R^{18}$ is hydrogen, $C_{1-6}$alkyl, $-(CR^{20}R^{21})_p-C_{3-10}$cycloalkyl, aryl$C_{1-6}$alkyl or $C_{1-6}$alkyloxy$C_{1-6}$alkyl;

$R^{18a}$ is hydrogen, $-SH$ or $-S$ $C_{1-4}$alkyl $R^5$ is cyano, hydroxy, halo, $C_{1-6}$alkyl, $-(CR^{20}R^{21})_p-C_{3-10}$cycloalkyl, $C_{2-6}$alkenyl, $C_{2-6}$alkynyl, $C_{1-6}$alkyloxy, aryl$C_{1-6}$alkyloxy, Het$^2$C$_{1-6}$alkyloxy, hydroxycarbonyl, $C_{1-6}$alkyloxycarbonyl, or a group of formula $-NR^{22}R^{23}$ or $-CONR^{22}R^{23}$;

$R^6$ is hydrogen, $C_{1-6}$alkyl, $-(CR^{20}R^{21})_p-C_{3-10}$cycloalkyl, cyano$C_{1-6}$alkyl, $-C_{1-6}$alaylCO$_2$R$^{24}$, aminocarbonyl$C_{1-6}$alkyl or $-C_{1-6}$alkyl-NR$^{22}$R$^{23}$, $R^{24}$SO$_2$, $R^{24}$SO$_2$C$_{1-6}$alkyl, $-C_{1-6}$alkyl-OR$^{24}$, $-C_{1-6}$alkyl-SR$^{24}$, $-C_{1-6}$alkyl-CONR$^2$-C$_{1-6}$alkyl-NR$^{22}$R$^{23}$, $-C_{1-6}$alkylCONR$^{22}$-C$_{1-6}$alkyl-Het$^2$, $-C_{1-6}$alkylCONR$^{22}$-C$_{1-6}$alkyl-Ar$^2$, $-C_{1-6}$alkyl CONR$^{22}$-Het$^2$, $-C_{1-6}$alkylCONR$^{22}$Ar$^2$,$-C_{1-6}$alkyl CONR$^{22}$-O-C$_{1-6}$alkyl, $-C_{1-6}$alkyl-CONR$^{22}$-C$_{1-6}$alkenyl, -Alk-Ar$^2$ or -AlkHet$^2$;

$R^7$ is oxygen or sulphur; or $R^6$ and $R^7$ together form a trivalent radical of formula:

 (x-1)

 (x-2)

 (x-3)

 (x-4)

 (x-5)

 (x-6)

 (x-7)

 (x-8)

 (x-9) or

 (x-10)

wherein each $R^{30}$, $R^{31}$ and $R^{32}$ are independently hydrogen, $C_{1-6}$ alkyl, $-OR^{24}$, $-CHO$, $-COOR^{24}$, 13 NR$^{22}$R$^{23}$, $-C_{1-6}$ alkylOR$^{24}$, $-C_{1-6}$ alkylSR$^{24}$, $R^{23}R^{22}NC_{1-6}$alkyl-, $-CONR^{22}R^{23}$, $C_{2-6}$alkenyl, $C_{2-6}$alkenylAr$^2$, $C_{2-6}$alkenylHet$^2$, cyano, amino, thio, $C_{1-6}$ alkylthio, $-O-Ar^2$, $-S-Ar^2$, Het$^2$ or $C_{1-6}$alkylHet$^2$ Ar$^2$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkylNR$^{22}$R$^{23}$, $C_{1-6}$alkyloxy, OCF$_3$, hydroxycarbonyl, $C_{1-6}$alkyloxycarbonyi, aryloxy, $-NR^{22}R^{23}$, $C_{1-6}$alkylsulfonylamino, oxime or phenyl, or a bivalent substituent of formula $-O-CH_2-O-$ or $-O-CH_2-CH_2-O-$;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkylNR$^{22}$R$^{23}$, $C_{1-6}$alkyloxy, OCF$_3$, hydroxycarbonyl, $C_{1-6}$alkyloxycarbonyl, $-CONR^{22}R^{23}$, $-NR^{22}R^{23}$, $C_{1-6}$alkylsulfonylamino, oxime or phenyl;

provided that when $R^1$ is a group of formula —$CR^{24}$=$NOR^{25}$, —$S(O)_{0-2}R^{24}$, or $C_{2-6}$alkynyl and/or $R^3$ is a triazolyl group optionally substituted as defined for $Het^2$ and/or $R^6$ is —$(CR^{20}R^{21})_p$—$C_{3-10}$cycloalkyl, then >$Y^1$—$Y^2$— is a trivalent radical of formula (y-1) or (y-3) and/or $R^6$ and $R^7$ together form a trivalent radical selected from formulae (x-1) to (x-10).

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkaediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example tifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, $C_{1-6}$alkyl, $C_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

In the following discussion of preferred compounds according to the invention it will be appreciated that the provisos recited above in relation to formula (I) will still apply.

Examples of compounds of formula (I) include those wherein one or more of the following restrictions apply:

r and s are each independently 0, 1 or 2;

t is 0 or 1;

>$Y^1$—$Y^2$— is a trivalent radical of formula $$>C=N-\quad\quad\quad\quad (y\text{-}1)\text{ or}$$

$$>C=CR^9-\quad\quad\quad\quad (y\text{-}2)$$

wherein $R^9$ is hydrogen, cyano, halo, $C_{1-6}$alkyl, hydroxy$C_{1-6}$alkyl, hydroxycarbonyl or aminocarbonyl;

$R^1$ is halo, $C_{1-6}$alkyl, —$(CR^{20}R^{21})_p$—$C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$allkylthio, hydroxycarbonyl, $C_{1-6}$alkyloxycarbonyl, —$CONR^{22}R^{23}$, or —CH=$NOR^{25}$; or two $R^1$ substituents adjacent to one another on the phenyl ring may independently form together a bivalent radical of formula $$-O-CH_2-O-\quad\quad\quad\quad (a\text{-}1)$$

$$-O-CH_2-CH_2-O-\quad\quad\quad\quad (a\text{-}2)$$

$R^2$ is nitro, cyano, halo, $C_{1-6}$alkyl, cyano$C_{1-6}$alkyl, hydroxy$C_{1-6}$alkyl, $C_{1-6}$alkyloxy$C_{1-6}$alkyl, $Het^2C_{1-6}$alkyl (in which the $C_{1-6}$alkyl moiety is optionally substituted by hydroxy), $Het^2SC_{1-6}$alkyl, —$C_{1-6}$alkylNR$^{22}$-$Het^2$, —$C_{1-6}$alkylNR$^{22}$—$C_{1-6}$alkloxy$C_{1-6}$alkyl, —$C_{1-6}$alkylNR$^{22}$—$C_{1-6}$alkyl-S—$C_{1-6}$alkyl-Ar$^2$, —$C_{1-6}$alkylNR$^{22}$—$C_{1-6}$alkyl (in which the terminal $C_{1-6}$ alkyl moiety is substituted by hydroxy), —$C_{1-6}$alkylNR$^{22}$$C_{2-6}$ alkynyl, —$C_{1-6}$alkylNR$^{22}$$C_{1-6}$alkyl-NR$^{22}$R$^{23}$, —$C_{1-6}$alkylNR$^{22}$$C_{1-6}$alkyl-Ar$^2$ (in which the $C_{1-6}$alkyl moiety adjacent to the Ar$^2$ is optionally substituted by $C_{1-6}$alkyloxycarbonyl), —$C_{1-6}$alkylNR$^{22}$$C_{1-6}$alkyl-Het$^2$, —$C_{1-6}$alkylNR$^{22}$$C_{1-6}$alkylC(O)O$C_{1-6}$alkyl, —CHO, hydroxycarbonyl, $C_{1-6}$alkyloxycarbonyl, —$CONR^{22}R^{23}$, —$CONR^{22}$—$C_{1-6}$alkyl-Het$^2$, —$CONR^{22}$—$C_{1-6}$alkyl-Ar$^2$, —$CONR^{22}$—O—$C_{1-6}$alkyl, —$CONR^{22}$—$C_{1-6}$alkenyl, —$CR^{24}$=N—OR$^{25}$, or a group of formula -Z, —CO-Z or —CO—NR$^y$-Z $R^3$ is hydrogen, $C_{1-6}$alkyl, —$(CR^{20}R^{21})_p$—$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, —$C_{1-6}$alkyl NR$^{22}$R$^{23}$, Het$^2C_{1-6}$alkyl, —$C_{2-6}$alkenyl NR$^{22}$R$^{23}$, or -Het$^2$; or a group of formula $$-O-R^{10}\quad\quad\quad\quad (b\text{-}1)$$

$$-NR^{11}R^{12}\quad\quad\quad\quad (b\text{-}3)$$

wherein $R^{10}$ is hydrogen, $C_{1-6}$alkyl, or —$(CR^{20}R^{21})_p$—$C_{3-10}$cycloalkyl, or a group of formula -Alk-OR$^{13}$ or -Alk-NR$^{14}$R$^{15}$;

$R^{11}$ is hydrogen or $C_{1-6}$alkyl;

$R^{12}$ is hydrogen, hydroxy, $C_{1-6}$alkyl, —$(CR^{20}R^{21})_p$—$C_{3-10}$ cycloalkyl, $C_{1-6}$alkyloxy, $C_{1-6}$alkylcarbonyl, arylC$_{1-6}$alkylcarbonyl, Het$^2$C$_{1-6}$alkylcarbonyl, aminocarbonyl, or a radical of formula -Alk-OR$^{13}$ or Alk-NR$^{14}$R$^{15}$;
wherein Alk is C$_{1-6}$alkanediyl;
R$^{13}$ is hydrogen, C$_{1-6}$alkyl or —(CR$^{20}$R$^{21}$)$_p$—C$_{3-10}$cycloalkyl;
R$^{14}$ is hydrogen, C$_{1-6}$alkyl, or —(CR$^{20}$R$^{21}$)$_p$—C$_{3-10}$cycloalkyl;
R$^{15}$ is hydrogen or C$_{1-6}$alkyl;
R$^4$ is a radical of formula (c-2) or (c-3) wherein R$^{16}$ is hydrogen, halo or C$_{1-6}$alkyl,
R$^{17}$ is hydrogen, C$_{1-6}$alkyl, —(CR$^{20}$R$^{21}$)$_p$—C$_{3-10}$cycloalkyl,
C$_{1-6}$alkyloxyC$_{1-6}$alkyl or trifluoromethyl;
R$^{18}$ is hydrogen, C$_{1-6}$alkyl or —(CR$^{20}$R$^{21}$)$_p$—C$_{3-10}$cycloalkyl;
R$^{18a}$ is hydrogen;
R$^5$ is cyano, halo, C$_{1-6}$alkyl, C$_{2-6}$alkynyl, C$_{1-6}$alkyloxy or C$_{1-6}$alkyloxycarbonyl;
R$^6$ is hydrogen, C$_{1-6}$alkyl, —C$_{1-6}$alkylCO$_2$R$^{24}$, —C$_{1-6}$alkyl-C(O)NR$^{22}$R$^{23}$, -Alk-Ar$^2$, -AlkHet$^2$ or —(CR$^{20}$R$^{21}$)$_p$—C$_{3-10}$cycloalkyl,
R$^7$ is oxygen; or R$^6$ and R$^7$ together form a trivalent radical of formula (x-1), (x-2), (x-3), (x4) or (x-9)
Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:
>Y$^1$—Y$^2$— is a trivalent radical of formula (y-1) or (y-2), wherein R$^9$ is hydrogen, halo, C$_{1-4}$alkyl, hydroxycarbonyl, or C$_{1-4}$alkyloxycarbonyl;
r is 0, 1 or 2;
s is 0 or 1;
t is 0;
R$^1$ is halo, C$_{1-6}$alkyl, C$_{2-6}$alkenyl, C$_{2-6}$alkynyl or two R$^1$ substituents ortho to one another on the phenyl ring may independently form together a bivalent radical of formula (a-1);
R$^2$ is nitro, cyano, halo, C$_{1-6}$alkyl, cyanoC$_{1-6}$alkyl, hydroxyC$_{1-6}$alkyl, C$_{1-6}$alkyloxyC$_{1-6}$alkyl, Het$^2$C$_{1-6}$alkyl (in which the C$_{1-6}$alkyl moiety is optionally substituted by hydroxy), Het$^2$SC$_{1-6}$ alkyl, —C$_{1-6}$alkyl$^{22}$-Het$^2$, —C$_{1-6}$alkylNR$^{22}$—C$_{1-6}$alkyloxyC$_{1-6}$alkyl, —C$_{1-6}$alkylNR$^{22}$—C$_{1-6}$alkyl-S—C$_{1-6}$alkyl-Ar$^2$, —alkylNR$^{22}$—C$_{1-6}$alkyl (in which the terminal C$_{1-6}$ alkyl moiety is substituted by hydroxy), —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$^{1-6}$alkylNR$^{22}$C$_{1-6}$alkyl-Ar$^2$ (in which the C$_{1-6}$alkyl moiety adjacent to the Ar$^2$ is optionally substituted by C$_{1-6}$alkyloxycarbonyl), —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl, —CHO, hydroxycarbonyl, C$_{1-6}$alkyloxycarbonyl, —CONR$^{22}$R$^{23}$, —CONR$^{22}$—C$_{1-6}$alkyl-Het$^2$, —CONR$^{22}$—C$_{1-6}$alkyl-Ar$^2$, —CONR$^{22}$—O—C$_{1-6}$alkyl, —CONR$^{22}$—C$_{1-6}$alkenyl, —CR$^{24}$=N—OR$^{25}$, or a group of formula -Z, —CO-Z or —CO—NR$^y$-Z and in which the above Het$^2$ groups are independently selected from 5- or 6-membered monocyclic heterocyclic rings R$^3$ is Het$^2$ or a group of formula (b-1) or (b-3) wherein
R$^{10}$ is hydrogen or a group of formula -Alk-OR$^{13}$.
R$^{11}$ is hydrogen;
R$^{12}$ is hydrogen, C$_{1-6}$alkyl, C$_{1-6}$alkylcarbonyl, hydroxy, C$_{1-6}$alkyloxy or mono- or di(C$_{1-6}$alkyl)aminoC$_{1-6}$alkylcarbonyl;
Alk is C$_{1-6}$alkanediyl and R$^{13}$ is hydrogen;
R$^4$ is a group of formula (c-2) or (c-3) wherein
R$^{16}$ is hydrogen, halo or mono- or di(C$_{1-4}$alkyl)amino;
R$^{17}$ is hydrogen or C$_{1-6}$alkyl;
R$^{18}$ is hydrogen or C$_{1-6}$alkyl;
R$^{18a}$ is hydrogen;
R$^6$ is —(CR$^{20}$R$^{21}$)$_p$—C$_{3-10}$cycloalkyl, —C$_{1-6}$alkylCO$_2$R$^{24}$, aminocarbonylC$_{1-6}$alkyl, -Alk-Ar$^2$ or -AlkHet$^2$ or C$_{1-6}$alkyl;
R$^7$ is oxygen; or R$^6$ and R$^7$ together form a trivalent radical of formula (x-1), (x-2), (x-3), (x-4) or (x-9)
aryl is phenyl.

A particular group of compounds consists of those compounds of formula (I) wherein >Y$^1$—Y$^2$ is a trivalent radical of formula (y-2) or (y-1), r is 0 or 1, s is 1, t is 0, R$^1$ is halo, C$_{(1-4)}$alkyl or forms a bivalent radical of formula (a-1), R$^2$ is nitro, cyano, halo, C$_{1-6}$alkyl, cyanoC$_{1-6}$alkyl, C$_{1-6}$alkyloxyC$_{1-6}$alkyl, Het$^2$C$_{1-6}$alkyl (in which the C$_{1-6}$alkyl moiety is optionally substituted by hydroxy), Het$^2$SC$_{1-6}$ alkyl, —C$_{1-6}$ alkylNR$^{22}$—C$_{1-6}$alkyl-S—C$_{1-6}$alkyl, —C$_{1-6}$alkylNR$^{22}$C$_{2-6}$alkynyl, —C$_{1-6}$alkylNR$^{22}$C$_{1-6}$alkyl-Ar$^2$, —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl, —CHO, CH$_2$OH or —CR$^{24}$=N—OR$^{25}$ in which R$^{24}$ is hydrogen and R$^{25}$ is hydrogen or a methyl group; R$^3$ is hydrogen or a radical of formula (b-1) or (b-3), R$^{10}$ is hydrogen or -Alk-OR$^{13}$, R$^{11}$ is hydrogen and R$^{12}$ is hydrogen or C$_{1-6}$alkylcarbonyl and R$^{13}$ is hydrogen; R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen;
R$^6$ is C$_{1-6}$alkyl, —CH$_2$ —C$_{3-10}$cycloalkyl, —C$^{1-6}$alkylCO$_2$R$^{24}$ (R$^{24}$=H,Et), aminocarbonylC$_{1-6}$alkyl, -Alk-Ar or-AlkHet$^2$;
R$^7$ is oxygen; or R$^6$ and R$^7$ together form a trivalent radical of formula (x-2), (x-3), or (x4).

More preferred compounds are those compounds of formula (I) wherein >Y$^1$—Y$^2$ is a trivalent radical of formula (y-1) or (y-2), r is 0 or 1, s is 1, t is 0, R$^1$ is halo, preferably chloro and most preferably 3-chloro, R$^2$ is nitro, cyano, halo, preferably chloro and most preferably 4-chloro, C$_{1-6}$alkyl, preferably methyl and most preferably 4-methyl, cyanoC$_{1-6}$alkyl, C$_{1-6}$alkyloxyC$_{1-6}$alkyl, Het$^2$C$_{1-6}$alkyl (in which the C$_{1-6}$alkyl moiety is optionally substituted by hydroxy), Het$^2$SC$_{1-6}$ alkyl, —C$_{1-6}$alkylNR$^{22}$—C$_{1-6}$alkyl-S—C$_{1-6}$alkyl, —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{1-6}$alkyl-Ar$^2$, —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl,
—CHO, CH$_2$OH or —CR$^{24}$=N—OR$^{25}$ in which R$^{24}$ is hydrogen and R$^{25}$ is hydrogen or a methyl group; R$^3$ is hydrogen or a radical of formula (b-1) or (b-3), R$^9$ is hydrogen, R$^{10}$ is hydrogen, R$^{11}$ is hydrogen and R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen;
R$^6$ is C$_{1-6}$alkyl, —CH$_2$—C$_{3-10}$cycloalkyl or —C$_{1-6}$alkylAr$^2$;
R$^7$ is oxygen; or R$^6$ and R$^7$ together form a trivalent radical of formula (x-2) or (x-4).

Especially preferred compounds are those compounds of formula (I) wherein $>Y^1-Y^2$ is a trivalent radical of formula (y-1) or y-2, r and s are 1, t is 0, $R^1$ is halo, preferably chloro, and most preferably 3-chloro or $R^1$ is $C_{1-4}$alkyl, preferably 3-methyl, $R^2$ is nitro, cyano, halo, preferably chloro and most preferably 4-chloro, $C_{1-6}$alkyl, preferably methyl and most preferably 4-methyl, cyano$C_{1-6}$alkyl, $C_{1-6}$alkyloxy$C_{1-6}$alkyl, $Het^2C_{1-6}$alkyl in which $Het^2$ is 1-tetrazolyl, $Het^2SC_{1-6}$ alkyl in which $Het^2$ is 2-thiazolyl, $-C_{1-6}$alkyl$NR^{22}-C_{1-6}$alkyl-S-$C_{1-6}$alkyl, $-C_{1-6}$alkyl$NR^{22}C_{2-6}$ alkynyl, $-C_{1-6}$alkyl$NR^{22}C_{1-6}$alkyl-$NR^{22}R^{23}$, $-C_{1-6}$alkyl$NR^{22}C_{1-6}$alkyl-$Ar^2$, $-C_{1-6}$alkyl$NR^{22}C_{1-6}$alkyl-$Het^2$, $-C_{1-6}$alkyl$NR^{22}C_{1-6}$alkylC(O)OC_{1-6}$alkyl, $-CHO$, $CH_2OH$ or $-CR^{24}=N-OR^{25}$ in which $R^{24}$ is hydrogen and $R^{25}$ is hydrogen or a methyl group; $R^3$ is a radical of formula (b-1) or (b-3), $R^9$ is hydrogen, $R^{10}$ and $R^{11}$ are hydrogen and $R^{12}$ is hydrogen or hydroxy, $R^4$ is a radical of formula (c-2) or (c-3), wherein $R^{16}$ is hydrogen, $R^{17}$ is $C_{1-6}$alkyl preferably methyl, $R^{18}$ is $C_{1-6}$alkyl preferably methyl, $R^{18a}$ is hydrogen;

$R^6$ is $C_{1-6}$alkyl, $-CH_2-C_{3-10}$cycloalkyl or -alkyl$Ar^2$; $R^7$ is oxygen; or $R^6$ and $R^7$ together form a trivalent radical of formula (x-4).

The most preferred compounds according to the invention are:
(±)-4-[[4-(3-chlorophenyl)-1,2-dihydro-2-oxo-6-quinolinyl]hydroxy(1-methyl-1H-imidazol-5-yl)methyl]benzaldehyde
4-[[4-(3-chlorophenyl)-1,2-dihydro-2-oxo-6-quinolinyl]hydroxy(1-methyl-1H-imidazol-5-yl)methyl]benzaldehyde oxime
(±)-4-(3-chlorophenyl)-6-[hydroxy(1-methyl-1H-imidazol-5-yl)(4-nitrophenyl)methyl]-1-methyl-2(1H)-quinolinone
(±)-4-[[4-(3-chlorophenyl)-1,2-dihydro-1-methyl-2-oxo-6-quinolinyl]hydroxy(1-methyl-1H-imidazol-5-yl)methyl]benzaldehyde
(±)-4-[[4-(3-chlorophenyl)-1,2-dihydro-1-methyl-2-oxo-6-quinolinyl]hydroxy(1-methyl-1H-imidazol-5-yl)methyl]benzaldehyde O-methyloxime
(±)-6-[amino(1-methyl-1H-imidazol-5-yl)(4-nitrophenyl)methyl]-4-(3-chlorophenyl)-1-methyl-2(1H)-quinolinone
(±)-4-(3-chlorophenyl)-6-[hydroxy[4-(hydroxymethyl)phenyl](1-methyl-1H-imidazol-5-yl)methyl]-1-methyl-2(1H) quinolinone
N-[[4-[[(3-chlorophenyl)-1,2-dihydro-1-methyl-2-oxo-6-quinolinyl]hydroxy(1-methyl-1H-imidazol-5-yl)methyl] phenyl]methyl]-phenylalanine methyl ester
4-(3-chlorophenyl)-6-[(4-chlorophenyl)(4-methyl-4H-1,2,4-triazol-3-yl)methyl]-1-methyl-2(1H)-quinolinone
4-(3-chlorophenyl)-6-[hydroxy(1-methyl-1H-imidazol-5-yl)[4-(1H-tetrazol-1-ylmethyl)phenyl]methyl]-1-methyl-2(1H)-quinolinone
4-(3-chlorophenyl)-6-[[4-(ethoxymethyl)phenyl]hydroxy(1-methyl-1H-imidazol-5-yl)methyl]-1-methyl-2(1H)-quinolinone
4-(3-chlorophenyl)-6-[hydroxy(1-methyl-1H-imidazol-5-yl)[4-[(2-thiazolylthio)methyl]phenyl]methyl]-1-methyl-2(1H)-quinolinone
4-[[5-(3-chlorophenyl)tetrazolo[1,5-a]quinazolin-7-yl](4-methyl-4H-1,2,4-triazol-3-yl)methyl]-benzonitrile
5-(3-chlorophenyl)-α-(4-chlorophenyl)-α-(4-methyl-4H-1,2,4-triazol-3-yl)-tetrazolo[1,5-a]quinazoline-7-methanamine
4-[amino[5-(3-chlorophenyl)tetrazolo[1,5-a]quinazolin-7-yl](4methyl-4H-1,2,4-triazol-3-yl)methyl]-benzonitrile
4-(3-chlorophenyl)-6-[1-(4-chlorophenyl)-1-(4-methyl-4H-1,2,4-triazol-3-yl)methyl]-1-methyl-2(1H)-quinolinone
4-[[5-(3-chlorophenyl)tetrazolo[1,5-a]quinazolin-7-yl]hydroxy(1-methyl-1H-imidazol-5-yl)methyl]-benzeneacetonitrile and their pharmaceutically acceptable salts.

The compounds of formula (I) and their pharmaceutically acceptable salts and N-oxides and stereochemically isomeric forms thereof may be prepared in conventional manner, for example by a process which comprises:
a) cyclising a compound of formula (II):

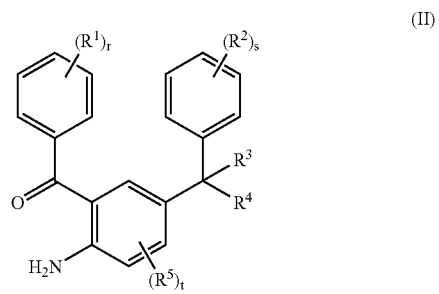

with a reagent serving to form a compound of formula (I) in which $R^6$ is hydrogen and $R^7$ is oxygen;
b) reacting a compound of formula (II):

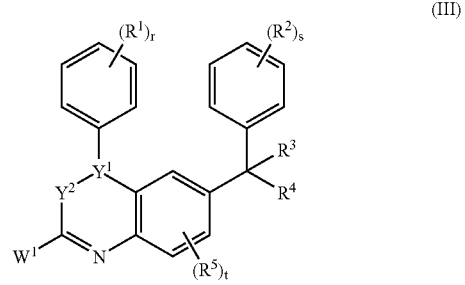

in which $W^1$ represents a replaceable or reactive group, with a reagent serving either to react with or replace the $W^1$ group in compound (III) to form a compound of formula (I) in which $R^6$ is hydrogen and $R^7$ is an oxygen or sulphur group or to react with the $W^1$ group and the adjacent nitrogen atom to form directly or indirectly a compound of formula (I) in which $R^6$ and $R^7$ together form a trivalent radical selected from formulae (x-1) to (x-10); or
c) reacting a compound of formula (IV):

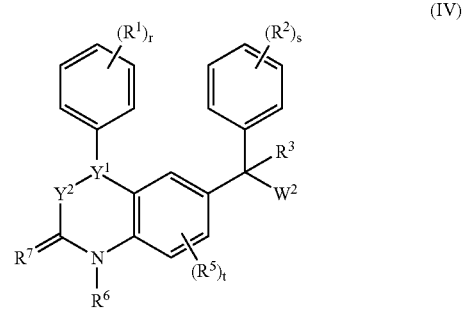

in which W² is a replaceable group, with an imidazole reagent serving to replace the group W² with an R⁴group of formula (c-1); or d) reacting a compound of formula (V):

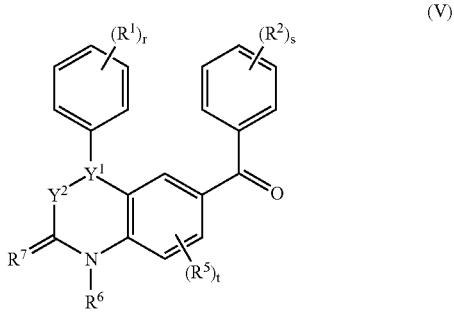

with an imidazole reagent to form a compound of formula (I) in which R⁴ is a group of formula (c-2), or with a 3-mercapto-4-methyl-1,2,4-triazole reagent to form a compound of formula (I) in which R⁴ is a group of formula (c-3), or with a 3-bromopyridyl group to form a compound of formula (I) wherein R⁴ is a group of formula (c-4) or;

e) reacting a compound of formula (VI):

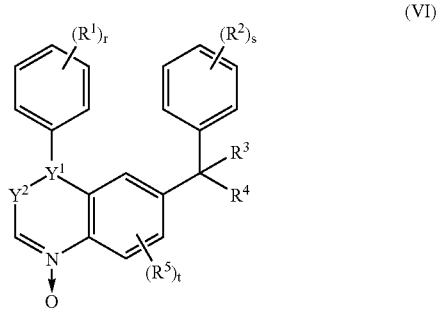

with a reagent serving to convert the said compound (VI) to a compound of formula (I) in which R⁶ is hydrogen and R⁷ is oxygen; and optionally effecting one or more of the following conversions in any desired order:

(i) converting a compound of formula (I) into a different compound of formula (I);

(ii) converting a compound of formula (I) in to a pharmaceutically acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

With regard to process a), this can be effected as described for example in WO 97/21701 and WO98/49157 referred to above. Thus, the cyclisation may be effected for example by subjecting the compound of formula (I) to an acetylation reaction, e.g. by treatment with the anhydride of a carboxylic acid, e.g. acetic anhydride in a reaction-inert solvent, e.g. toluene, and subsequent reaction with a base such as potassium tert-butoxide in a reaction-inert solvent such as 1,2-dimethoxyethane.

With regard to process b), this can also be effected as described for example in WO 97/21701 and WO98/49157 referred to above for the preparation of compounds in which R⁷ is oxygen, for example by hydrolysis of an ether of formula (II) in which W1 is $C_{1-6}$alkyloxy in an aqueous acid solution such hydrochloric acid. Alternatively a compound of formula (III) in which W¹ is a chloro radical can be used.

With regard to process b), for the preparation of compounds in which R⁶ and R⁷ together form a trivalent radical of formula (x-1) to (x-10), this can be effected as described for example in WO 00/39082 referred to above. For example, when W¹ is chloro, the compound of formula (III) can be reacted with an azide compound for example sodium azide to form a corresponding compound of formula (I) in which R⁶ and R⁷ together form a trivalent radical of formula (x-4). Alternatively, when W¹ is chloro, the compound of formula (III) can be reacted with aquous hydrazine to form a compound of formula (III) where W¹ is NHNH₂ which by reaction with sodium nitrite in acidic media form a corresponding compound of formula (I) in which R⁶ and R⁷ together form a trivalent radical of formula (x-4).

With regard to process c), this can be effected for example by N-alkylating an intermediate of formula (IV), wherein W² is an appropriate leaving group such as, for example, chloro, bromo, methanesulfonyloxy or benzenesulfonyloxy, with an intermediate of formula (IVa) to form a a compound of formula (I) in which R⁴ is a group of formula (c-1) represented by compounds of formula (I-a):

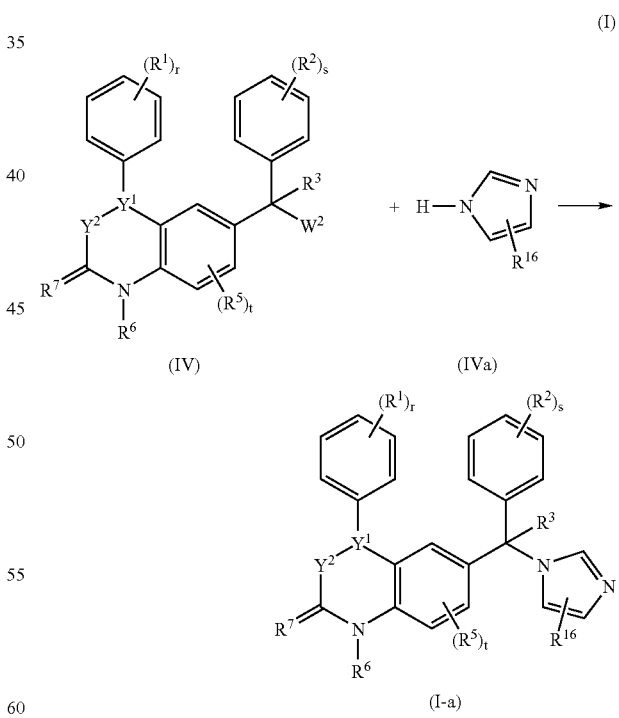

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (V) in which $W^2$ is hydroxy with an intermediate of formula (X), wherein Y is oxygen or sulfur, such as, for example, a 1,1'-carbonyldiimidazole.

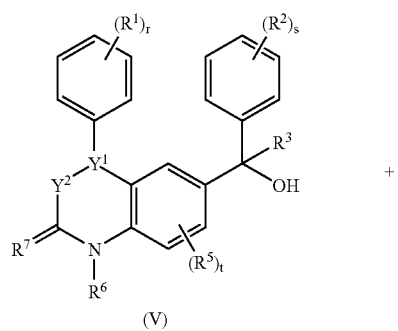

(V)

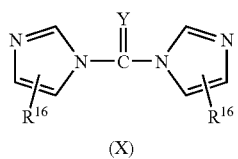

(X)

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

With regard to process d), this can be used to introduce the $R^4$ group, for example by reacting a compound of formula (V) in which $R^x$ is $R^2$ with an imidazole reagent to form a compound of formula (I) in which $R^4$ is a group of formula (c-2), or with a 3-mercapto-4$C_{1-6}$alkyl-1,2,4triazole reagent to form the corresponding 3-mercapto4-$C_{1-6}$alkyl-1,2,4triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group; or with a 3-bromopyridyl group to form a compound of formula (I) in which $R^4$ is a group of formula (c-4). In more detail, the compounds of formula (I) wherein $R^4$ represents a radical of formula (c-2), $R^3$ is hydroxy and $R^{17}$ is $C_{1-6}$alkyl, said compounds being referred to as compounds of formula (I-b-1) may be prepared by reacting an intermediate ketone of formula (V) with an intermediate of formula (III-1). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed.

Other procedures with protective groups analogous to silane derivatives can also be applied.

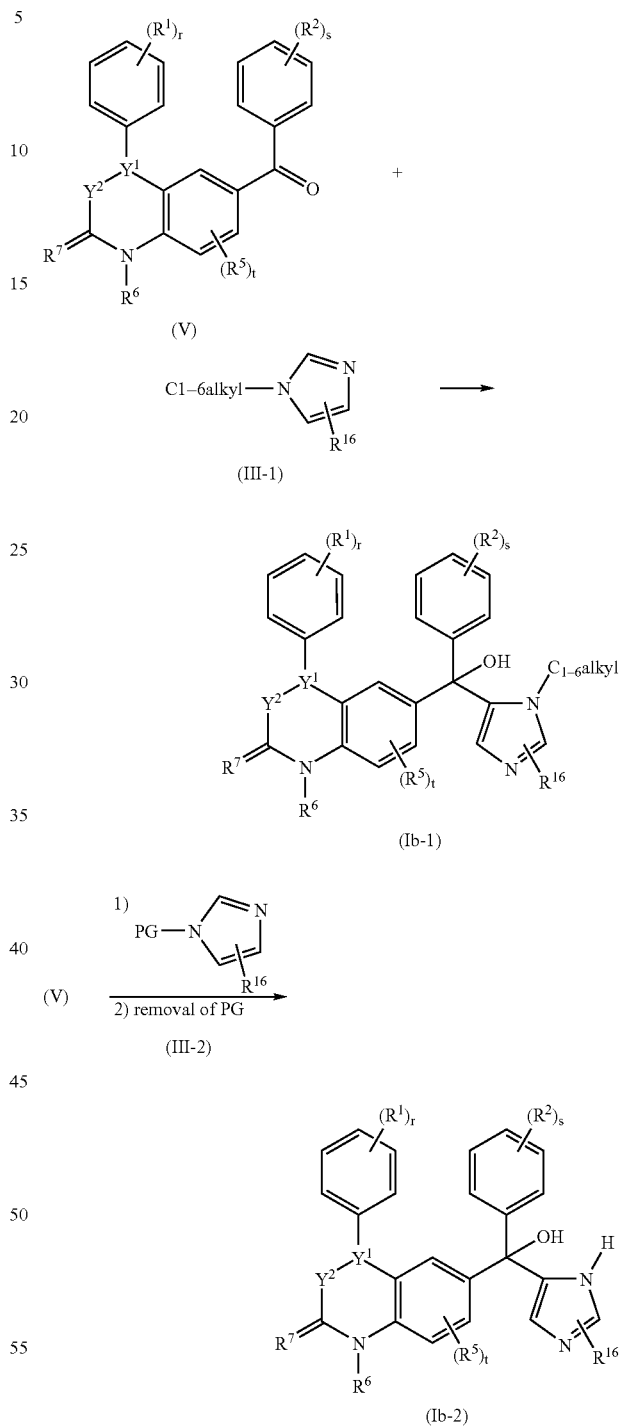

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (V) with a intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2).

With regard to process e), this may be effected for example as described in WO 97/21701 referred to above, by reacting the nitrone of formula (VI) with the anhydride of a carboxylic acid, e.g. acetic anhydride, thus forming the corresponding ester on the 2-position of the quinoline moiety, which ester can then be hydrolysed in situ to the corresponding quinolinone using a base such potassium carbonate. Alternatively the above nitrone can be reacted with tosyl chloride to prepare the corresponding tosylate which can then be hydrolysed in situ.

Examples of the interconversion of one compound of formula (I) into a different compound of formula (I) include the following reactions:

a) compounds of formula (I-b) can be converted to compounds of formula (I-c), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

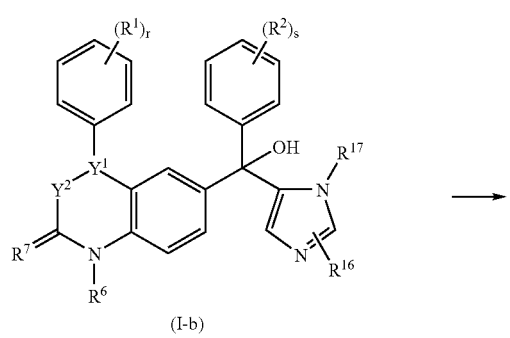

(I-b)

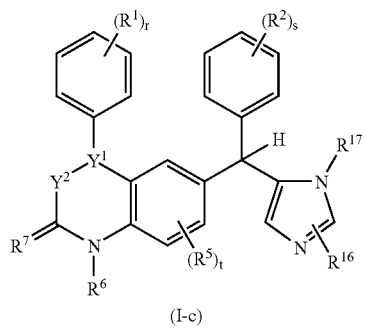

(I-c)

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula H—$NR^{11}R^{12}$ in a reaction-inert solvent, thereby yielding compounds of formula (I-g).

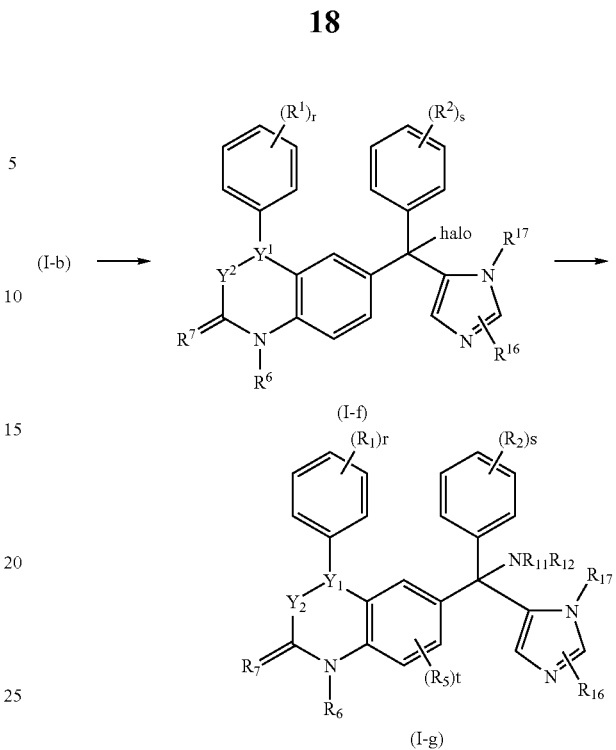

(I-f)

(I-g)

c) compounds of formula (I-b) can be converted into compounds of formula (I-g) for example by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with $SnCl_2$ in the presence of concentrated HCl in acetic acid at reflux;

e) compounds of formula (I) in which >$Y^1$—$Y^2$ represents a radical of formula (y-1) or (y-2) can be converted into corresponding compounds of formula (I) in which >$Y^1$—$Y^2$ represents a radical of formula (y-3) or (y-4) respectively, by conventional reduction procedures for example hydrogenation or reduction by treatment with sodium borohydride in a suitable solvent, e.g. methanol, and vice versa by conventional oxidation procedures; e.g. oxidation with $MnO_2$ in a reaction-inert solvent, e.g. dichloromethane;

f) compounds of formula (I) in which X is oxygen can be converted into corresponding compounds of formula (I) in which X is sulphur with a reagent such as phosphorus pentasulfide or Lawesson's reagent in a suitable solvent such as, for example, pyridine.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The intermediates and starting materials used in the above-described processes my be prepared in conventional manner using procedures known in the art for example as described in the above-mentioned patent specifications WO 97/16443, WO 97/21701, WO 98/40383, WO 98/49157 and WO 00/39082.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (DS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:

a) the sensitisation of tumors to radiotherapy by administering the compound according to the invention before, during or after irradiation of the tumor for treating cancer, for example as described in WO 00/01411;

b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;

c) inhibiting smooth muscle cell proliferation including vascular proliferative disorders, atherosclerosis and restenosis, for example as described in WO 98/55124;

d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating pathologies resulting from heterotri-meric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;
j) suppressing induction of inducible nitric oxide including nitric oxide or cytokine mediated disorders, septic shock, inhibiting apoptosis and inhibiting nitric oxide cytotoxicity;
k) treating malaria.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and anti-estrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment is may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from-0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

Hereinafter "THF" means tetrahydrofuran, "DIPE" means diisopropylether, "DME" means 1,2-dimethoxyethane, "EtOAc" means ethyl acetate, "Et₃N" means triethylamine, "BTEAC" means benzyltriethylammonium chloride, "CDI" means 1,1'-carbonyldiimidazole, "DMSO" means dimethyl sulphoxide, "BuLi" means n-butyl lithium, "Et₂O" means diethylether, DCM means dichloromethane, EDCI means 1-(3-dimethylaminopropyl)-3-ethylcarbodiimide and "DMF" means N,N-dimethylformamide.

F1 refers to the first fraction collected and F2 to the second fraction collected.

Mass spectral data (ms) is given for MH⁺ peaks, determined by electron spray ionisation (ESI).

A. Preparation of the Intermediates

EXAMPLE A1 a) Sodium hydroxide (0.62 mol) was dissolved in methanol (100 ml) and the mixture was cooled till room temperature. 1-bromo-4-nitro-benzene (0.124 mol), followed by 3-chloro-benzeneacetonitrile (0.223 mol) were added dropwise, the temperature raised till 50° C. and the mixture was stirred at room temperature for one night. The mixture was poured into water and ice, the precipitate was filtered off, washed with water and extracted with CH₂Cl₂ and CH₃OH. The organic layer was dried (MgSO₄), filtered off and evaporated till dryness. The residue was taken up in Et₂O, filtered off and dried, yielding 13.2 g (34.8%) of 5-bromo-3-(3-chlorophenyl)-2,1-benzisoxazole, mp. 163° C. (intermediate 1).

b) preparation of

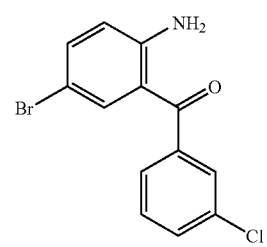

intermediate 2

TiCl₃/15% water (1050 ml) was added at room temperature to a solution of intermediate (1) (0.386 mol) in THF (1350 ml) and the mixture was stirred at room temperature for 2 h. The mixture was poured into water and ice and extracted with CH₂Cl₂. The organic layer was decanted, washed with K₂CO₃ 10%, dried (MgSO₄), filtered off and evaporated, yielding 102 g (85%) of intermediate 2.

c) preparation of

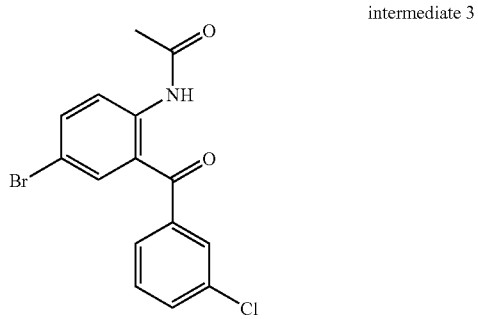

intermediate 3

A solution of intermediate (2) (0.328 mol) and acetic acid anhydride (0.656 mol) in toluene (1200 ml) was stirred and refluxed for one night. The mixture was evaporated and the product was used without further purification, yielding 139 g (quant.) of intermediate 3.

d) 2-methyl-2-propanol, potassium salt (1.635 mol) was added portionwise at room temperature to a solution of intermediate 3 (described in Example A1 c) (0.328 mol) in 1,2-dimethoxyethane (1200 ml) and the mixture was stirred at room temperature for one night. The mixture was evaporated till dryness, the residue was poured into water and ice and decanted. The oily residue was taken up in DIPE, the precipitate was filtered off, washed with EtOAc, acetonitrile and diethyl ether and dried, yielding 88.6 g (80.76%) of 6-bromo-4-(3-chlorophenyl)-2(1H)-quinolinone (intermediate 4).

e) A mixture of intermediate (4) (0.16 mol) in phosphonyl chloride (500 ml) was stirred and refluxed for one night. The mixture was evaporated till dryness, the residue was taken up in ice and water, alkalized with NH₄OH and extracted with CH₂Cl₂. The organic layer was decanted, dried (MgSO₄), filtered off and evaporated, yielding 56 g (100%) of 6-bromo-2-chloro-4-(3-chlorophenyl)quinoline, mp.125° C. (intermediate 5).

f) BuLi 1.6M (0.085 mol) was added at −70° C. under N₂ flow to a solution of intermediate (5) (0.0567 mol) in THF (200 ml). The mixture was stirred for 1 hour. A solution of 4-(diethoxymethyl)-benzaldehyde (0.068 mol) in THF (15 ml) was added dropwise. The mixture was stirred at −70° C. for 2 hours, brought to −30° C., poured out into ice water and extracted with EtOAc. The organic layer was separated, dried (MgSO₄), filtered and the solvent was evaporated. The residue (32.53 g) was purified by column chromatography over silica gel (eluent: CH₂Cl₂/CH₃OH 99/1; 15–35 μm). The pure fractions were collected and the solvent was evaporated, yielding 17.5 g (64%) of (±)-2-chloro-4-(3-chlorophenyl)-α-[4-(diethoxymethyl)phenyl]-6-quinohnemethanol, (intermediate 6).

g) A mixture of intermediate (6) (0.0364 mol) and MnO₂ (0.109 mol) in 1,4-dioxane (200 ml) was stirred and refluxed for 48 hours, cooled and filtered over celite. The solvent was evaporated till dryness. This product was used without further purification, yielding 17 g of [2-chloro-4-(3-chlorophenyl)-6-quinolinyl][4-(diethoxymethyl)phenyl]methanone, (intermediate 7).

h) CH$_3$ONa (0.131 mol) was added dropwise to a solution of intermediate (7)(0.0354 mol) in methanol (200 ml). The mixture was stirred and refluxed overnight, then cooled, poured out into ice water and extracted with CH$_2$Cl$_2$. The organic layer was separated, dried (MgSO$_4$), filtered and the solvent was evaporated. The residue (17.41 g) was purified by column chromatography over silica gel (eluent: cyclohexane/EtOAc 93/7; 15–35 µm). The pure fractions were collected and the solvent was evaporated. The residue (10.5 g, 69%) was crystallized from diethyl ether. The precipitate was filtered off and dried, yielding: 8.54 g (74%) of [4-(3-chlorophenyl)-2-methoxy-6-quinolinyl][4-(diethoxymethyl)phenyl]methanone, mp. 124° C., (intermediate 8).

i) BuLi 1.6M (0.0323 mol) was added dropwise under N$_2$ flow to a solution of 1-methyl-1H-imidazole (0.0258 mol) in THF (40 ml). The mixture was stirred at −70° C. for 30 minutes. ClSiEt$_3$ (4.34 ml) was added. The mixture was stirred and brought slowly to 10° C. then cooled to −70° C. Buli 1.6M (0.0323 mol) was added. The mixture was stirred at −70° C. for 1 hour then brought to −15° C. and cooled to −70° C. A solution of intermediate (8) (0.0215 mol) in THF (150 ml) was added dropwise. The mixture was stirred at −70° C. for 1 hour then brought to −40° C., poured out into ice water and extracted with EtOAc. The organic layer was separated, dried (MgSO$_4$), filtered and the solvent was evaporated. The residue (15.2 g) was purified by column chromatography over silica gel (eluent: CH$_2$Cl$_2$/CH$_3$OH/NH$_4$OH 96/4/0.2; 15–35 µm). The pure fractions were collected and the solvent was evaporated, yielding 6.7 g (56%) of (±)-4-(3-chlorophenyl)-α-[4-(diethoxymethyl)phenyl]-2-methoxy-α-(1-methyl-1H-imidazol-5-yl)-6-quinolinemethanol, mp. 80° C., (intermediate 9).

EXAMPLE A2 a) CH$_3$ONa 30%/methanol (96 ml) was added to a solution of intermediate (5) (0.16 mol) in methanol (500 ml) and the mixture was stirred and refluxed for one night. The mixture was evaporated till dryness. The residue was taken up in CH$_2$Cl$_2$, washed with water and decanted. The organic layer was dried (MgSO$_4$), filtered off and evaporated. -The residue was taken up in (C$_2$H$_5$)$_2$O and DIPE, the precipitate was filtered off and dried, yielding: 48 g (86%) of 6-bromo-4-(3-chlorophenyl)-2-methoxyquinoline, mp. 124° C. (intermediate 10).

b) Intermediate (10) (0.0574 mol) was dissolved in THF (200 ml) under N$_2$ flow. The mixture was cooled to −20° C. and BuLi, 1.6M in hexane (0.0630 mol) was added dropwise. The mixture stood at −30° C. for 30 min., and then DMF (0.1148 mol) was added. The mixture was allowed to warm to room temperature, hydrolyzed and extracted with EtOAc. The organic layer was decanted, dried (MgSO$_4$), filtered, and the solvent was evaporated. The residue was taken up in Et$_2$O. The precipitate was filtered off, washed and dried. The filtrate was evaporated and the residue (10 g) was purified by column chromatography over silica gel (eluent: CH$_2$Cl$_2$/cyclohexane 60/40; 15–40 µm). The pure fractions were collected and the solvent was evaporated, yielding: 7.5 g (88%) of 4-(3-chlorophenyl)-2-methoxy-6-quinolinecarboxaldehyde, (intermediate 11).

c) A solution of 2-(4-bromophenyl)-4,5-dihydro-4,4-diethyl-Oxazole (0.02 mol) in THF (12 ml) was added dropwise at room temperature to a suspension of Mg (0.02 mol) in THF (6 ml) under N2 flow. The mixture was stirred for 30 minutes until the disappearance of Mg, cooled at 0° C. then a mixture of intermediate (11) (0.0133 mol) in THF (12 ml) was added. The mixture was stirred at room temperature for 2 hours, poured out into NH4Cl 10% (aqueous) and extracted with EtOAc. The organic layer was separated, dried (MgSO4), filtered and the solvent was evaporated. The residue was purified by column chromatography over silica gel (eluent: CH$_2$Cl$_2$/CH$_3$OH 97.5/2.5; 15–35 µm). One fraction was collected and the solvent was evaporated yielding 8.2 g (73%). A part (2 g) of the residue (13 g) of this product was crystallized from CH$_2$Cl$_2$. The precipitate was filtered off and dried, yielding: 1.6 g (88%) of (±-4-(3-chlorophenyl)-α-[4-(4,5-dihydro-4,4-dimethyl-2-oxazolyl)phenyl]-2-methoxy-6-quinolinemethanol, mp. 174° C., (intermediate 12).

d) A mixture of intermediate (12) (0.0222 mol) and MnO$_2$ (10.5 g) in dioxane (100 ml) was stirred and refluxed for 18 hours, cooled, filtered over celite and rinsed with CH$_2$C$_2$. The organic layer was separated, dried (MgSO$_4$), filtered and the solvent was evaporated, yielding 8.5 g (81%) of [4-(3-chlorophenyl)-2-methoxy-6-quinolinyl][4-(4,5-dihydro-4,4dimethyl-2-oxazolyl)phenyl]methanone, (intermediate 13).

e) BuLi 1.6M in hexane (0.026 mol) was added dropwise at −70° C. to a mixture of 1-methyl-1H-imidazole (0.027 mol) in low (32 ml) under N$_2$ flow. The mixture was stirred for 15 minutes and ClSiEt$_3$ (0.0268 mol) was added dropwise at −70° C. The mixture was stirred for 15 minutes and BuLi 1.6M in hexane (0.0231 mol) was added dropwise. The mixture was stirred for 15 minutes and a solution of intermediate (13) 0.0149 mol) in THF (38 ml) was added dropwise at −70° C. The mixture was stirred for 30 minutes, poured out into water and extracted with EtOAc. The organic layer was separated, dried (MgSO$_4$), filtered and the solvent was evaporated. The residue (13.1 g) was purified by column chromatography over silica gel (eluent: CH$_2$Cl$_2$/CH$_3$OH/NH$_4$OH 96/4/0.5; 15–35 µm). The pure fractions were collected and the solvent was evaporated, yielding 2 g (21%) of (±-4-(3-chlorophenyl)-α-[4-(4,5-dihydro-4,4-dimethyl-2-oxazolyl)phenyl]-2-methoxy-α-(1-methyl-1H-imidazol-5-yl)-6-quinolinemethanol, mp. 173° C., (intermediate 14).

EXAMPLE A3 a) (±)-4-(3-chlorophenyl)-3,4-dihydro-2(1H)-quinolinone (described in WO 97/21701) (0.0776 mol), then 4-nitrobenzoic acid (0.233 mol) were added at 100° C. to polyphosphoric acid (200 g). The mixture was stirred at 140° C. for 72 hours, cooled at 80° C., poured out into ice water, basified with NH$_4$OH (concentrated) and extracted with CH$_2$Cl$_2$. The organic layer was separated, dried (MgSO$_4$), filtered and the solvent was evaporated. The residue (19.4 g) was purified by column chromatography over silica gel (eluent: CH$_2$Cl$_2$/CH$_3$OH 98/2; 15–35 µm). One fraction was collected and the solvent was evaporated. The residue (9.1 g) was crystallized from 2-propanone. The precipitate was filtered off and dried, yielding 8.5 g (27%) of (±)-4-(3-chlorophenyl)-3,4-dihydro-6-(4-nitrobenzoyl)-2(1H)-quinolinone, mp. 147° C. (intermediate 15).

b) Potassium acetate (0.752 mol) then I2 (0.0501 mol) were added to a mixture of intermediate (15) (0.0209 mol) in acetic acid (85 ml). The mixture was stirred at 130° C. for 72 hours, poured out into ice/Na$_2$S$_2$O$_3$, extracted with CH$_2$Cl$_2$ and washed with K$_2$CO$_3$ 10%. The organic layer was separated, dried (MgSO$_4$), filtered and the solvent was evaporated. The residue (9.1 g) was crystallized from CH$_2$Cl$_2$. The precipitate was filtered off and dried, yielding 4.1 g (48%) of 4-(3-chlorophenyl)-6-(4-nitrobenzoyl)-2 (1H)-quinolinone, mp. 227° C., (intermediate 16).

c) BTEAC (0.001 mol) then iodomethane (0.0198 mol) were added to a mixture of intermediate (16) (0.0099 mol) in NaOH (40 ml) and TBF (40 ml). The mixture was stirred for 3 hours, poured into ice water and extracted with EtOAc. The organic layer was separated, dried (MgSO$_4$), filtered and the solvent was evaporated. The residue was crystallized from 2-propanone/CH$_2$Cl$_2$. The precipitate was filtered off and dried, yielding 2.5 g (60%) 4-(3-chlorophenyl)-1-methyl-6-(4nitrobenzoyl)-2(1H)-quinolinone mp. 174° C., (intermediate 17).

EXAMPLE A4 a) BuLi 1.6M in hexane (0.0316 mol) was added dropwise at −70° C. to a mixture of 6-bromo-4-(3-chlorophenyl)-2-methoxyquinoline (0.0287 mol) in TBIF (100 ml). The mixture was stirred at −70° C. for 30 minutes and a solution of 4-iodo-N-methoxy-N-methyl-benzamide (0.0244 mol) in THF (30 ml) was added. The mixture was stirred at −70° C. for 30 minutes, poured out into ice water and extracted with CH$_2$Cl$_2$. The organic layer was separated, dried (MgSO$_4$), filtered and the solvent was evaporated till dryness, yielding 15.6 g (>100%) of [4-(3-chlorophenyl)-2-methoxy-6-quinolinyl](4-iodophenyl)methanone, (intermediate 18).This product was used without further purification.

b) A mixture of intermediate (18) (0.0244 mol) in HCl 3N (130 ml) and THF (65 ml) was stirred and refluxed for 18 hours, cooled, poured out on ice, filtered, washed several times with water then with 2-propanone/diethyl ether and dried, yielding 9 g (76%) of 4-(3-chlorophenyl)-6-(4-iodobenzoyl)-2(1H)-quinolinone, mp. 251° C. (intermediate 19).

c) BTEAC (0.0019 mol) then iodomethane (0.037 mol) were added to a mixture of intermediate (19) (0.0185 mol) in NaOH, concentrated (90 ml) and THF (90 ml). The mixture was stirred at room temperature for 2 hours, poured out into water and extracted with EtOAc. The organic layer was separated, dried (MgSO$_4$), filtered and the solvent was evaporated till dryness. The residue (9.2 g) was crystallized from 2-propanone/CH$_3$CN. The precipitate was filtered off and dried, yielding 5.6 g (60%) of 4-(3-chlorophenyl)-6-(4-iodobenzoyl)-1-methyl-2(1H)-quinolinone, mp. 184° C. (intermediate 20).

d) BuLi 1.6 m in hexane (0.0196 mol) was added dropwise at −70° C. to a mixture of 1-methyl-1H-imidazole (0.0196 mol) in TBF (20 ml). The mixture was stirred for 15 minutes and ClSiEt3 (0.0202 mol) was added slowly. The mixture was stirred for 15 minutes and Buli 1.6M in hexane (0.0174 mol) was added dropwise. The mixture was stirred for 15 minutes and a suspension of intermediate (20) (0.0112 mol) in THF (40 ml) was added. The mixture was stirred for 15 minutes, poured out into water and extracted with CH$_2$Cl2. The organic layer was separated, dried (MgSO$_4$), filtered and the solvent was evaporated till dryness. The residue (9.5 g) was purified by column chromatography over silica gel (eluent: CH2Cl2/CH3OH/NH4OH 95/5/0.2; 15–35 μm). The pure fractions were collected and the solvent was evaporated. The residue (1 g) was crystallized from 2-propanone. The precipitate was filtered off and dried, yielding 0.82 g (12%) of (±)-4-(3-chlorophenyl)-6-[hydroxy (4-iodophenyl)(1-methyl-1H-imidazol-5-yl)methyl]-1-methyl-2(1H)-quinolinone, mp. 197° C., (intermediate 21).

EXAMPLE A5 a) preparation of

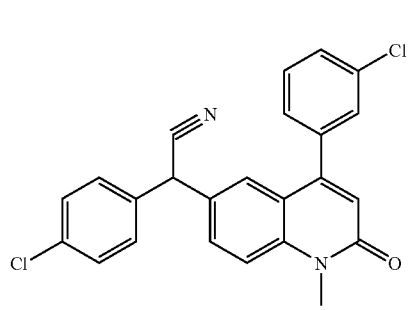

intermediate 22

6-(4-chlorobenzoyl)-4-(3-chlorophenyl)-1-methyl-2(1H)-quinolinone (0.03 mol) was dissolved in 1,2-dimethoxyethane (90 ml) and N,N-dimethylformamide (90 ml) at room temperature under N$_2$ flow. The mixture was cooled to 5° C. 1-[(isocyanomethyl)sulfonyl]4-methylbenzene (0.0375 mol) was added. The mixture was stirred for 30 min. t-butanol (21 ml) and then 2-methyl-2-propanol, potassium salt (0.06 mol) were added at 5° C. The mixture was stirred at 5° C. for 15 min, allowed to warm to room temperature, stirred at room temperature for 3 hours, poured out into water and extracted with EtOAc. The organic layer was separated, dried (MgSO$_4$), filtered and the solvent was evaporated. The residue (15.4 g) was purified by column chromatography over silica gel (eluent: cyclohexane/2-propanol/NH$_4$OH 87.5/12.5/0.75; 20–45 μm). The desired fractions were collected and the solvent was evaporated. The residue was crystallized from diethyl ether. The precipitate was filtered off and dried, yielding 1.8 g of intermediate 22, mp. 136° C.

b) preparation of

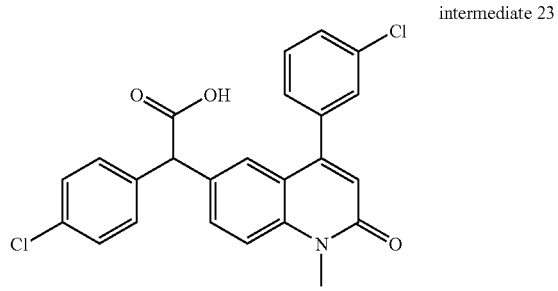

intermediate 23

Acetic acid (24 ml) then intermediate (22) (0.0181 mol) were added portionwise to a solution of sulphuric acid (24 ml) and water (24 ml). The mixture was stirred and refluxed for 3 hours, poured out into ice water, filtered and washed with water. The precipitate was taken up in CH$_2$Cl$_2$. The organic layer was separated, dried (MgSO$_4$), filtered and the solvent was evaporated till dryness. The residue (8.2 g) was crystallized from acetonitrile. The precipitate was filtered off and dried, yielding 7.3 g (92%) of intermediate 23, mp. 202° C.

c) preparation of

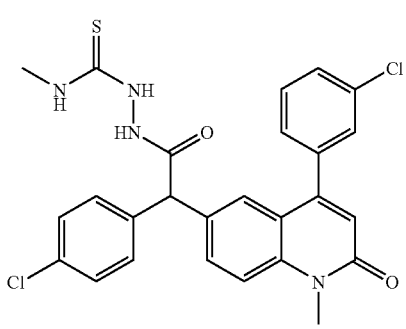

intermediate 24

N-methyl-hydrazinecarbothioamide (0.0137 mol), 1-(3-dimethylaminopropyl)-3-ethyl-carbodimide hydrochloride (0.0137 mol) then 1-hydroxybenzotriazole hydrate (0.0137 mol) were added to a mixture of intermediate (23) (0.0114 mol) in TBF (100 ml). The mixture was stirred at room temperature for 18 hours and water was added. The mixture was filtered and dried. yielding 3 g (50%) of intermnediate 24.

d) preparation of

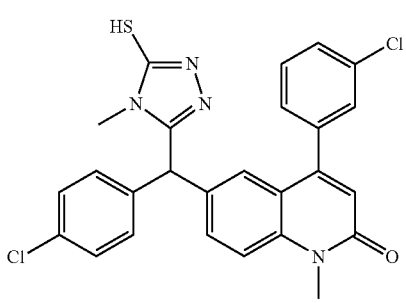

intermediate 25

CH$_3$ONa/CH$_3$OH (0.0057 mol) was added to a mixture of intermediate (24) (0.0057 mol) in methanol (30 ml). The mixture was stirred and refluxed for 3 hours and cooled. The product was used without further purification in the next reaction step. yielding intermediate 25.

e) preparation of

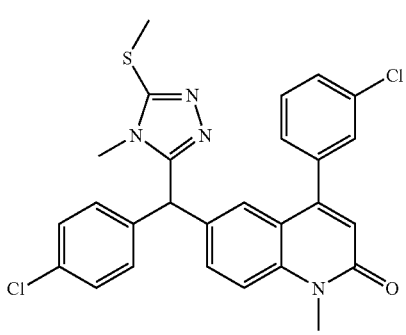

intermediate 26

Iodomethane (0.0057) mol was added at room temperature to the crude mixture of intermediate 25 (0.0057 mol) and CH$_3$ONa/CH$_3$OH in methanol (obtained in the previous step). The mixture was stirred and refluxed for 30 minutes, cooled, poured out into ice water, filtered, washed with Et2O and dried, yielding 2.6 g (84%) of intermediate 26. mp. 147° C.

EXAMPLE A6 a) preparation of

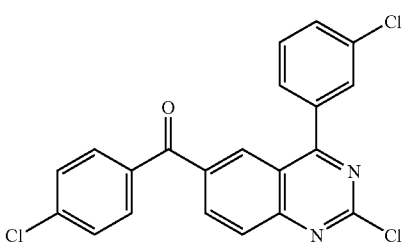

intermediate 27

A mixture of 6-(4-chlorobenzoyl)-4-(3-chlorophenyl)-2 (1H)-quinazolinone (0.0506 mol) (described in WO 98/49157) in phosphoryl chloride (100 ml) was stirred and refluxed for 1 hour. The solvent was evaporated till dryness. The residue was taken up several times in CH$_2$Cl$_2$. The solvent was evaporated till dryness. The residue was taken up in CH$_2$Cl$_2$. The mixture was poured out into ice/NH$_4$OH. The organic layer was separated, dried (MgSO$_4$), filtered, and the solvent was evaporated till dryness. The residue (24.2 g) was crystallized from acetonitrile. The precipitate was filtered off and dried. A part (0.18 g) of the residue (19.8 g, 94%)) was purified by column chromatography over silica gel (eluent: CH$_2$Cl$_2$; 100; 70–200 µm). The pure fractions were collected and the solvent was evaporated. The residue (0.14 g, 78%) was crystallized from diethyl ether. The precipitate was filtered off and dried, yielding 0.12 g (67%) of intermediate 27, mp. 152° C.

b) preparation of

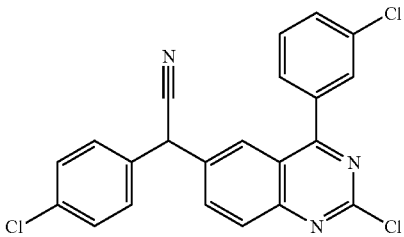

intermediate 28

Tosylmethyl isocyanide (0.0340 mol) then ethanol (38.5 ml) were added at 10° C. to a mixture of intermediate (27) (0.0266 mol) in 1,2-dimethoxyethane (385 ml). 2-methyl-2-propanol, potassium salt (0.0638 mol) was added portionwise. The mixture was stirred at 10° C. for 1 hour, poured out into water and extracted with CH$_2$Cl$_2$. The organic layer was separated, dried (MgSO$_4$), filtered, and the solvent was evaporated. The residue was purified by column chromatography over silica gel (eluent: cyclohexane/EtOAc; 85/15; 15–35 µm). Two fractions were collected and the solvent was evaporated. Yielding: 2.2 g F1 and 0.8 g F2 (both 26.5%). F1 and F2 were combined, yielding 3 g of intermediate 28.

c) preparation of

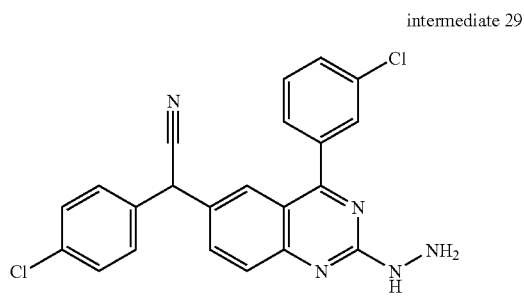
intermediate 29

Hydrazine (12 ml) was added to a mixture of intermediate (28) (0.0007 mol) in THF (30 ml). The mixture was stirred at 60° C. for 2 hours then cooled, poured out into ice water and extracted with EtOAc. The organic layer was separated, washed with water, dried (MgSO$_4$), filtered and the solvent was evaporated, yielding: 2.97 g (quantitative) of intermediate 29.

d) preparation of

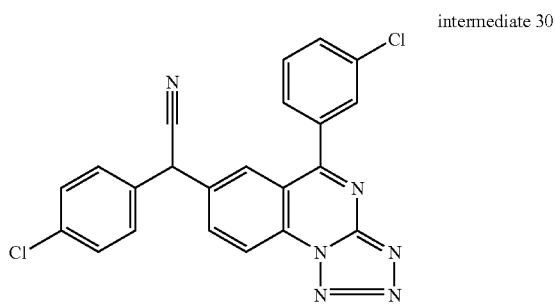
intermediate 30

A mixture of intermediate (29) (0.007 mol) in HCl 1N (37 ml) and THF (15 ml) was cooled to 5° C. A mixture of sodium nitrite (0.0077 mol) in water (12.5 ml) was added dropwise. The mixture was stirred and refluxed for 2 hours then cooled, poured out into ice water and extracted with EtoAc. The organic layer was separated, washed with H2O, dried (MgSO$_4$), filtered and the solvent was evaporated. The residue was purified by column chromatography over silica gel (eluent: CH$_2$Cl$_2$; 100; 15–40 µm). The pure fractions were collected and the solvent was evaporated, yielding 1.8 g (59.6%) of intermediate 30.

e) preparation of

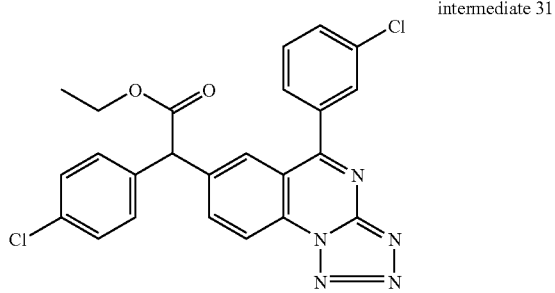
intermediate 31

A mixture of intermediate 30 (0.0038 mol) in ethanol (20 ml) was cooled to −70° C. HCl (gas) was bubbled for 15 minutes. The mixture was stirred from −70° C. to room temperature then stirred at room temperature overnight, poured out into ice water, basified with K$_2$CO$_3$ solid and extracted with EtOAc. The organic layer was separated, dried (MgSO$_4$), filtered, and the solvent was evaporated, yielding 1.6 g (88%) of intermediate 31. MS (ESI) m/z:478, 480,482 (MH$^+$).

f) preparation of

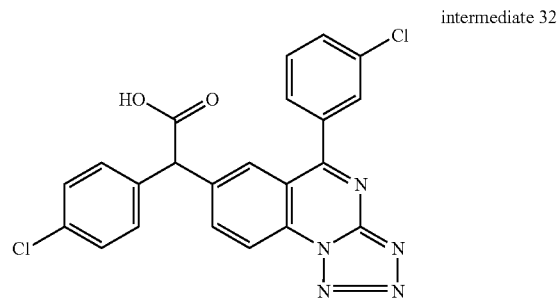
intermediate 32

A mixture of intermediate 31 (0.0033 mol) in THF (16 ml) and water (5 ml) was stirred at room temperature. LiOH, H$_2$O (0.0067 mol) was added portionwise. The mixture was stirred at room temperature for 2 hours, poured out into ice water, acidified with HCl 5N and extracted with CH$_2$Cl2. The organic layer was separated, dried (MgSO$_4$), filtered, and the solvent was evaporated. The residue was crystallized from CH$_3$CN. The precipitate was filtered off and dried, yielding 0.7 g (44%) of intermediate 32.

g) preparation of

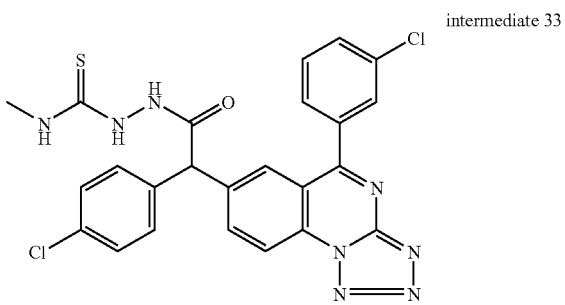
intermediate 33

A mixture of intermediate (32) (0.0016 mol) in CH$_2$Cl$_2$ (7 ml) was stirred at room temperature. 1-(3-dimethylamino-propyl)-3-ethyl-carbodimide hydrochloride (0.0019 mol), 1-hydroxybenzotriazole hydrate (0.0019 mol) and N-methyl-hydrazinecarbothioamide (0.0019 mol) were added at room temperature. The mixture was stirred overnight, poured out into ice water and extracted with CH$_2$Cl$_2$/CH$_3$OH. The organic layer was separated, washed with HCl, dried (MgSO$_4$), filtered and the solvent was evaporated. The residue was taken up in diethyl ether. The precipitate was filtered off and dried, yielding 0.61 g (58%) of intermediate 33.

h) preparation of

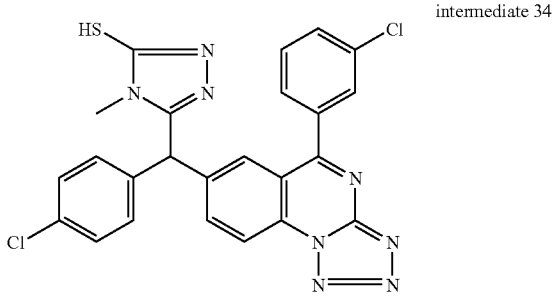

intermediate 34

CH$_3$ONa 30% in methanol (0.0007 mol) was added to a mixture of intermediate (33) (0.0007 mol) in methanol (6 ml). The mixture was stirred and refluxed for 3 hours then cooled, poured out into ice water, extracted with CH$_2$Cl$_2$, saturated with K$_2$CO$_3$ 10% and extracted with CH$_2$Cl$_2$. The organic layer was separated, dried (MgSO$_4$), filtered, and the solvent was evaporated, yielding 0.275 g (71.5%) of intermediate 34, MS (ESI) m/z:519, 521, 523 (MH$^+$).

EXAMPLE A7 a) BuLi 1.6M (0.106 mol) was added dropwise at −70° C. to a solution of 5-bromo-3-(3-chlorophenyl)-2,1-benzisoxazole (0.0816 mol), obtained in Example A1a, in THF (250 ml) under N$_2$ flow. The mixture was stirred at −70° C. for 15 min. A solution of 4-iodo-N-methoxy-N-methyl-benzamide (0.098 mol) in THF (150 ml) was added dropwise at −70° C. The mixture was stirred at −70° C. for 1 hour then brought to room temperature. The mixture was hydrolysed with water, extracted with EtOAc. The organic layer was separated, dried (MgSO$_4$), filtered, and the solvent was evaporated. The residue (48 g) was crystallized from diethyl ether. The precipitate was filtered off and dried, yielding 16.5 g (44%) of [3-(3-chlorophenyl)-2,1-benzisoxazol-5-yl](4-iodophenyl)-methanone, mp.196° C. (intermediate 35).

b) TiCl$_3$ 15% in water (150 ml) was added dropwise at room temperature to a solution of intermediate (35) (0.0324 mol) in THF (150 ml). The mixture was stirred at room temperature for 18 hours, poured out into ice water and extracted with DCM. The organic layer was washed with potassium carbonate 10%, separated, dried (MgSO$_4$), filtered, and the solvent was evaporated. The residue (16 g) was crystallized from diethyl ether. The precipitate was filtered off and dried, yielding 8.7 g (58%) of [4-amino-3-[(3-chlorobenzoyl)phenyl](4iodophenyl)-methanone (intermediate 36).

c) Trichloro-acetyl chloride (0.0226 mol) was added dropwise at 5° C. to a solution of intermediate (36) (0.0188 mol) in DCM (90 ml). The mixture was stirred at 5° C. for 30 min. Triethylamine (0.0226 mol) was added dropwise at 5° C. The mixture was stirred at 5° C. for 30 min, hydrolyzed with water and extracted with DCM. The organic layer was separated, dried (MgSO$_4$), filtered, and the solvent was evaporated till dryness, yielding 12.7 g (100%) of 2,2,2-trichloro-N-[2-(3-chlorobenzoyl)-4-(4-iodobenzoyl)phenyl]-acetamide (intermediate 37).

d) A mixture of intermediate (37) (0.0285 mol) and ammonium acetate (0.057 mol) in DMSO (180 ml) was stirred at 120° C. for 2 hours. The mixture was poured out into ice water. The precipitate was filtered, washed with water (several times) then with CH$_3$CN/diethyl ether and dried at 60° C. under vacuum, yielding 10.3 g (74%) of 4-(3-chlorophenyl)-6-(4-iodobenzoyl)-2(1H)-quinazolinone (intermediate 38).

e) A mixture of intermediate (38) (0.0103 mol) in phosphoryl chloride (20 ml) was stirred and refluxed for 1 hour. The mixture was cooled to room temperature and evaporated till dryness. The residue was taken up in DCM. This solution was poured out into ice/NH$_4$OH and extracted with DCM. The organic layer was separated, dried (MgSO$_4$), filtered, and the solvent was evaporated. The residue (5.3 g) was crystallized from 2-propanone/DIPE. The precipitate was filtered off and dried, yielding 4.25 g (82%) of [2-chloro-4-(3-chlorophenyl)-6-quinazolinyl](4-iodophenyl)-methanone, mp. 153° C. (intermediate 39).

f) Intermediate (39) (0.0198 mol) and tosylmethyl isocyanide (0.0257 mol) were added at 5° C. to DME (200 ml) under N$_2$ flow. Ethanol (0.0396 mol) then 2-methyl-2-propanol, potassium salt (0.0515 mol) were added portionwise at 5° C. The mixture was stirred at 5° C. for 45 minutes, poured out into ice water and extracted with EtOAc. The organic layer was separated, washed with water, dried (MgSO$_4$), filtered and the solvent was evaporated. The residue was purified by column chromatography over silica gel (eluent: cyclohexane/EtOAc 85/15; 15–35 μm). The pure fractions were collected and the solvent was evaporated, yielding 3.5 g (34%) of 2-chloro-4-(3-chlorophenyl)-α-(4-iodophenyl)-6-quinazolineacetonitrile intermediate 40 and 4 g (39%) of [4-(3-chlorophenyl)-2-ethoxy-6-quinazolinyl](4-iodophenyl)-methanone intermediate 77.

g) Intermediate (40) (0.0136 mol) was added at room temperature to THF (70 ml). hydrazine monohydrate (7 ml) was added dropwise. The mixture was stirred at 60° C. for 1 hour and 30 minutes then brought to room temperature, poured out into water and extracted with EtOAc. The organic layer was separated, washed with NH$_4$Cl saturated, dried (MgSO$_4$), filtered and the solvent was evaporated, yielding 6.2 g (89%) of 4-(3-chlorophenyl)-2-hydrazino-α-(4-iodophenyl)-6-quinazolineacetonitrile (intermediate 41).

h) Intermediate (41) (0.0121 mol) was added at 5° C. to a mixture of HCl 1N (60 ml) and THF (60 ml). A solution of sodium nitrite (0.0133 mol) in water (20 ml) was added dropwise at 5° C. The mixture was stirred at 5° C. for 1 hour then brought to room temperature, stirred at room temperature for 5 hours, poured out into ice water and extracted with EtOAc. The organic layer was separated, washed with water, dried (MgSO$_4$), filtered and the solvent was evaporated. The residue was purified by column chromatography over silica gel (eluent: cyclohexane/EtOAc; 70/30; 15–40 μm). The pure fractions were collected and the solvent was evaporated, yielding 3.8 g (60%) which were crystallized from 2-propanone/CH$_3$CN. The precipitate was filtered off and dried till dryness, yielding 3.5 g (55%) of 5-(3-chlorophenyl)-α-(4-iodophenyl)-tetrazolo[1,5-α]quinazoline-7-acetonitrile (intermediate 42).

i) A mixture of intermediate (42) (0.0067 mol) in ethanol (40 ml) was cooled to −70° C. under N$_2$ flow. HCl (gas) was bubbled at −70° C. for 2 hours. The mixture was brought to room temperature then stirred at room temperature overnight and poured out into ice water. EtOAc was added. The mixture was basified with potassium carbonate solid, stirred vigorously for 2 hours and extracted with EtOAc. The organic layer was separated, dried (MgSO$_4$), filtered, and the solvent was evaporated, yielding 3.95 g (quantitative) of ethyl 5-(3-chlorophenyl)-α-(4-iodophenyl)-tetrazolo[1,5-α] quinazoline-7-acetate (intermediate 43).

j) LiOH H$_2$O (0.0134 mol) was added portionwise at room temperature to a mixture of intermediate (43) (0.0067 mol) in THF (38 ml) and water (10 ml). The mixture was stirred at room temperature for 48 hours, poured out into ice water and extracted with DCM, yielding: 3.3 g of 5-(3-chlorophenyl)-α-(4-iodophenyl)-tetrazolo[1,5-α]quinazoline-7-acetic acid, lithium salt (intermediate 44). The product was used without further purification in the next reaction step.

k) Intermediate (44) (0.006 mol) was added at room temperature to THF (40 ml). EDCI (0.0072 mol), 1-hydroxybenzotriazole (0.0072 mol), triethylamine (0.0072 mol) then N-methyl-hydrazinecarbothioamide (0.0072 mol) were added at room temperature. The mixture was stirred at room temperature overnight, poured out into ice water and extracted with DCM. The organic layer was separated, washed with HCl 1N then with water, dried (MgSO$_4$), filtered and the solvent was evaporated, yielding 3.3 g of 2-[(methylamino)thioxomethyl]hydrazide-5-(3-chlorophenyl)-α-(4-iodophenyl)-tetrazolo[1,5-α]quinazoline-7-acetic acid (intermediate 45). The product was used without further purification in the next reaction step.

EXAMPLE A8

A mixture of intermediate (39) (0.001 mol), obtained in Example A7e, NaN$_3$ (0.002 mol) in DMP (10 ml) was stirred at room temperature overnight and poured out into ice water. The precipitate was filtered, washed with water and dried. The residue was taken up in DCM. Water was added. The mixture was extracted with DCM. The organic layer was separated, washed with water, dried (MgSO$_4$), filtered and the solvent was evaporated. The residue was purified by column chromatography over silica gel (eluent: CH$_2$Cl$_2$/EtOAc; 98/2; 15–40 μm). The pure fractions were collected and the solvent was evaporated, yielding 0.35 g (68%). This residue was crystallized from CH$_3$CN/diethyl ether. The precipitate was filtered off and dried, yielding 0.25 g (49%) of [5-(3-chlorophenyl)tetrazolo[1,5-α]quinazolin-7-yl](4-iodophenyl)-methanone, mp. 175° C. (intermediate 46).

EXAMPLE A9

A mixture of intermediate (27) (0.0181 mol), obtained in Example A6a, and NaN$_3$ (0.0272 mol) in DMF (200 ml) was stirred at room temperature for 1 hour and poured out into water. The precipitate was filtered, washed with water and taken up in DCM. The organic layer was separated, dried (MgSO$_4$), filtered, and the solvent was evaporated. The residue was crystallized from 2-propanone/DIPE. The precipitate was filtered off and dried, yielding 6 g (79%) of (4-chlorophenyl)[5-(3-chlorophenyl)tetrazolo[1,5-α] quinazolin-7-yl]-methanone (intermediate 47).

EXAMPLE A10 a) To a solution of 5-bromo-3-(3-chlorophenyl)-2,1-benzisoxazole (0.083 mol), obtained in Example A1a, in THF (250 ml), at −70° C., under N$_2$ flow, was added a solution of BuLi (0.0996 mol) dropwise. The mixture was stirred at −70° C. for 10 minutes. A solution of 2,3-dihydro-1,4-benzodioxan-6-carboxaldehyde (0.0914 mol) in THF (150 ml) was added and the mixture stirred at −70° C. for 1 hour, poured out into water and extracted with EtOAc. The organic layer was separated, washed with water, dried (MgSO$_4$), filtered and the solvent was evaporated. The residue was purified by column chromatography over silica gel (eluent: DCM; 100; 15–40 μm). The pure fractions were collected and the solvent was evaporated, yielding 22 g (57%) of 3-(3-chlorophenyl)-α-(2,3-dhydro-1,4benzodioxin-6-yl)-2,1-benzisoxazole-5-methanol (intermediate 48).

b) MnO$_2$ (0.253 mol) was added portionwise at room temperature to a mixture of intermediate (48) (0.0558 mol) in dioxane (250 ml). The mixture was stirred at 80° C. overnight, then brought to room temperature and filtered over celite. The celite was then washed with DCM. The filtrate was evaporated till dryness. The residue was washed with diethyl ether, filtered and dried under a vacuum, yielding 16 g (73%) of [3-(3-chlorophenyl)-2,1-benzisoxazol-5-yl](2,3-dihydro-1,4-benzodioxin-6-yl)-methanone, mp.195° C. (intermediate 49).

c) TiCl$_3$ 15% in water (100 ml) was added dropwise at room temperature to a mixture of intermediate (49) (0.04 mol) in THF (170 ml). The mixture was stirred at room temperature for 3 hours and poured out into ice water. DCM was added. The organic layer was extracted with DCM and basified with potassium carbonate 10%. The organic layer was separated, dried (MgSO$_4$), filtered, and the solvent was evaporated. The residue was crystallized from CH$_3$CN/ diethyl ether. The precipitate was filtered off and dried under a vacuum, yielding 14.9 g (95%) of [4-amino-3-[(3-chlorobenzoyl]phenyl](2,3-dihydro-1,4-benzodioxin-6-yl)-methanone, mp. 138° C. (intermediate 50).

d) Trichloro-acetyl chloride (0.0454 mol) was added dropwise at 5° C. to a solution of intermediate (50) (0.0378 mol) in DCM (150 ml) under a N$_2$ flow. The mixture was stirred at 5° C. for 30 minutes. Triethylamine (0.0454 mol) was added dropwise at 5° C. The mixture was stirred at 5° C. for 1 hour, then at room temperature for 2 hours and poured out into ice water. DCM was added. The organic layer was washed with water, separated, dried (MgSO$_4$), filtered, and the solvent was evaporated, yielding 20.4 g (100%) of 2,2,2-trichloro-N-[2-(3-chlorobenzoyl)-4[(2,3-dihydro-1,4-benzodioxin-6-yl)carbonyl]phenyl]-acetamide (intermediate 51).

e) A mixture of intermediate (51) (0.0378 mol) and acetic acid ammonium salt (0.0756 mol) in DMSO (200 ml) was stirred at 60° C. for 4 hours, cooled to room temperature, poured out into ice water and stirred. The precipitate was filtered, washed with water, taken up in acetonitrile (warm), filtered, washed with acetonitrile then diethyl ether and dried under a vacuum, yielding 12.6 g (79%) of intermediate (52). The mother layer was evaporated. The residue was purified by column chromatography over silica gel (eluent: CH$_2$Cl$_2$/ CH$_3$OH/NH$_4$OH 97/3/0.5; 15–40 μm). The pure fractions were collected and the solvent was evaporated, yielding 0.7 g F2 (4%) The residue was crystallized from 2-propanone. The precipitate was filtered off and dried, yielding 0.6 g (4%) of 4-(3-chlorophenyl)-6-[(2,3-dihydro-1,4-benzodioxin-6-yl)carbonyl]-2(1H)-quinazolinone, mp. 255° C. (intermediate 52).

f) A mixture of intermediate (52) (0.03 mol) in phosphoryl chloride (100 ml) was stirred at 100° C. for 3 hours and cooled to room temperature. The solvent was evaporated. The residue was taken up in DCM, evaporated till dryness, taken up in DCM, poured out into ice water, basified with potassium carbonate (solid) and extracted with DCM. The organic layer was washed with water, separated, dried (MgSO$_4$), filtered, and the solvent was evaporated. The residue was crystallized from 2-propanone/CH$_3$CN. The precipitate was filtered off and dried under a vacuum, yielding 12.3 g (94%) of intermediate 53. The mother layer was evaporated and the residue was purified by column chromatography over silica gel (eluent: DCM 100; 15–40 μm). The pure fractions were collected and the solvent was evaporated, yielding 0.5 g (4%). The residue was crystallized from 2-propanone. The precipitate was filtered off and dried, yielding 0.4 g (3%) of [2-chloro-4-(3-chlorophenyl)-6-quinazolinyl](2,3-dihydro-1,4-benzodioxin-6-yl)-methanone, mp. 198° C. (intermediate 53).

g) BuLi (0.0492 mol) was added dropwise at −70° C. to a solution of 1-methyl-1H-imidazole (0.0492 mol) in THF (40 ml) under $N_2$ flow. The mixture was stirred for 15 minutes. chlorotriethylsilane (0.0506 mol) was added dropwise. The mixture was stirred at −70° C. for 15 minutes. BuLi (0.0436 mol) was added dropwise. The mixture was stirred for 15 minutes. A solution of intermediate 53 (0.0281 mol) in THF (130 ml) was added dropwise at −70° C. The mixture was stirred at −70° C. for 1 hour, then at −30° C. for 1 hour and poured out into water. EtOAc was added. The mixture was extracted with EtOAc. The organic layer was washed with water, separated, dried ($MgSO_4$), filtered, and the solvent was evaporated. The residue was purified by column chromatography over silica gel (eluent: $CH_2Cl_2$/$CH_3OH$/$NH_4OH$ 96/4/0.5; 15–35 μm). The pure fractions were collected and the solvent was evaporated, yielding 5.7 g (39%) of 2-chloro-4-(3-chlorophenyl)-α-(2,3-dihydro-1,4-benzodioxin-6-yl)-α-(1-methyl-1H-imidazol-5-yl)-6-quinazolinemethanol (intermediate 54).

EXAMPLE A11 a) A mixture of 6-(4-chlorobenzoyl)-4-(3-chlorophenyl)-2(1H)-quinolinone (0.127 mol), described in International Patent Specification WO 97/21701, in phosphoryl chloride (125 ml) was stirred and heated at 40° C. for one night, stirred further at 70° C. for one night and evaporated till dryness, yielding (100%) of [2-chloro-4(3-chlorophenyl)-6-quinolinyl](4-chlorophenyl)-methanone hydrochloride (1:1) (intermediate 55).

b) NaOMe, 30% methanol (300 ml) was added to a mixture of intermediate (55) (0.127 mol) in methanol (285 ml) and the mixture was stirred at 80° C. for one night. The precipitate was filtered off, washed with ethanol and dried. The product (44.8 g, 87%) was taken up in DCM and the layers were separated. The organic layer was dried ($MgSO_4$), filtered off and evaporated till dryness, yielding 32.3 g (62%) of (4-chlorophenyl)[4-(3-chlorophenyl)-2-methoxy-6-quinolinyl]-methanone (intermediate 56).

c) BuLi (0.233 mol) was added dropwise at −70° C. to a solution of 2,4-dihydro-4-methyl-3H-1,2,4-triazole-3-thione (0.0612 mol) in THF (350 ml) under $N_2$ flow. The mixture was stirred at −70° C. for 1 hour and then brought to 0° C. The mixture was stirred at 0° C. for 45 minutes and then cooled to −70° C. A solution of intermediate (56) (0.0612 mol) in THF (150 ml) was added. The mixture was then brought to 0° C., poured out into water and extracted with EtOAc. The organic layer was separated, dried ($MgSO_4$), filtered, and the solvent was evaporated. The residue was purified by column chromatography over silica gel (eluent: Cyclohexane/EtOAc 70/30; 15–35 μm). The pure fractions were collected and the solvent was evaporated, yielding 11.06 g (35%) of 4-(3-chlorophenyl)-α-(4-chlorophenyl)-α-(5-mercapto-4-methyl-4H-1,2,4triazol-3-yl)-2-methoxy-6-quinolinemethanol (intermediate 57), mp. >260° C.

d) Sodium nitrite (0.0095 mol) was added at −70° C. to a solution of nitric acid (10 ml) in water (10 ml). A solution of intermediate (57) (0.0095 mol) in THF (35 ml) was added dropwise carefully. The mixture was stirred at room temperature for 15 minutes, then poured out into ice water, extracted with DCM and washed with potassium carbonate 10%. The organic layer was separated, dried ($MgSO_4$), filtered, and the solvent was evaporated. The residue was purified by column chromatography over silica gel (eluent: $CH_2Cl_2$/$CH_3OH$/$NH_4OH$ 95/5/0.1; 15–40 μm). The pure fractions were collected and the solvent was evaporated, yielding 3.8 g (61%). A sample (0.5 g) was purified by column chromatography over silica gel (eluent: $CH_2Cl_2$/$CH_3OH$/$NH_4OH$ 97/3/0.1; 15–40 μm). The pure fractions were collected and the solvent was evaporated, yielding 0.42 g of 4-(3-chlorophenyl)-α-(4-chlorophenyl)-2-methoxy-α-(4-methyl-4H-1,2,4-triazol-3-yl)-6-quinolinemethanol, mp. 155° C. (intermediate 58).

EXAMPLE A12 a) A mixture of tosylmethyl isocyanide (0.0859 mol) in DMSO (300 ml) was stirred at 10° C. under $N_2$ flow. 2-methyl-2-propanol, potassium salt (0.143 mol) was added portionwise. Methanol (9.9 ml) was added. The mixture was kept at 10° C. for 30 minutes. (4-chlorophenyl)[5-(3-chlorophenyl)tetrazolo[1,5-a]quinolin-7-yl]-methanone (0.0358 mol), obtained as described in the International Patent Specification WO 00/39082, was added portionwise. The mixture was kept at 10° C. for 1 hour, poured out into ice water and extracted with DCM. The organic layer was separated, dried ($MgSO_4$), filtered, and the solvent was evaporated till dryness. The residue (22.8 g) was crystallized from 2-propanone/DIPE. The precipitate was filtered off and dried, yielding 9 g (58%) of 5-(3-chlorophenyl)-α-(4-chlorophenyl)-tetrazolo[1,5-a]quinoline-7-acetonitrile (intermediate 59).

b) Sulfuric acid (25 ml) was added slowly to $H_2O$ (25 ml). Acetic acid (25 ml) was added. Intermediate (59) (0.0190 mol) was added portionwise. The mixture was stirred and refluxed for 18 hours then cooled, poured out into ice water and extracted with DCM. The organic layer was separated, dried ($MgSO_4$), filtered, and the solvent was evaporated till dryness. The residue (8.9 g) was taken up in EtOAc. The organic layer was separated, washed several times with water, dried ($MgSO_4$), filtered and the solvent was evaporated till dryness, yielding 7.8 g (91%) of 5-(3-chlorophenyl)-α-(4-chlorophenyl)-tetrazolo[1,5-a]quinoline-7-acetic acid, MS (ESI) m/z:449, 451, 453 (MH$^+$) (intermediate 60).

c) N-methyl-hydrazinecarbothioamide (0.0208 mol), EDCI (0.0208 mol) then 1-hydroxybenzotriazole (0.0208 mol) were added portionwise to a mixture of intermediate (60) (0.0174 mol) in THF (160 ml). The mixture was stirred at room temperature for 72 hours, poured out into water and extracted with DCM. The organic layer was separated, dried ($MgSO_4$), filtered, and the solvent was evaporated till dryness. The residue (10 g) was crystallized from $CH_3CN$. The precipitate was filtered off and dried, yielding 4.95 g (53%) of 2-[(methylamino)thioxomethyl]hydrazide-5-(3-chlorophenyl)-α-(4-chlorophenyl)-tetrazolo[1,5-a]quinoline-7-acetic acid, MS (ESI) m/z:536, 538, 540 (MH$^+$) (intermediate 61).

d) MeONa/MeOH (0.0092 mol) was added to a mixture of intermediate (61) (0.0092 mol) in methanol (50 ml). The mixture was stirred and refluxed for 3 hours then cooled, yielding 5-[(4-chlorophenyl)[5-(3-chlorophenyl)tetrazolo[1,5-a]quinolin-7-yl]methyl]-4-methyl4H-1,2,4-triazole-3-thiol (intermediate 62). The product was used without further purification in the next reaction step.

e) Iodomethane (0.0092 mol) was added to a mixture of intermediate (62) (0.0092 mol) and MeONa/MeOH (0.0092 mol) in methanol (50 ml). The mixture was stirred at room temperature overnight and poured out into water. The precipitate was filtered washed with diethyl ether and dried, yielding 4.8 g (98%) of 5-(3-chlorophenyl)-7-[(4-chlorophenyl)[4-methyl-5-(methylthio)-4H-1,2,4triazol-3-yl]methyl]-tetrazolo[1,5-a]quinoline, MS (ESI) m/z:532, 534, 536 (MH$^+$) (intermediate 63).

f) A mixture of intermediate (63) (0.0090 mol) and Raney nickel (4.8 g) in ethanol (100 ml) was stirred and refluxed for 2 hours, filtered over celite and washed with DCM. The filtrate was evaporated till dryness. The residue (2 g) was purified by column chromatography over silica gel (eluent: CH$_2$Cl$_2$/CH$_3$OH/NH$_4$OH; 97/3/0.1 to 90/10/0.5; 15–40 µm). Several fractions were collected and the solvent was evaporated, yielding 0.3 g (7%) of 5-(3-chlorophenyl)-7-[(4-chlorophenyl)(4-methyl-4H-1,2,4-triazol-3-yl)methyl]-tetrazolo[1,5-a]quinoline, mp. 140° C. (intermediate 64), 0.8 g (17%) of 4-(3-chlorophenyl)-6-[(4-chlorophenyl)[4-methyl-5-(methylthio)-4H-1,2,4-triazol-3-yl]methyl]-2-quinolinamine, mp. 140° C. (intermediate 65) and 0.4 g (10%) of 4-(3-chlorophenyl)-6-[(4-chlorophenyl)(4-methyl-4H-1,2,4-triazol-3-yl)methyl]-2-quinolinamine, mp. 153° C. (intermediate 66).

g) 3-Bromo-2-oxo-propanoic acid, ethyl ester (0.0007 mol) was added to a mixture of intermediate (66) (0.0006 mol) in DME (3 ml). The mixture was stirred at room temperature for 18 hours. The solvent was removed and the crude product was used without further purification, yielding 2-amino-4(3-chlorophenyl)-6-[(4-chlorophenyl)(4-methyl-4H-1,2,4-triazol-3-yl)methyl]-1-(3-ethoxy-2,3-dioxopropyl)-quinolinium bromide (intermediate 67).

EXAMPLE A13 a) BuLi (0.045 mol) was added dropwise at –70° C. to a solution of 1-methyl-1H-imidazole (0.045 mol) in THF (40 ml) under N$_2$ flow. The mixture was stirred for 15 minutes. Chlorotriethylsilane (0.046 mol) was added dropwise. The mixture was stirred at –70° C. for 15 minutes. BuLi (0.04 mol) was added dropwise. The mixture was stirred for 15 minutes. A solution of intermediate 77 (0.026 mol), obtained in Example A7f, in THF (130 ml) was added at –70° C. The mixture was stirred at –70° C. for 30 minutes, poured out into ice water and extracted with EtOAc. The organic layer was separated, dried (MgSO$_4$), filtered, and the solvent was evaporated. The residue was purified by column chromatography over silica gel (eluent: CH$_2$Cl$_2$/CH$_3$OH/NH$_4$OH 99/1/0.1 to 98/2/0.2 to 97/3/0.3; 15–35 µm). Two fractions were collected and the solvent was evaporated, yielding 6.3 g (41%) of 4-(3-chlorophenyl)-2-ethoxy-α-(4-iodophenyl)-α-(1-methyl-1H-imidazol-5-yl)-6-quinazolinemethanol, mp. 135° C. (intermediate 68).

b) A mixture of intermediate (68) (0.0084 mol), Pd(OAc)$_2$ (0.00084 mol), triphenyl-phosphine (0.0126 mol) and potassium carbonate (0.0168 mol) in iPrOH (40 ml) and DMF (40 ml) was stirred at 90° C. overnight under a 5 bar pressure of CO, cooled, poured out into ice water, extracted with EtOAc and filtered over celite. Celite was rinsed with EtOAc. The organic layer was washed twice with water. The organic layer was separated, dried (MgSO$_4$), and the solvent was evaporated. The residue was purified by column chromatography over silica gel (eluent: CH$_2$Cl$_2$/CH$_3$OH/NH$_4$OH 95/5/0.1; 15–40 µm). The pure fractions were collected and the solvent was evaporated, yielding 1.9 g (41%) of 1-methylethyl 4-[[4-(3-chlorophenyl)-2-ethoxy-6-quinazolinyl]hydroxy(1-methyl-1H-imidazol-5-yl)methyl]-benzoate, mp. 145° C. (intermediate 69).

c) Phosphoryl chloride (0.0068 mol) was added at room temperature to a mixture of intermediate (69) (0.0034 mol) in DMF (20 ml). The mixture was stirred at 90° C. for 3 hours, then cooled, poured out into ice water and extracted with EtOAc. The organic layer was washed twice with H$_2$O/NaCl, separated, dried (MgSO$_4$), filtered and the solvent was evaporated. The residue (1.8 g) was purified by column chromatography over silica gel (eluent: CH$_2$Cl$_2$/CH$_3$OH/NH$_4$OH 95.5/4.5/0.2; 15–40 µm). The pure fractions were collected and the solvent was evaporated, yielding 0.6 g (32%) of 1-methylethyl 4-[[2-chloro-4-(3-chlorophenyl)-6-quinazolinyl]hydroxy(1-methyl-1H-imidazol-5-yl)methyl]-benzoate (intermediate 70).

d) 1.66 ml of a 20% solution of diisobutylaluminium hydride in toluene (Dibal-H) (0.0021 mol) was added dropwise at –70° C. to a mixture of intermediate (70) (0.0021 mol) in THF (20 ml) under N$_2$ flow. The mixture was stirred at –70° C. for 30 minutes. Dibal-H (0.0042 mol) was added. The mixture was stirred at –70° C. for 1 hour and 30 minutes. Dibal-H (0.00525 mol) was added. The mixture was stirred at –70° C. for 30 minutes and poured out into ice water. DCM was added. The mixture was filtered over celite. The organic layer was separated, dried (MgSO$_4$), filtered, and the solvent was evaporated, yielding 0.944 g (95.6%) of α$^1$-[2-chloro-4-(3-chlorophenyl)-6-quinazolinyl]-α$^1$-(1-methyl-1H-imidazol-5-yl)-1,4-benzenedimethanol (intermediate 71).

EXAMPLE A14

BuLi in hexane (0.005 mol) was added at –70° C. to a mixture of 2,2-dimnethyl-N4-pyridinyl-propanamide (0.002 mol) in N,N,N',N'-tetramethylethylenediamine (0.005 mol) and diethyl ether (12 ml) under N$_2$ flow. The mixture was stirred for 15 minutes, then brought to –10° C., stirred for 2 hours and cooled again to –70° C. A solution of 6-(4-chlorobenzoyl)-4-(3-chlorophenyl)-1-methyl-2(1H)-quinolinone (0.0025 mol), described in the International Patent Specification WO97/21701, in THF (10 ml) was added. The mixture was stirred from –70° C. to room temperature for 18 hours. Water was added. The mixture was extracted with EtOAc. The organic layer was separated, dried (MgSO$_4$), filtered, and the solvent was evaporated. The residue (1.4 g) was purified by column chromatography over silica gel (eluent: CH$_2$Cl$_2$/CH$_3$OH/NH$_4$OH 96/4/0.2 to 92/8/0.5; 15–40 µm). The pure fractions were collected and the solvent was evaporated, yielding 0.12 g (10%) of N-[3-[[(4-chlorophenyl)[4-(3-chlorophenyl)-1,2-dihydro-1-methyl-2-oxo-6-quinolinyl]hydroxymethyl]-4-pyridinyl]-2,2-dimethyl-propanamide, MS (ESI) m/z:586, 588, 590 (MH$^+$) (intermediate 72).

EXAMPLE A15 a) BuLi 1.6M in hexane (0.0334 mol) was added dropwise at –70° C. to a solution of 6-bromo-4-(3-chlorophenyl)-2-methoxy-quinoline (0.0304 mol) in THF (100 ml), under N$_2$ flow. The mixture was stirred at –70° C. for 10 minutes. A solution of 3-iodo-N-methoxy-N-methyl-benzamide (0.0274 mol) in THF (40 ml) was added dropwise. The mixture was stirred at –70° C. for 1 hour and poured out into ice water. EtOAc was added. The organic layer was separated, dried (MgSO$_4$), filtered, and the solvent was evaporated, yielding 16.5 g (100%) of [4-(3-chlorophenyl)-2-methoxy-6-quinolinyl](3-iodophenyl)-methanone (intermediate 73). This product was used without further purification in the next reaction step.

b) A solution of intermediate (73) (0.0304 mol) in HCl 3N (150 ml) and THF (70 ml) was stirred and refluxed overnight, brought to room temperature, poured out into ice water and basified with potassium carbonate. The precipitate was filtered, washed with 2-propanone and dried, yielding 13 g (88%) of 4-(3-chlorophenyl)-6-(3-iodobenzoyl)-2(1H)-quinolinone (intermediate 74).

c) Benzyltriethylammonium chloride (0.00267 mol) and iodomethane (0.053 mol) were added to a solution of intermediate (74) (0.0267 mol) in concentrated sodium hydroxide (150 ml) and THF (150 ml). The mixture was stirred at room temperature for 4 hours and poured out into ice water. EtOAc was added. The organic layer was separated, washed with water, dried ($MgSO_4$), filtered and the solvent was evaporated. The residue was crystallized from EtOAc/2-propanone. The precipitate was filtered off and dried, yielding 6 g (45%) of 4-(3-chlorophenyl)-6-(3-iodobenzoyl)-1-methyl-2(1H)-quinolinone, melting point 235° C. (intermediate 75).

d) BuLi 1.6M (13 ml, 0.021 mol) was added dropwise at −70° C. to a solution of 1-methyl-1H-imidazole (0.021 mol) in THF (20 ml) under $N_2$ flow. The mixture was stirred for 15 minutes. chlorotriethylsilane (0.0216 mol) was added. The mixture was stirred for 15 minutes. BuLi 1.6M (11.6 ml, 0.0186 mol) was added. The mixture was stirred for 15 minutes. A solution of intermediate (75) (0.012 mol) in THF (60 ml) was added dropwise. The mixture was stirred at −70° C. for 1 hour and poured out into ice water. AcOEt was added. The organic layer was separated, washed with water, dried ($MgSO_4$), filtered and the solvent was evaporated. The residue was purified by column chromatography over silica gel (eluent: $CH_2Cl_2$/MeOH/$OH_4OH$/93/7/0.2; 15–35 μm). The pure fractions were collected and the solvent was evaporated, yielding 3.7 g (53%) of intermediate 76. A sample (1.2 g) was crystallized from $CH_3CN$/Et2O. The precipitate was filtered off and dried, yielding 0.8 g of 4-(3-chlorophenyl)-6-[hydroxy(3-iodophenyl)(1-methyl-1H-imidazol-5-yl)methyl]-1-methyl-2(1H)-quinolinone, mp. 226° C. (intermediate 76).

B. Preparation of the Final Compounds

EXAMPLE B1

A mixture of intermediate (9) (0.0172 mol) in HCl (3N) (100 ml) was stirred and refluxed for 24 hours then cooled, poured out into $H_2O$ and stirred at room temperature for 1 hour. The precipitate was filtered, washed with $H_2O$ and dried, yielding 7.9 g (98%) of (±)-4-[[4-(3-chlorophenyl)-1,2-dihydro-2-oxo-6-quinolinyl]hydroxy(1-methyl-1H-imidazol-5-yl)methyl]benzaldehyde monohydrochloride mp. >260° C.

EXAMPLE B2

Hydroxylamine, hydrochloride (0.0131 mol) was added to a solution of (±)-4-[[4-(3-chlorophenyl)-1,2-dihydro-2-oxo-6-quinolinyl]hydroxy(1-methyl-1H-imidazol-5-yl)methyl]benzaldehyde monohydrochloride (described in Example B1) (0.0087 mol) in ethanol (45 ml). The mixture was stirred at room temperature for 1 hour and 30 minutes then refluxed for 2 hours, poured out into $K_2CO_3$ 10% and extracted with EtOAc. The organic layer was separated, dried $MgSO_4$), and the solvent was evaporated. The residue (4.86 g) was purified by column chromatography over silica gel (eluent: $CH_2Cl_2$/$CH_3OH$/$NH_4OH$ 95/5/0.1; 15–40 μm). The pure fractions were collected and the solvent was evaporated, yielding: two fractions. The first fraction was crystallized from $CH_3CN$/diethyl ether. The precipitate was filtered off and dried, yielding 1.69 g (38%) of -4-[[4-(3-chlorophenyl)-1,2-dihydro-2-oxo-6-quinolinyl] ethoxy(1-methyl-1H-imidazol-5-yl)methyl]benzaldehyde oxime, of indeterminate E/Z configuration mp. 232° C. The second fraction was crystallized from $CH_3CN$/diethyl ether. The precipitate was filtered off and dried, yielding 1.91 g (45%) of -4-[[4-(3-chlorophenyl)-1,2-dihydro-2-oxo-6-quinolinyl]hydroxy(1-methyl-1H-imidazol-5-yl)methyl] benzaldehyde oxime, of indeterminate E/Z configuration, mp. 230° C.

EXAMPLE B3

A mixture of intermediate (14) (0.009 mol) in HCl 3N (50 ml) was stirred and refluxed for 18 hours, cooled, poured out into NaOH 3N/ice, stirred for 30 minutes and acidified with HCl 3N. The precipitate was filtered, taken up in 2-propanone, filtered and dried, yielding 3.1 g (68%) of (±)-4-[[4-(3-chlorophenyl)-1,2-dihydro-2-oxo-6-quinolinyl]hydroxy(1-methyl-1H-imidazol-5-yl)methyl]benzoic acid monohydrochloride monohydrate, mp. >300° C.

EXAMPLE B4 n BuLi (1.6M in hexane) (4.4 ml, 0.0071 mol) was added dropwise at −70° C. to a solution of 1-methyl-1H-imidazole (0.0071 mol) in THF (8 ml) under $N_2$ flow. The mixture was stirred for 15 minutes. $ClSiEt_3$ (0.0073 mol) was added dropwise at −70° C. The mixture was stirred for 15 minutes. BuLi (1.6M in hexane) (3.9 ml, 0.0062 mol) was added dropwise at −70° C. The mixture was stirred at −70° C. for 15 minutes. A solution of 4-(3-chlorophenyl)-1-methyl-6-(4-nitrobenzoyl)-2(1H)-quinolinone (described in Example A3d) (0.0040 mol) in THF (15 ml) was added. The mixture was stirred at −70° C. for 15 minutes, poured out into $H_2O$ and extracted with EtOAc. The organic layer was separated, dried ($MgSO_4$), filtered and the solvent was evaporated. The residue was purified by column chromatography over silica gel (eluent: $CH_2Cl_2$/$CH_3OH$/$NH_4OH$ 95/5/0.2; 15–40 μm). The pure fractions were collected and the solvent was evaporated. The residue was crystallized from diethyl ether. The precipitate was filtered off and dried, yielding 0.54 g (27%) of (±)-4-(3-chlorophenyl)-6-[hydroxy(1-methyl-1H-imidazol-5-yl)(4-nitrophenyl)methyl]-1-methyl-2(1H)-quinolinone, mp. 230° C.

EXAMPLE B5

CDI (0.00925 mol) was added to a mixture of (±)-4-[[4-(3-chlorophenyl)-1,2-dihydro-2-oxo-6-quinolinyl]hydroxy (1-methyl-1H-imidazol-5-yl)methyl]benzoic acid monohydrochloride monohydrate (described in Example B3) (0.00185 mol) in THF (10 ml). The mixture was stirred at 40° C. for 1 hour.1,4 diazabicyclo[2,2,2]octane (0.00185 mol) and methanol (5 ml) were added. The mixture was stirred at 40° C. for 18 hours, poured out into $H_2O$ and extracted with EtOAc. The organic layer was separated, dried ($MgSO_4$), filtered, and the solvent was evaporated. The residue was crystallized from 2-propanone. The precipitate was filtered off and dried, yielding 0.44 g (48%) of (±-methyl 4-[[4-(3-chlorophenyl)-1,2-dihydro-2-oxo-6-quinolinyl]hydroxy(1-methyl-1H-imidazol-5-yl)methyl]benzoate, mp. 255° C.

EXAMPLE B6

BTEAC (0.00395 mol), then iodomethane (0.00474 mol) were added to a solution of (±)-4-[[4-(3-chlorophenyl)-1,2- dihydro-2-oxo-6-quinolinyl]hydroxy(1-methyl-1H-imidazol-5yl)methyl]benzaldehyde monohydrochloride (described in Example B1) (0.00395 mol) in NaOH (1N) and THF (20 ml). The mixture was stirred at room temperature for 18 hours, poured out into $H_2O$ and extracted with EtOAc. The organic layer was separated, dried ($MgSO_4$), filtered and the solvent was evaporated. The residue (1.1 g) was purified by column chromatography over silica gel (eluent: $CH_2Cl_2/CH_3OH/NH_4OH$ 96/4/0.2; 15–40 μm). The pure fractions were collected and the solvent was evaporated. The residue (0.87 g) was crystallized from diethyl ether. The precipitate was filtered off and dried, yielding 0.61 g (32%) of (±)-4-[[4-(3-chlorophenyl)-1,2-dihydro-1-methyl-2-oxo-6-quinolinyl]hydroxy(1-methyl-1H-imidazol-5-yl)methyl]benzaldehyde, mp. 208° C.

EXAMPLE B7

A mixture of intermediate (26) (0.0044 mol) and Raney Nickel (1.15 g) in ethanol (50 ml) was stirred and refluxed for 18 hours. $CH_2Cl_2$ was added. The mixture was filtered over celite, washed with $CH_2Cl_2$ and evaporated till dryness. The residue was taken in ethanol. Raney Nickel (1.15 g) was added and the mixture was stirred and refluxed for 18 hours, then cooled. The precipitate was filtered over celite, washed with $CH_2Cl_2$ and the filtrate was evaporated. The residue (2.2 g) was purified by column chromatography over silica gel (eluent: $CH_2Cl_2/CH_3OH/NH_4OH$ 95/5/0.1; 15–40 μm). The pure fractions were collected and the solvent was evaporated, yielding 1.39 g (66%) of 4-(3-chlorophenyl)-6-[(4-chlorophenyl)(4-methyl-4H-1,2,4-triazol-3-yl)methyl]-1-methyl-2(1H)-quinolinone, mp. 153° C.

EXAMPLE B8 a) A mixture of (±)-4-(3-chlorophenyl)-6-[hydroxy(1-methyl-1H-imidazol-5-yl)(4-nitrophenyl)methyl]-1-methyl-2(1H)-quinolinone (described in Example B4) (0.00107 mol) in thionyl chloride (6 ml) was stirred at room temperature for 2 hours. The mixture was evaporated. The residue was taken up in $CH_2Cl_2$ and evaporated. The product was used without further purification in the next step, yielding 0.6 g (100%) of (±)-6-[chloro(1-methyl-1H-imidazol-5-yl)(4-nitrophenyl)methyl]4(3-chlorophenyl)-1-methyl-2(1H)-quinolinone monohydrochloride.

b) $NH_3$/2-propanol (sat.solution) (6 ml) was added dropwise at 5° C. to a solution of (±)-6-[chloro(1-methyl-1H-imidazol-5-yl)(4-nitrophenyl)methyl]-4-(3-chlorophenyl)-1-methyl-2(1H)-quinoline monohydrochloride (described in stage a) (0.00108 mol) in THF (6 ml). The mixture was stirred at room temperature for 2 hours, poured out into $H_2O$ and extracted with EtOAc. The organic layer was separated, dried ($MgSO_4$), filtered, and the solvent was evaporated. The residue (0.49 g) was purified by column chromatography over silica gel (eluent: $CH_2Cl_2/CH_3OH/NH4OH$; 95/5/0.5; 15–40 μm). The pure fractions were collected and the solvent was evaporated. A part (0.15 g) of the residue (0.27 g) was crystallized from $CH_3CN$. The precipitate was filtered off and dried, yielding 0.14 g (47%) of (±)-6-[amino(1-methyl-1H-imidazol-5-yl)(4-nitrophenyl)methyl]-4-(3-chlorophenyl)-1-methyl-2(1H)-quinolinone, mp. 258° C.

EXAMPLE B9

$NaBH_4$ (0.00413 mol) was added portionwise at 0° C. to a mixture of (±)-4-[[4-(3-chlorophenyl)-1,2-dihydro-1-methyl-2-oxo-6 quinolinyl]hydroxy (1-methyl-1H-imidazol-5yl)methyl]benzaldehyde (described in Example B6). (0.00207 mol) in THF (10 ml). The mixture was stirred at 0° C. for 30 minutes, poured out into $H_2O$ and extracted with EtOAc. The organic layer was separated, dried ($MgSO_4$), filtered, and the solvent was evaporated. The residue (0.7 g) was purified by column chromatography over silica gel (eluent: $CH_2Cl_2/CH_3OH/NH_4OH$; 90/10/0.5; 15–40 μm). The pure fractions were collected and the solvent was evaporated, yielding 0.5 g (50%) of (±)-4-(3-chlorophenyl)-6-[hydroxy[4-(hydroxymethyl)phenyl](1-methyl-1H-imidazol-5-yl)methyl]-1-methyl-2(1H)-quinolinone, mp. 273° C.

EXAMPLE B10

(4-Chlorophenyl)-boronic acid, (0.00103 mol), $Pd(PPh_3)_4$ (0.000043 mol) then $K_2CO_3$ (2M) (1 ml) were added to a mixture of intermediate (21) (0.00086 mol) in DME (8 ml). The mixture was stirred at 80° C. for 18 hours then cooled and poured out into $H_2O$. EtOAc was added. The mixture was filtered over celite and extracted with EtOAc. The organic layer was separated, dried ($MgSO_4$), filtered, and the solvent was evaporated. The residue (0.6 g) was purified by column chromatography over silica gel (eluent: $CH_2Cl_2/CH_3OH/NH_4OH$; 96/4/0.2; 15–40 μm). The pure fractions were collected and the solvent was evaporated. The residue (0.34 g) was crystallized from 2-propanone. The precipitate was filtered off and dried, yielding 0.26 g (54%) of (±)-6-[(4'-chloro[1,1'-biphenyl]-4-yl)hydroxy(1-methyl-1H-imidazol-5-yl)methyl]-4-(3-chlorophenyl)-1-methyl-2(1H)-quinolinone, mp. 236° C.

EXAMPLE B11

A mixture of (±)-4-[[4-(3-chlorophenyl)-1,2-dihydro-1-methyl-2-oxo-6-quinolinyl]hydroxy(1-methyl-1H-imidazol-5-yl)methyl]benzaldehyde (described in Example B6) (0.000207 mol), 2-methoxy-ethanamine (0.000517 mol) and acetic acid (0.0000207 mol) in acetonitrile (2 ml) was stirred at room temperature for 2 hours. $NaBH_3CN$ (0.000517 mol) was added and the resulting mixture was stirred at room temperature overnight. After addition of water and extraction with EtOAc, the solvent was evaporated. The residue was purified by HPLC. The product fractions were collected and the solvent was evaporated, yielding 0.008 g (7.13%) of (±)-4-(3-chlorophenyl)-6-[hydroxy[4[[(2-methoxyethyl)amino]methyl]phenyl](1-methyl-1H-imidazol-5-yl)methyl]-1-methyl-2(1H)quinolinone, MS (ESI) m/z:543, 545 ($MH^+$).

EXAMPLE B12

A mixture of intermediate (21) (0.00859 mol), $Pd(OAc)_2$ (0.0009 mol), $PPh_3$ (0.0129 mol) and $K_2CO_3$ (0.0172 mol) in 2-propanol (50 ml) and DMF (50 ml) was stirred at 90° C. under a CO pressure (5 bars) for 18 hours then cooled, filtered over celite and washed with EtOAc. The organic layer was separated, washed with $H_2O$, dried ($MgSO_4$), filtered and the solvent was evaporated. The residue was purified by column chromatography over silica gel (eluent: $CH_2Cl_2/CH_3OH/NH_4OH$; 95/5/0.1; 20–45 μm). The pure fractions were collected and the solvent was evaporated. The residue was then purified by column chromatography over kromasil 10 μm (eluent: $CH_3OH/H_2O$; 73/30). The pure fractions were collected and the solvent was evaporated, yielding 1.75 g (38%) of (±)-1-methylethyl 4-[[4-(3-chlorophenyl)-1,2-hydro-1-methyl-2-oxo-6-quinolinyl]hydroxy(1-methyl-1H-imidazol-5-yl)methyl]benzoate, mp. 180° C.

EXAMPLE B13

Air was bubbled in a mixture of 4-(3-chlorophenyl)-6-[(4-chlorophenyl)(4-methyl-4H-1,2,4-triazol-3-yl)methyl]-1-methyl-2(1H)-quinolinone (see Example B7) (0.0018 mol) in N,N-dimethylformamide (8 ml) at 5° C. for 30 minutes. 2-methyl-2-propanol, potassium salt (0.0036 mol) was added portionwise. The mixture was stirred at room temperature for 1 hour, poured out into water, filtered and washed several times with water. The precipitate was taken up in $CH_2Cl_2$. The organic layer was separated dried ($MgSO_4$), filtered and the solvent was evaporated till dryness. The residue (1.1 g) was purified by column chromatography over silica gel (eluent: $CH_2Cl_2/CH_3OH/NH_4OH$ 92/8/0.1; 15–40 μm). The pure fractions were collected and the solvent was evaporated. The residue (0.75 g, 85%) was crystallized from 2 propanone/DIPE. The precipitate was filtered off and dried, yielding 0.68 g (77%) of 4-(3-chlorophenyl)-6-[(4-chlorophenyl)hydroxy(4-methyl-4H-1,2,4-triazol-3-yl)methyl]-1-methyl-2(1H)-quinolinone, mp. 182° C.

EXAMPLE B14

A mixture of (±)-4-(3-chlorophenyl)-6-[hydroxy[4-(hydroxymethyl)phenyl](1-methyl-1H-imidazol-5yl)methyl]-1-methyl-2(1H)-quinolinone (described in Example B9) (0.000823 mol) in thionyl chloride (4 ml) was kept at room temperature for 2 hours. The solvent was evaporated till dryness. The residue was taken up in $H_2O$. EtOAc was added. The mixture was basified with $K_2CO_3$ (10%) and extracted. The organic layer was separated, dried ($MgSO_4$), filtered, and the solvent was evaporated, yielding 0.43 g (>100%) of (±)-6-[[4-(chloromethyl)phenyl]hydroxy(1-methyl-1H-imidazol-5-yl)methyl]-4-(3-chlorophenyl)-1-methyl-2(1H)-quinolinone.

EXAMPLE B15

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (described in Example B14) (0.000694 mol) and NaCN (0.00139 mol) in DMSO (3.5 ml) was stirred at room temperature for 2 hours, poured out into $H_2O$, basified with $K_2CO_3$ (10%) and extracted with EtOAc. The organic layer was separated, dried ($MgSO_4$), filtered, and the solvent was evaporated. The residue (0.2 g) was purified by column chromatography over silica gel (eluent: $CH_2Cl_2/CH_3OH/NH_4OH$; 95/5/0.1; 15–40 μm). The pure fractions were collected and the solvent was evaporated, yielding 0.08 g (23%) of (±)-4-[[4-(3-chlorophenyl)-1,2-dihydro-1-methyl-2-oxo-6-quinolinyl]hydroxy(1-methyl-1H-imidazol-5-yl)methyl]benzeneacetonitrile, as a white foam.

EXAMPLE B16

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (described in Example B14) (0.000397 mol) and MeONa/MeOH (0.000793 mol) in methanol (2 ml) was stirred at room temperature for 48 hours, poured out into $H_2O$ and extracted with EtOAc. The organic layer was separated, dried ($MgSO_4$), and the solvent was evaporated. The residue (0.12 g) was purified by column chromatography over kromasil 10 μm (eluent: $CH_2Cl_2/CH_3OH/NH_4OH$; 97/3/0.1). The pure fractions were collected and the solvent was evaporated, yielding 0.04 g (20%) of (±)-4-(3-chlorophenyl)-6-[hydroxy[4-(methoxymethyl)phenyl](1-methyl-1H-imidazol-5-yl)methyl]-1-methyl-2(1H)-quinolinone, as a white foam, MS (ESI) m/z: 500, 502 ($MH^+$).

EXAMPLE B17

MeLi (0.00258 mol) was added dropwise at −70° C. to a solution of (±)-4-[[4-(3-chlorophenyl)-1,2-dihydro-1-methyl-2-oxo-6-quinolinyl]hydroxy(1-methyl-1H-imidazol-5yl)methyl]benzaldehyde (described in Example B6) (0.001 mol) in THF (5 ml) under $N_2$ flow. The mixture was stirred at −70° C. for 2 hours. $H_2O$ was added. The mixture was extracted with EtOAc. The organic layer was separated, dried ($MgSO_4$), filtered, and the solvent was evaporated. The residue (0.9 g) was purified by column chromatography over silica gel (eluent: $CH_2Cl_2/CH_3OH/NH_4OH$; 95/5/0.2; 15–40 μm). The pure fractions were collected and the solvent was evaporated, yielding 0.3 g (58%) of (±)-4-(3-chlorophenyl)-6-[hydroxy[4-(1-hydroxyethyl)phenyl](1-methyl-1H-imidazol-5-yl)methyl]-1-methyl-2(1H)-quinolinone, mp. 181° C.

EXAMPLE B18

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (described in Example B14) (0.00039 mol), 1-H-imidazole (0.00079 mol) and $K_2CO_3$ (0.0016 mol) in $CH_3CN$ (2 ml) was stirred and refluxed for 4 hours, poured out into $H_2O$ and extracted with $CH_2Cl_2$. The organic layer was separated, dried ($MgSO_4$), filtered, and the solvent was evaporated. The residue (0.2 g) was purified twice by column chromatography over kromasil (eluent: $CH_2Cl_2/CH_3OH/NH_4OH$ 97/3/0.5 then $CH_3OH/H_2O$ 60/40; 10 μm). The pure fractions were collected and the solvent was evaporated, yielding 0.028 g (13%) of (±)-4-(3-chlorophenyl)-6-[hydroxy[4-(1H-imidazol-1-ylmethyl)phenyl](1-methyl-1H-imidazol-5-yl)methyl]-1-methyl-2(1H)-quinolinone, as a white foam, MS (ESI) m/z:536, 538 ($MH^+$).

EXAMPLE B19

A mixture of (±)-1-methylethyl 4-[[4(3-chlorophenyl)-1,2-dihydro-1-methyl-2-oxo-6-quinolinyl]hydroxy(1-methyl-1H-imidazol-5-yl)methyl]benzoate (described in Example B12) (0.00369 mol) and LiOH. $H_2O$ (0.00369 mol) in THF (15 ml) and $H_2O$ (8 ml) was stirred at room temperature for 72 hours, poured out into $H_2O$ and washed with EtOAc. The aqueous layer was evaporated, taken up in 2-propanone/$H_2O$ and acidified with HCl/diethyl ether. The aqueous layer was evaporated. A part of the residue (0.3 g) was taken up in EtOH/diethyl ether. The precipitate was filtered off and dried, yielding 0.2 g (71%) of (±)-4-[[4-(3-chlorophenyl)-1,2-dihydro-1-methyl-2-oxo-6-quinolinyl]hydroxy(1-methyl-1H-imidazol-5-yl)methyl]benzoic acid, mp. >260° C.

EXAMPLE B20

Sodium nitrite (0.0040 mol) was added at 10° C. to nitric acid (5 ml) in water (5 ml). A mixture of intermediate (34) (0.0040 mol) in THF (15 ml) was added dropwise. The mixture was stirred at 10° C. for 5 minutes, poured out into water, basified with $K_2CO_3$ 10% and extracted with EtOAc. The organic layer was separated, dried ($MgSO_4$), filtered, and the solvent was evaporated. The residue was purified by column chromatography over silica gel (eluent: $CH_2Cl_2$/$CH_3OH$/$NH_4OH$; 97.5/2.5/0.1; 15–40 μm). The pure fractions were collected and the solvent was evaporated. Yielding: 0.46 g (24%). This fraction was crystallized twice from $CH_3CN$/diethyl ether. The precipitate was filtered off and dried. Yielding 0.25 g (12%) of 5-(3-chlorophenyl)-7-[(4-chlorophenyl)(4methyl-4H-1,2,4-triazol-3-yl)methyl]-tetrazolo[1,5-a]quinazoline, mp. 217° C.

EXAMPLE B21

A mixture of (±)-4-[[4-(3-chlorophenyl)-1,2-dihydro-1-methyl-2-oxo-6-quinolnyl]hydroxy(1-methyl-1H-imidazol-5-yl)methyl]benzoic acid (described in Example B19) (0.000186 mol), 3-pyridinamine (0.000223 mol), N'-(ethylcarbonimidoyl)-N,N-dimethyl-1,3-propanediamine, monohydrochloride (1.5 equiv, 0.000279 mol), 1-hydroxy-1H-benzotriazole (0.000279 mol) and $Et_3N$ (0.000279 mol) in THF (2 ml) was stirred at room temperature for 18 hours, then taken up in EtOAc and $H_2O$. The organic layer was separated and the solvent was evaporated. The residue was purified by HPLC. The product fractions were collected and the solvent was evaporated, yielding 0.005 g (4.66%) of (±)-4-[[4-(3-chlorophenyl)-1,2-dihydro-1-methyl-2-oxo-6-quinolinyl]hydroxy(1-methyl-1H-imidazol-5yl)methyl]-N-(3-pyridinyl)benzamide, MS (ESI) m/z:576, 578 ($MH^+$).

EXAMPLE B22 a) 4-(3-chlorophenyl)-6-[(4-chlorophenyl)hydroxy(4-methyl-4H-1,2,4-triazol-3-yl)methyl]-1-methyl-2(1H)-quinolinone (0.012 mol) (described in Example B13) was added portionwise at 5° C. to thionyl chloride (6 ml). The mixture was stirred at room temperature for 4 hours. The solvent was evaporated till dryness. The product was used without further purification in the next reaction step, yielding 6-[chloro(4-chlorophenyl)(4-methyl-4H-1,2,4-triazol-3-yl)methyl]-4-(3-chlorophenyl)-1-methyl-2(1H)-quinolinone.

b) 6-[chloro(4-chlorophenyl)(4-methyl-4H-1,2,4-triazol-3-yl)methyl]-4-(3-chlorophenyl)-1-methyl-2(1H)-quinolinone (0.0045 mol) was added at 5° C. to THF (25 ml) under $N_2$ flow. $NH_3$/2-propanol saturated (25 ml) was added dropwise. The mixture was kept for 1 hour, poured out into water and extracted with $CH_2Cl_2$. The organic layer was separated, dried ($MgSO_4$), and the solvent was evaporated till dryness. The residue (2.6 g) was purified by column chromatography over silica gel (eluent: toluene/iPrOH/$NH_4OH$; 50/50/1; 15–40 μm). The pure fractions were collected and the solvent was evaporated. The residue (1.6 g, 73%) was crystallized from $CH_3CN$/DIPE. The precipitate was filtered off and dried. The residue (1.3 g, 59%) was purified by column chromatography over kromasil 10 μm (eluent: $CH_3OH$/$H_2O$; 60/40). The pure fractions were collected and the solvent was evaporated. The residue (1.4 g, 63%) was crystallized from $CH_3CN$/DIPE. The precipitate was filtered off and dried, yielding 1.26 g (57%) of 6-[amino(4-chlorophenyl)(4-methyl-4H-1,2,4-triazol-3-yl)methyl]-4-(3-chlorophenyl)-1-methyl-2(1H)-quinolinone, mp. 210° C.

EXAMPLE B23

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (0.0006 mol), obtained in Example B14, 1H-tetrazole (0.0018 mol) and potassium carbonate (0.0048 mol) in acetonitrile (4 ml) was stirred and refluxed for 18 hours then cooled, poured out into water and extracted with EtOAc. The organic layer was separated, dried ($MgSO_4$), filtered, and the solvent was evaporated, yielding 0.28 g (87%) of a residue which was then purified by column chromatography over silica gel (eluent: $CH_2Cl_2$/$CH_3OH$/$NH_4OH$; 93/7/0.5; 15–40 μm). The pure fractions were collected and the solvent was evaporated, yielding 0.12 g (37%) of 4-(3-chlorophenyl)-6-[hydroxy(1-methyl-1H-midazol-5-yl)[4-(1H-tetrazol-1-ylmethyl)phenyl]methyl]-1-methyl-2(1H)-quinolinone, mp. 160° C.

EXAMPLE B24

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (0.0002 mol), obtained in Example B14, and EtONa/EtOH (0.0005 mol) in ethanol (1 ml) was stirred at room temperature for 18 hours, poured out into water and extracted with EtOAc. The organic layer was separated, dried ($MgSO_4$), filtered, and the solvent was evaporated. The residue (0.1 g) was purified by column chromatography over kromasil 10 μm (eluent: $CH_2Cl_2$/$CH_3OH$; 90/10). The pure fractions were collected and the solvent was evaporated, yielding 0.034 g (33%) of 4-(3-chlorophenyl)-6-[[4-(ethoxymethyl)phenyl]hydroxy(1-methyl-1H-imidazol-5-yl)methyl]-1-methyl-2(1H)-quinolinone, as a white foam, MS (ESI) m/z:514, 516 ($MH^+$).

EXAMPLE B25

A mixture of (±)-6-[[4-(chloromethyl)phenyl]hydroxy(1-methyl-1H-imidazol-5-yl)methyl]-4-(3-chlorophenyl)-1-methyl-2(1H)-quinolinone (0.0002 mol), obtained in Example B14, and 2(3H)-thiazolethione (0.001 mol) in THF (1 ml) and triethylamine (0.1 ml) was stirred at room temperature for 18 hours, poured out into water and extracted with $CH_2Cl_2$/$CH_3OH$. The organic layer was separated, dried ($MgSO_4$), filtered, and the solvent was evaporated. The residue was purified by column chromatography over kromasil 60 μm (eluent: $CH_2Cl_2$/$CH_3OH$; 90/10). The pure fractions were collected and the solvent was evaporated, yielding (70%) of 4(3-chlorophenyl)-6-[hydroxy(1-methyl-1H-imidazol-5-yl)[4-[(2-thiazolylthio)methyl]phenyl]methyl]-1-methyl-2(1H)-quinolinone, as a white foam, MS (ESI) m/z:585, 586 ($MH^+$).

EXAMPLE B26 a) $CH_3ONa$ 30% in methanol (0.0052 mol) was added at room temperature to a mixture of intermediate (45) (0.0052 mol), obtained in Example A7k), in methanol (40 ml). The mixture was stirred and refluxed for 3 hours then brought to room temperature, poured out into ice water and extracted with DCM. The organic layer was separated, dried ($MgSO_4$), and the solvent was evaporated. The residue was purified by column chromatography over silica gel (eluent: $CH_2Cl_2$/$CH_3OH$/$NH_4OH$; 97/3/0.1; 15–40 μm). The pure fractions were collected and the solvent was evaporated, yielding: 0.23 g (7%) of 5-[[5-(3-chlorophenyl)tetrazolo[1,5-a]quinazolin-7-yl](4-iodophenyl)methyl]-4-methyl-4H-1,2,4-triazole-3-thiol.

b) Sodium nitrite (0.0005 mol) was added at 5° C. to a solution of nitric acid (1 ml) in water (1 ml) A solution of 5-[[5-(3-chlorophenyl)tetrazolo[1,5-a]quinazolin-7-yl](4-iodophenyl)methyl]-4-methyl-4H-1,2,4-triazole-3-thiol (0.0005 mol), obtained in stage a), in THF (2 ml) was added dropwise. The mixture was stirred at 5° C. for 15 minutes and poured out into ice water. EtOAc was added. The mixture was washed with potassium carbonate 10%. The organic layer was separated, dried (MgSO$_4$), filtered, and the solvent was evaporated. The residue (0.23 g) was purified by column chromatography over silica gel (eluent: CH$_2$Cl$_2$/CH$_3$OH/NH$_4$OH 97/3/0.1;15–40 μm). The pure fractions were collected and the solvent was evaporated., yielding 0.12 g (44%) of tetrazolo[1,5-a]quinazoline, 5-(3-chlorophenyl)-7-[(4-iodophenyl)(4methyl-4H-1,2,4-triazol-3-yl)methyl]-, mp. 150° C.

c) 5-(3-chlorophenyl)-7-[(4-iodophenyl)(4-methyl-4H-1,2,4-triazol-3-yl)methyl]-tetrazolo[1,5-a]quinazoline (0.000104 mol), obtained in stage b), was added at room temperature to DMF (1 ml). N$_2$ was bubbled at room temperature for 1 hour. Zn(CN)$_2$ (0.000155 mol) then Pd(Ph$_3$)$_4$ (0.0000104 mol) were added. The mixture was stirred at 80° C. overnight then brought to room temperature and poured out into ice water. EtOAc was added. The mixture was filtered over celite. The celite was washed with EtOAc. The filtrate was extracted with EtOAc. The organic layer was separated, dried (MgSO$_4$), filtered, and the solvent was evaporated. The residue was purified by column chromatography over kromasil 5 μm (eluent: CH$_2$Cl$_2$ 100 to CH$_2$Cl$_2$/CH$_3$OH 97/3). The pure fractions were collected and the solvent was evaporated, yielding 0.01 g (20%) of 4-[[5-(3-chlorophenyl)tetrazolo[1,5-a]quinazolin-7-yl](4-methyl-4H-1,2,4-triazol-3-yl)methyl]-benzonitrile, MS (ESI) m/z:477, 479 (MH$^+$).

EXAMPLE B27 a) 2,4-dihydro-4-methyl-3H-1,2,4-Triazole-3-thione, (0.0612 mol) was added to THF (250 ml) at −70° C. under N$_2$ flow. A solution of BuLi (0.122 mol) was added dropwise at −70° C. The mixture was stirred at −70° C. for 1 hour then brought to 0° C., stirred at 0° C. for 1 hour and cooled to −70° C. Intermediate (46) (0.0322 mol), obtained in Example A8, was added portionwise. The mixture was stirred at −70° C. for 1 hour then at −40° C. for 1 hour, poured out into water and extracted with EtOAc. The organic layer was separated, washed with saturated NH$_4$Cl solution, dried (MgSO$_4$), filtered and the solvent was evaporated. The residue was purified by column chromatography over silica gel (eluent: CH$_2$Cl$_2$/CH$_3$OH/NH$_4$OH; 97/3/0.1; 15–35 μm). Two fractions were collected and the solvent was evaporated, yielding 5 g of unreacted starting material and 8.5 g (42%) of 5-(3-chlorophenyl)-α-(4-iodophenyl)-α-(5-mercapto-4-methyl-4H-1,2,4-triazol-3-yl)-tetrazolo[1,5-a]quinazoline-7-methanol, mp. 250° C.

b) 5-(3-chlorophenyl)-α-(4-iodophenyl)-α-(5-mercapto-4-methyl-4H-1,2,4-triazol-3-yl)-tetrazolo[1,5-a]quinazoline-7-methanol, (0.0152 mol), obtained in stage a), was added at room temperature to sodium hydroxide (40 ml) and THF (100 ml). Iodomethane (0.0228 mol) was added dropwise at room temperature. The mixture was stirred at room temperature for 1 hour, poured out into ice water and extracted with EtOAc. The organic layer was separated, dried (MgSO$_4$), filtered, and the solvent was evaporated. The residue was washed with diethyl ether, filtered and dried, yielding 9.74 g (quantitative) of 5-(3-chlorophenyl)-α-(4-iodophenyl)-α-[4-methyl-5-(methylthio)-4H-1,2,4-triazol-3-yl]-tetrazolo[1,5-a]quinazoline-7-methanol.

EXAMPLE B28 a) BuLi 1.6M in hexane (0.0534 mol) was added dropwise at −70° C. to a mixture of 2,4-dihydro-4-methyl-3H-1,2,4-triazole-3-thione (0.0267 mol) in THF (170 ml) under N$_2$ flow. The mixture was stirred at −70° C. for 1 hour then brought to 0° C., stirred for 1 hour and cooled to −70° C. Intermediate (47) (0.0143 mol), obtained in Example A9, was added portionwise. The mixture was stirred at room temperature for 5 hours, poured out into water and extracted with EtOAc. The organic layer was separated, dried (MgSO$_4$), filtered, and the solvent was evaporated, yielding 7.4 g (97%) of 5-(3-chlorophenyl)-α-(4-chlorophenyl)-α-(5-mercaptomethyl-4H-1,2,4triazol-3-yl)-tetrazolo[1,5-a]quinazoline-7-methanol.

b) Iodomethane (0.0118 mol) was added dropwise at room temperature to a mixture of 5-(3-chlorophenyl)-α-(4-chlorophenyl)-α-(5-mercapto-4-methyl-4H-1,2,4-triazol-3-yl)-tetrazolo[1,5-a]quinazoline-7-methanol (0.0078 mol), (obtained in stage a), in sodium hydroxide 1N (20 ml) and THF (45 ml). The mixture was stirred at room temperature for 1 hour, poured out into water and extracted with EtOAc. The organic layer was separated, dried (MgSO$_4$), filtered, and the solvent was evaporated. The residue (4.9 g) was purified by column chromatography over silica gel (eluent: CH$_2$Cl$_2$/CH$_3$OH/NH$_4$OH; 97/3/0.1; 15–40 μm). The pure fractions were collected and the solvent was evaporated, yielding 3.2 g (74%), of 5-(3-chlorophenyl)-α-(4-chlorophenyl)-α-[4-methyl-5-(methylthio)-4H-1,2,4-triazol-3-yl]-tetrazolo[1,5-a]quinazoline-7-methanol. A sample (1.5 g) was crystallized from diethyl ether. The precipitate was filtered off and dried, yielding: 1 g of 5-(3-chlorophenyl)-α-(4-chlorophenyl)-α-[4-methyl-5-(methylthio)-4H-1,2,4-triazol-3-yl]-tetrazolo[1,5-a]quinazoline-7-methanol, melting point 65° C.

c) A mixture of 5-(3-chlorophenyl)-α-(4-chlorophenyl)-α-[4-methyl-5-(methylthio)-4H-1,2,4-triazol-3-yl]-tetrazolo[1,5-a]quinazoline-7-methanol (0.0036 mol) in thionyl chloride (40 ml) was stirred at 60° C. for 5 hours then cooled. The solvent was evaporated. The residue was taken up in DCM. The solvent was evaporated, yielding 2.3 g (quantitative) of 7-[chloro(4-chlorophenyl)[4-methyl-5-(methylthio)-4H-1,2,4-triazol-3-yl]methyl]-5-(3-chlorophenyl)-tetrazolo[1,5-a]quinazoline monohydrochloride. The product was used without further purification in the next reaction step d) NH$_3$/iPrOH saturated solution (40 ml) was added dropwise at 0° C. to a solution of 7-[chloro(4-chlorophenyl)[4-methyl-5-(methylthio)-4H-1,2,4triazol-3-yl)methyl]-5-(3-chlorophenyl)-tetrazolo[1,5-a)quinazoline (0.0036 mol) in THF (80 ml). The mixture was stirred from 0° C. to room temperature then at room temperature for 2 hours, poured out into ice water and extracted with EtOAc. The organic layer was separated, washed with water, dried (MgSO$_4$), filtered and the solvent was evaporated. The residue (2 g) was purified by column chromatography over silica gel (eluent: CH$_2$Cl$_2$/CH$_3$OH/NH$_4$OH; 98/2/0.1; 15–40 μm). The pure fractions were collected and the solvent was evaporated, yielding 0.35 g (18%) of 5-(3-chlorophenyl)-α-(4-chlorophenyl)-α-[4-methyl-5-(methylthio)-4H-1,2,4-triazol-3-yl]-tetrazolo[1,5-a]quinazoline-7-methanamine. A sample (0.15 g) was crystallized from CH$_3$CN/diethyl ether. The precipitate was filtered off and dried, yielding 0.05 g of 5-(3-chlorophenyl)-α-(4-chlorophenyl)-α-[4methyl-5-(methylthio)-4H-1,2,4-triazol-3-yl]-tetrazolo[1,5-a]quinazoline-7-methanamine, mp. 150° C.

e) Raney nickel (6.5 g) was added to a solution of 5-(3-chlorophenyl)-α-(4-chlorophenyl)-α-[4-methyl-5-(methylthio)-4H-1,2,4-triazol-3-yl)-tetrazolo[1,5-a]quinazoline-7-methanamine (0.0012 mol) in 2-propanone (30 ml) under N$_2$ flow. The mixture was stirred at room temperature for 1 hour and 30 minutes, filtered over celite and rinsed with CH$_2$Cl$_2$/CH$_3$OH. The solvent was evaporated. The residue was taken up in DCM. The organic layer was separated, dried (MgSO$_4$), filtered, and the solvent was evaporated. The residue (0.4 g) was purified by column chromatography over silica gel (eluent: CH$_2$Cl$_2$/CH$_3$OH/NH$_4$OH; 96/4/0.5; 15–35 μm). The pure fractions were collected and the solvent was evaporated The residue was crystallized from CH$_3$CN/diethyl ether. The precipitate was filtered off and dried, yielding 0.11 g (18%) of 5-(3-chlorophenyl)-α-(4-chlorophenyl)-α-(4-methyl-4H-1,2,4-triazol-3-yl)-tetrazolo[1,5-a]quinazoline-7-methanamine, mp. 220° C.

EXAMPLE B29 a) Sodium nitrite (0.0094 mol) was added at 5° C. to a mixture of nitric acid (12 ml) and water (12 ml). A solution of 5-(3-chlorophenyl)-α-(4-iodophenyl)-α-(5-mercapto-4-methyl-4H-1,2,4-triazol-3-yl)-tetrazolo[1,5-a]quinazoline-7-methanol (0.0094 mol), obtained in Example B27a, in THF (10 ml) was added. The mixture was stirred at 5° C. for 15 minutes and poured out into ice water. EtOAc was added. The mixture was basified with potassium carbonate 10%. The precipitate was filtered, washed with EtOAc and dried under a vacuum, yielding 3.5 g of fraction F1 (63%) of 5-(3-chlorophenyl)-α-(4-iodophenyl)-α-(4-methyl-4H-1,2,4-triazol-3-yl)-tetrazolo[1,5-a]quinazoline-7-methanol. The filtrate was extracted with EtOAc. The organic layer was separated, dried (MgSO$_4$), filtered, and the solvent was evaporated. The residue was crystallized from 2-propanone. The precipitate was filtered off and dried, yielding 1.5 g F2 (27%). This fraction was taken up in water. The mixture was stirred. The precipitate was filtered off and dried, yielding 1.2 g (21%) of 5-(3-chlorophenyl)-α-(4-iodophenyl)-α-(4-methyl-4H-1,2,4triazol-3-yl)-tetrazolo[1,5-a]quinazoline-7-methanol, mp. 228° C.

b) A mixture of 5-(3chlorophenyl)-α-(4-iodophenyl)-α-(4-methyl-4H-1,2,4-triazol-3-yl)-tetrazolo[1,5-a]quinazoline-7-methanol (0.0076 mol) in thionyl chloride (50 ml) was stirred at 65° C. for 4 hours, then cooled and the solvent was evaporated till dryness. The residue was taken up twice with DCM. The solvent was evaporated, yielding 7-[chloro (4-iodophenyl)(4-methyl-4H-1,2,4-triazol-3-yl)methyl]-5-(3-chlorophenyl)-tetrazolo[1,5-a]quinazoline monohydrochloride. This product was used directly in the next reaction step.

c) NH$_3$/iPrOH (45 ml) was added dropwise at 5° C. to a mixture of 7-[chloro(4-iodophenyl)(4-methyl-4H-1,2,4-triazol-3-yl)methyl]-5-(3-chlorophenyl)-tetrazolo[1,5-a]quinazoline (0.0076 mol) in THF (45 ml). The mixture was brought to room temperature, poured out into a pressure vessel, stirred at 60° C. for 6 hours, cooled and poured out into ice water. The precipitate was filtered off and dried under a vacuum, yielding 1.6 g of a first batch of 5-(3-chlorophenyl)-α-(4-iodophenyl)-α-(4-methyl-4H-1,2,4-triazol-3-yl)-tetrazolo[1,5-a]quinazoline-7-methanamine (35%) The aqueous layer was extracted with DCM. The organic layer was separated, dried (MgSO$_4$), filtered, and the solvent was evaporated. The residue (1.7 g) was purified by column chromatography over silica gel (eluent: toluene/iPrOH/NH$_4$OH 84/15/1; 15–40 μm). The pure fractions were collected and the solvent was evaporated, yielding 1.03 g (23%) of a second batch of 5-(3-chlorophenyl)-α-(4-iodophenyl)-α-(4-methyl-4H-1,2,4-triazol-3-yl)-tetrazolo[1,5-a]quinazoline-7-methanamine. A sample (0.23 g) was crystallized from CH$_3$CN, the precipitate was filtrated and dried yielding 0.09 g of 5-(3-chlorophenyl)-α-(4-iodophenyl)-α-(4-methyl-4H-1,2,4-triazol-3-yl)-tetrazolo[1,5-a]quinazoline-7-methanamine, mp. 238° C.

d) N$_2$ was bubbled at room temperature in a solution of 5-(3-chlorophenyl)-α-(4-iodophenyl)-α-(4-methyl-4H-1,2,4-triazol-3-yl)-tetrazolo[1,5-a]quinazoline-7-methanamine (0.0024 mol) in DMF (15 ml) for 1 hour. Zn(CN)$_2$ (0.0036 mol) and Pd(PPh$_3$)$_4$ (0.0002 mol) were added. The mixture was stirred at 80° C. for 1 hour, cooled, poured out into ice water and extracted with EtOAc. The precipitate was filtered off (secondary product). The organic layer was washed twice with water then with saturated NaCl, separated, dried (MgSO$_4$), filtered, and the solvent was evaporated. The residue was purified by column chromatography over silica gel (eluent: CH$_2$Cl$_2$/CH$_3$OH/NH$_4$OH 95/5/0.2 to 80/20/2; 15–35 μm). The pure fractions were collected and the solvent was evaporated, yielding 0.425 g (35%) of 4-[amino [5-(3-chlorophenyl)tetrazolo[1,5-a]quinazolin-7-yl](4-methyl-4H-1,2,4-triazol-3-yl)methyl]-benzonitrile which were crystallized from CH$_3$CN. The precipitate was filtered off and dried, yielding 0.19 g (16%) of 4-[amino[5-(3-chlorophenyl)tetrazolo[1,5-a]quinazolin-7-yl](4methyl-4H-1,2,4-triazol-3-yl)methyl]-benzonitrile, mp. 194° C.

EXAMPLE B30

A mixture of intermediate (54) (0.00424 mol), obtained in Example A10 g, in HCl 6N (25 ml) was stirred at 100° C. for 3 hours and cooled to room temperature. The solvent was evaporated till dryness. The residue was taken up in CH$_2$Cl$_2$/CH$_3$OH (small quantity), poured out into ice water, basified with potassium carbonate solid and extracted with CH$_2$Cl$_2$/CH$_3$OH (small quantity). The organic layer was separated, dried (MgSO$_4$), filtered, and the solvent was evaporated. The residue was purified by column chromatography over silica gel (eluent: CH$_2$Cl$_2$/CH$_3$OH/NH$_4$OH 92/8/1; 15–40 μm). The pure fractions were collected and the solvent was evaporated, yielding 1.2 g (57%) of 4-(3-chlorophenyl)-6-[(2,3-dihydro-1,4-benzodioxin-6-yl)hydroxy(1-methyl-1H-imidazol-5-yl)methyl]-2(1H)-quinazolinone, which were crystallized from 2-propanone/EtOH. The precipitate was filtered off and dried under a vacuum, yielding 1.1 g (52%) of 4-(3-chlorophenyl)-6-[(2,3-dihydro-1,4-benzodioxin-6-yl)hydroxy(1-methyl-1H-imidazol-5-yl)methyl]-2(1H)-quinazolinone, mp. >260° C.

EXAMPLE B31

N$_2$ was bubbled at room temperature to a solution of 4-(3-chlorophenyl)-6-[(4-chlorophenyl)(4-methyl-4H-1,2,4-triazol-3-yl)methyl]-1-methyl-2(1H)-quinolinone (0.00105 mol), obtained in Example B7, in DME (8.5 ml) for 30 minutes. DCM (2 ml) was added. Then 2-methyl, 2-propanol, potassium salt (0.0021 mol) was added portionwise. The mixture was stirred for 1 hour, poured out into water and extracted with DCM. The organic layer was separated, dried (MgSO$_4$), filtered, and the solvent was evaporated till dryness. The residue (0.55 g) was purified by column chromatography over silica gel (eluent: CH$_2$Cl$_2$/CH$_3$OH 100 to 95/5; 10 μm). The pure fractions were collected and the solvent was evaporated. The residue (0.35 g, 64%) was crystallized from CH$_3$CN. The precipitate was filtered off and dried, yielding 0.28 g (51%) of 6-[2-chloro-1-(4-chlorophenyl)-1-(4-methyl-4H-1,2,4-triazol-3-yl)ethyl]-4-(3-chlorophenyl)-1-methyl-2(1H)-quinolinone, mp. 260° C.

EXAMPLE B32

A mixture of intermediate (58) (0.0163 mol), obtained in Example A11d, in HCl 6N (80 ml) was stirred and refluxed for a week end, poured out into ice water, basified with potassium carbonate 10% and extracted with $CH_2Cl_2$/$CH_3OH$ (a few quantity). The organic layer was separated, dried ($MgSO_4$), filtered, and the solvent was evaporated. The residue was crystallized from DCM. The precipitate was filtered off and dried, yielding 5.67 g (73%) of 4-(3-chlorophenyl)-6-[(4-chlorophenyl)hydroxy(4-methyl-4H-1,2,4triazol-3-yl)methyl]-2(1H)-quinolinone. A sample (0.5 g) was dissolved in water, stirred overnight, filtered, rinsed with DIPE and dried at 80° C. under a vacuum, yielding 0.4 g of 4-(3-chlorophenyl)-6-[(4-chlorophenyl)hydroxy(4-methyl-4H-1,2,4-triazol-3-yl)methyl]-2(1H)-quinolinone, mp.>260° C.

EXAMPLE B33

NaH 60% in oil (0.0023 mol) was added at room temperature to a mixture of 4-(3-chlorophenyl)-6-[(4-chlorophenyl)hydroxy(4-methyl-4H-1,2,4-triazol-3-yl)methyl]-2(1H)-quinolinone (0.0021 mol), obtained in Example B32, in DMF (10 ml). The mixture was stirred for 30 minutes. 4-(Bromomethyl)-benzonitrile (0.0023 mol) was added. The mixture was stirred at room temperature for 18 hours, then at 80° C. for 2 hours, then overnight, cooled and poured out into ice water. The precipitate was filtered, taken up in DCM. The organic layer was separated, dried ($MgSO_4$), filtered, and the solvent was evaporated. The residue (0.8 g) was purified by column chromatography over silica gel (eluent: $CH_2Cl_2$/$CH_3OH$ 100/0 to 90/10; 10 µm). The pure fractions were collected and the solvent was evaporated. The residue (0.1 g) was purified by column chromatography over kromasil (eluent: $CH_3CN$/$H_2O$ 60/40; 10 µm). The pure fractions were collected and the solvent was evaporated, yielding 0.078 g (6%) of 4-[[4-(3-chlorophenyl)-6-[(4-chlorophenyl)hydroxy(4-methyl-4H-1,2,4-triazol-3-yl)methyl]-2-oxo-1(2H)-quinolinyl]methyl]-benzonitrile, mp. 185° C.

EXAMPLE B34

$N_2$ was bubbled at room temperature into a solution of 4-(3-chlorophenyl)-6-[(4-chlorophenyl)(4-methyl-4H-1,2,4-triazol-3-yl)methyl]-1-methyl-2(1H)-quinolinone (0.001 mol), obtained in Example B7, in DME (8.5 ml) for 30 minutes. Iodomethane (0.0015 mol) and then 2-methyl-2-propanol, potassium salt (0.0021 mol) were added portionwise. The mixture was stirred at room temperature for 30 minutes, poured out into water and extracted with DCM. The organic layer was separated, dried ($MgSO_4$), filtered and the solvent was evaporated till dryness. The residue (0.54 g) was purified by column chromatography over silica gel (eluent: $CH_2Cl_2$ 100 to $CH_2Cl_2$/$CH_3OH$ 95/5; 10 µm). The pure fractions were collected and the solvent was evaporated, yielding 0.28 g F1 (54%) dissolved in 2-propanone and converted into the ethanedioic acid salt. The solvent was evaporated till dryness. The residue was crystallized from ethanol. The precipitate was filtered off and dried, yielding 0.24 g (39%) of 4-(3-chlorophenyl)-6-[1-(4-chlorophenyl)-1-(4-methyl-4H-1,2,4-triazol-3-yl)ethyl]-1-methyl-2(1H)-quinolinone ethanedioate (1:1), mp. 130° C.

EXAMPLE B35

A mixture of intermediate (67) (0.0006 mol), obtained in Example A12 g, in ethanol (3 ml) was stirred and refluxed for 18 hours. Potassium carbonate 10% was added. The mixture was extracted with DCM. The organic layer was separated, dried ($MgSO_4$), filtered, and the solvent was evaporated till dryness. The residue (0.3 g) was purified by column chromatography over kromasil (eluent: $CH_2Cl_2$ 100 to $CH_2Cl_2$/$CH_3OH$ 90/10; 10 µm). The pure fractions were collected and the solvent was evaporated. The residue (0.12 g, 33%) was crystallized from $CH_3CN$/DIPE. The precipitate was filtered off and dried, yielding 0.091 g (25%) of ethyl 5-(3-chlorophenyl)-7-[(4-chlorophenyl)(4-methyl-4H-1,2,4-triazol-3-yl)methyl]-imidazo[1,2-a]quinoline-2-carboxylate, mp. 220° C.

EXAMPLE B36

A mixture of intermediate (71) (0.0019 mol), obtained in Example A13d, and $NaN_3$ (0.0057 mol) in DMP (10 ml) was stirred at 90° C. for 3 hours, then cooled, poured out into ice water and extracted with DCM. The organic layer was separated, dried ($MgSO_4$), filtered, and the solvent was evaporated. The residue was purified by column chromatography over silica gel (eluent: $CH_2Cl_2$/$CH_3OH$/$NH_4OH$ 931710.5; 15–40 µm). The pure fractions were collected and the solvent was evaporated, yielding 0.48 g of fraction F1 (50.5%). F1 was crystallized from $CH_3CN$. The precipitate was filtered off and dried, yielding 0.1 g $\alpha^1$-[5-(3-chlorophenyl)tetrazolo[1,5-a]quinazolin-7-yl]-$\alpha^1$-(1-methyl-1H-imidazol-5-yl)-1,4-benzenedimethanol, mp. 180° C.

EXAMPLE B37

A mixture of (±)-6-[[4-(chloromethyl)phenyl]hydroxy(1-methyl-1H-imidazol-5-yl)methyl]-4(3-chlorophenyl)-1-methyl-2(1H)-quinolinone (0.000198 mol), obtained in Example B 14, 1-butanamine (3 equiv, 0.000595 mol) and potassium carbonate (6 equiv, 0.001188 mol) in acetonitrile (1 ml) was stirred and refluxed for 18 hours. Water and EtOAc were added. The organic layer was separated, and the extract solvent was evaporated. The residue was purified by column chromatography over kromasil (eluent: $CH_2Cl_2$ 100 to $CH_2Cl_2$/$CH_3OH$ 90/10; 5 µm). The product fractions were collected and the solvent was evaporated,yielding 0.018 g (16.78%) of 6-[[4-[(butylamino)methyl]phenyl]hydroxy(1-methyl-1H-imidazol-5-yl)methyl]-4(3-chlorophenyl)-1-methyl-2(1H)-quinolinone, MS (ESI) m/z:541, 543 (MH).

EXAMPLE B38

$MnO_2$ (0.2 g) was added portionwise at room temperature to a mixture of $\alpha^1$-[5-(3-chlorophenyl)tetrazolo[1,5-a]quinazolin-7-yl]-$\alpha^1$-(1-methyl-1H-imidazol-5-yl)-1,4-benzenedimethanol (0.0004 mol), obtained in Example B36, in THF (2 ml). The mixture was stirred at 80° C. for 48 hours, then brought to room temperature and filtered over celite. The celite was then washed with EtOAc. The filtrate was evaporated till dryness. The residue was purified by column chromatography over silica gel (eluent: $CH_2Cl_2$/$CH_3OH$/$NH_4OH$ 95/5/0.1; 15–40 µm). The pure fractions were collected and the solvent was evaporated, yielding 0.1 g (51%) of fraction F1. F1 was crystallized from $CH_3CN$/diethyl ether. The precipitate was filtered off and dried, yielding 0.05 g (25%) of 4-[[5-(3-chlorophenyl)tetrazolo[1, 5-a]quinazolin-7-yl]hydroxy(1-methyl-1H-imidazol-5-yl)methyl]-benzaldehyde, mp. 170° C.

EXAMPLE B39

BuLi 1.6M (0.0025 mol) was added to THF (6 ml) at −20° C. under $N_2$ flow. A solution of N-(1-methylethyl)-2-propanamine, hydrochloride (0.0025 mol) in THF (1 ml) was added to this mixture. The mixture was stirred at 0° C. for 1 hour and cooled to −70° C. A solution of 4-chloropyridine, hydrochloride (0.0025 mol) in THF (1 ml) was added dropwise. The mixture was stirred at −70° C. for 2 hours. A solution of 6-(4-chlorobenzoyl)-4-(3-chlorophenyl)-1-methyl-2(1H)-quinolinone (0.0025 mol), described in International Patent Specification WO 97/21701, in THF (10 ml) was added dropwise and the mixture was stirred at −70° C. for 18 hours. Water was added and this mixture was extracted with EtOAc. The organic layer was separated, dried ($MgSO_4$), filtered, and the solvent was evaporated. The residue (1.3 g) was purified by column chromatography over silica gel (eluent: $CH_2Cl_2/CH_3OH/NH_4OH/97/3/0.5$; 15–40 μm), yielding 0.4 g of fraction F1 which was crystallized from 2-propanone, yielding 0.31 g (24%) of 4-(3-chlorophenyl)-6-[(4-chlorophenyl)(4-chloro-3-pyridinyl)hydroxymethyl]-1-methyl-2(1H)-quinolinone, mp. 178° C.

EXAMPLE B40 a) A mixture of 4(3-chlorophenyl)-6-[(4-chlorophenyl)(4-chloro-3-pyridinyl)hydroxymethyl]-1-methyl-2(1H)-quinolinone, (0.0004 mol), obtained in Example B39, in thionyl chloride (2 ml) was stirred at room temperature for 4 hours, then cooled and the solvent was evaporated. The residue was taken up in DCM. The solvent was evaporated, yielding 0.23 g of 6-[chloro(4-chlorophenyl)(4-chloro-3-pyridinyl)methyl]-4(3-chlorophenyl)-1-methyl-2(1H)-quinolinone monohydrochloride. This product was used without further purification.

b) NH/iPrOH (2 ml) was added dropwise at 5° C. to a mixture of 6-[chloro(4-chlorophenyl)(4-chloro-3-pyridinyl)methyl]-4(3-chlorophenyl)-1-methyl-2(1H)-quinolinone (0.0004 mol), obtained in stage a), in THF (2 ml). The mixture was stirred at room temperature for 6 hours, poured out into water and extracted with EtOAc. The organic layer was separated, dried ($MgSO_4$), filtered, and the solvent was evaporated. The residue was purified by column chromatography over silica gel (eluent: $CH_2Cl_2/CH_3OH$ 98/2; 10 μm). The pure fractions were collected and the solvent was evaporated. The residue (0.15 g) was crystallized from acetonitrile/$CH_2Cl_2$. The precipitate was filtered off and dried, yielding 0.034 g (15%) of 6-[amino(4-chlorophenyl)(4-chloro-3-pyridinyl)methyl]-4(3-chlorophenyl)-1-methyl-2(1H)-quinolinone, mp. 180° C.

c) A mixture of 6-[amino(4-chlorophenyl)(4-chloro-3-pyridinyl)methyl]-4(3-chlorophenyl)-1-methyl-2(1H)-quinolinone, (0.0001 mol), obtained in stage b), and $CH_3ONa$ in methanol (0.0009 mol) in methanol (1 ml) and DCM (1 ml) was stirred and refluxed for 18 hours, poured out into water and extracted with EtOAc. The organic layer was separated, dried ($MgSO_4$), filtered, and the solvent was evaporated. The residue (0.11 g) was purified by column chromatography over silica gel (eluent: $CH_2Cl_2/CH_3OH/NH_4OH$ 95/5/0.1; 35–70 μm). The pure fractions were collected and the solvent was evaporated, yielding 0.041 g (41%) of 6-[amino(4-chlorophenyl)(4-methoxy-3-pyridinyl)methyl]-4-(3-chlorophenyl)-1-methyl-2(1H)-quinolinone, MS (ESI) m/z: 516, 518, 520 ($MH^+$).

EXAMPLE B41 a) A mixture of 4-[[4-(3-chlorophenyl)-1,2-dihydro-2-oxo-6-quinolinyl]hydroxy(1-methyl-1H-imidazol-5-yl)methyl]benzaldehyde oxime, of indeterminate E/Z configuration (0.0035 mol), obtained in Example B2, and 1,1'-carbonyldiimidazole (0.028 mol) in THF (55 ml) was stirred at room temperature for 24 hours, poured out into ice water and extracted with EtOAc. The organic layer was separated, dried ($MgSO_4$), filtered and the solvent was evaporated. The residue (2.8 g) was purified by column chromatography over silica gel (eluent: $CH_2Cl_2/CH_3OH/NH_4OH$ 90/10/0.5; 15–40 μm). The pure fractions were collected and the solvent was evaporated, yielding 0.85 g of (±)-4-[[4-(3-chlorophenyl)-1,2-dihydro-2-oxo-6-quinolinyl]hydroxy(1-methyl-1H-imidazol-5-yl)methyl]benzonitrile.

b) A mixture of (±)-4-[[4-(3-chlorophenyl)-1,2-dihydro-2-oxo-6-quinolinyl]hydroxy(1-methyl-1H-imidazol-5-yl)methyl]benzonitrile (0.001 mol), obtained in stage a), iodomethane (0.0011 mol) and benzyltriethylammonium chloride (0.0001 mol) in THF (12 ml) and sodium hydroxide (12 ml) was stirred at room temperature for 3 hours, poured out into ice water and extracted with EtOAc. The organic layer was separated, dried ($MgSO_4$), filtered and the solvent was evaporated. The residue (0.79 g) was purified by column chromatography over silica gel (eluent: $CH_2Cl_2/CH_3OH/NH_4OH$ 95/5/0.1; 15–40 μm). One fraction was collected and the solvent was evaporated This fraction (0.5 g) was crystallized from diethyl ether. The precipitate was filtered off and dried, yielding 0.47 g (70%) of (±)-4-[[4-(3-chlorophenyl)-1,2-dihydro-1-methyl-2-oxo-6-quinolinyl]hydroxy(1-methyl-1H-imidazol-5yl)methyl]benzonitrile, mp. 210° C.

c) A mixture of (±)-4-[[4-(3-chlorophenyl)-1,2-dihydro-1-methyl-2-oxo-6-quinolinyl]hydroxy(1-methyl-1H-imidazol-5yl)methyl]benzonitrile (0.00121 mol), obtained in stage b), in thionyl chloride (6 ml) was stirred at room temperature for 2 hours. The solvent was evaporated. The residue was taken up in DCM. The solvent was evaporated till dryness, yielding 4-[chloro[4-(3-chlorophenyl)-1,2-dihydro-1-methyl-2-oxo-6-quinolinyl](1-methyl-1H-imidazol-5-yl)methyl]-benzonitrile. The product was used without further purification in the next reaction step d) $NH_3$/iPrOH (6 ml) was added dropwise at 5° C. to a solution of 4-[chloro[4-(3-chlorophenyl)-1,2-dihydro-1-methyl-2-oxo-6-quinolinyl](1-methyl-1H-imidazol-5-yl)methyl]-benzonitrile (0.00121 mol), (obtained in stage c), in THF (7 ml). The mixture was stirred at room temperature for 4 hours, poured out into water and extracted with EtOAc. The organic layer was separated, dried ($MgSO_4$), filtered, and the solvent was evaporated. The residue was purified by column chromatography over silica gel (eluent: toluene/iPrOH/$NH_4OH$; 90/10/1; 15–40 μm). The pure fractions were collected and the solvent was evaporated, yielding 0.3 g (52%) which were then purified by column chromatography over kromasil (eluent: $CH_3CN/NH_4OAc$; 40/60; 15–40 μm). The pure fractions were collected and the solvent was evaporated, yielding 0.18 g (31%) which were crystallized from $CH_3CN$/diethyl ether. The precipitate was filtered off and dried, yielding 0.13 g (22%) of 4-[amino[4-(3-chlorophenyl)-1,2-dihydro-1-methyl-2-oxo-6quinolinyl](1-methyl-1H-imidazol-5-yl)methyl]-benzonitrile, melting point 245° C.

e) Raney nickel (0.55 g) was added to a mixture of 4-[amino[4-(3-chlorophenyl)-1,2-dihydro-1-methyl-2-oxo-6-quinolinyl](1-methyl-1H-imidazol-5-yl)methyl]-benzonitrile, (0.0011 mol) in $CH_3OH/NH_3$ 7N (12 ml) under $N_2$ flow. The mixture was hydrogenated overnight under a 5 bar pressure, then filtered over celite. The filtrate was evaporated. The residue was purified by column chromatography over silica gel (eluent: $CH_2Cl_2/CH_3OH/NH_4OH$ 92/8/0.5; 15–40 μm). The pure fractions were collected and the solvent was evaporated, yielding 0.36 g (65%)g of 6-[amino[4-(aminomethyl)phenyl](1-methyl-1H-imidazol-5-yl)methyl]-4-(3-chlorophenyl)-1-methyl-2(1H)-quinolinone, mp. 150° C.

EXAMPLE B42

A mixture of intermediate (72) (0.00008 mol), obtained in Example A14, in HCl 6N (1 ml) was stirred and refluxed for 18 hours, then cooled, poured out into water, basified with potassium carbonate 10% and extracted with EtOAc. The organic layer was separated, dried ($MgSO_4$), filtered, and the solvent was evaporated. The residue was crystallized from $CH_3CN$/diethyl ether. The precipitate was filtered off and dried, yielding 0.028 g (63%) of 6-[(4amino-3-pyridinyl)(4-chlorophenyl)hydroxymethyl]-4-(3-chlorophenyl)-1-methyl-2(1H)-quinolinone, mp. 262° C.

EXAMPLE B43

BuLi (0.0023 mol) was added dropwise at −75° C. to a mixture of 3-bromo-4-methyl-pyridine (0.0023 mol) in diethyl ether (8 ml) under $N_2$ flow. The mixture was stirred for 45 minutes. A solution of 6-(4-chlorobenzoyl)-4-(3-chlorophenyl)-1-methyl-2(1H)-quinolinone (0.0019 mol), described in International Patent Specification WO 97/21701, in THF (8 ml) was added at −75° C. The mixture was stirred at room temperature for 18 hours. Water was added. The mixture was extracted with EtOAc. The organic layer was separated, dried ($MgSO_4$), filtered, and the solvent was evaporated. The residue (0.9 g) was purified by column chromatography over silica gel (eluent: $CH_2Cl_2/CH_3OH/NH_4OH$ 96/4/0.2; 15–40 μm). The pure fractions were collected and the solvent was evaporated, yielding 0.16 g (16%) of fraction F1. F1 was purified by column chromatography over C18 silica gel (eluent: $CH_3CN/AcNH_4$ 60/40; 15–40 μm). The pure fractions were collected and the solvent was evaporated, yielding 0.056 g (6%) of 4-(3-chlorophenyl)-6-[(4-chlorophenyl)hydroxy(4-methyl-3-pyridinyl)methyl]-1-methyl-2(1H)-quinolinone, MS (ESI) m/z: 501, 503, 505 (MH$^+$).

EXAMPLE B44

Triethylamine (0.0006 mol) then methanesulfonyl chloride (0.0004 mol) were added dropwise at 5° C. to a mixture of 6-[amino[4(aminomethyl)phenyl](1-methyl-1H-imidazol-5-yl)methyl]-4-(3-chlorophenyl)-1-methyl-2(1H)-quinolinone (0.0004 mol), obtained in Example B41, in DCM (4 ml) under $N_2$ flow. The mixture was stirred at 5° C. for 1 hour, poured out into ice water and extracted with DCM. The organic layer was separated, dried ($MgSO_4$), filtered, and the solvent was evaporated. The residue was purified by column chromatography over kromasyl (eluent: $CH_2Cl_2/CH_3OH/NH_4OH$ 95/5/0.5; 15–40 μm). The pure fractions were collected and the solvent was evaporated. The residue (0.1 g, 43%) was crystallized from $CH_3CN$/diethyl ether. The precipitate was filtered off and dried, yielding 0.02 g (8.6%) of N-[[-4-amino[4-(3-chlorophenyl)-1,2-dihydro-1-methyl-2-oxo-6-quinolinyl](1-methyl-1H-imidazol-5-yl)methyl]phenyl]methyl]-methanesulfonamide, mp. 140° C.

EXAMPLE B45 a) A mixture of intermediate (76) (0.0051 mol), obtained in Example A15d, Pd(OAc)$_2$ (0.0005 mol), PPh$_3$ (0.0077 mol) and potassium carbonate (0.01 mol) in 2-propanol (12 ml) and DMF (14 ml) was stirred at 90° C. overnight under a 5 bar pressure of CO, then brought to room temperature and poured out into ice water. EtOAc was added. The mixture was filtered over celite. The celite was washed with EtOAc. The filtrate was extracted with EtOAc. The organic layer was separated, washed with water, dried (MgSO$_4$), filtered and the solvent was evaporated. The residue was purified by column chromatography over silica gel (eluent: $CH_2Cl_2/CH_3OH/NH_4OH$ 9/37/0.1; 15–40 μm). The pure fractions were collected and the solvent was evaporated, yielding 1.4 g (50%) of residue. Part of this residue (0.5 g) was washed with diethyl ether. The precipitate was filtered off and dried, yielding 0.35 g of 1-methylethyl 3-[[4-(3-chlorophenyl)-1,2-dihydro-1-methyl-2-oxo-6-quinolinyl]hydroxy(1-methyl-1H-imidazol-5-yl)methyl]-benzoate, melting point 150° C.

b) A solution of 1-methylethyl 3-[[4(3-chlorophenyl)-1,2-dihydro-1-methyl-2-oxo-6-quinolinyl]hydroxy(1-methyl-1H-imidazol-5-yl)methyl]-benzoate (0.0059 mol), obtained in stage a), in THF (30 ml) was added dropwise at 5° C. to a mixture of LiAlH$_4$ (0.00001 mol) in THF (5 ml) under $N_2$ flow. The mixture was stirred at 5° C. for 1 hour, then at room temperature for 3 hours and cooled. EtOAc was added dropwise. The mixture was poured out slowly into water, then filtered over celite. The celite was washed with EtOAc. The filtrate was extracted with EtOAc. The organic layer was separated, washed with water, dried (MgSO$_4$) filtered and the solvent was evaporated. The residue was purified by column chromatography over silica gel (eluent: $CH_2Cl_2/CH_3OH/NH_4OH$ 95/5/0.2; 15–40 μm). The pure fractions were collected and the solvent was evaporated, yielding 0.88 g (30%) of 4-(3-chlorophenyl)-6-[hydroxy[3-(hydroxymethyl)phenyl](1-methyl-1H-imidazol-5-yl)methyl]-1-methyl-2(1H)-quinolinone, which were crystallized from 2-propanone/diethyl ether. The precipitate was filtered off and dried in a vacuo, yielding 0.8 g (28%) of 4-(3-chlorophenyl)-6-[hydroxy[3-(hydroxymethyl)phenyl](1-methyl-1H-imidazo-1-5-yl)methyl]-1-methyl-2(1H)-quinolinone, mp. 150° C.

EXAMPLE B46

NaBH$_4$ (0.0002 mol) was added portionwise at room temperature to a mixture of 5-(3-chlorophenyl)-α-(4-iodophenyl)-α-(4-methyl-4H-1,2,4-triazol-3-yl)-tetrazolo[1,5-a]quinazoline-7-methanol, (0.0002 mol), obtained in Example B29a, in methanol (1.5 ml). The mixture was stirred at room temperature for 2 hours and poured out into ice water. DCM was added. The mixture was extracted with DCM. The organic layer was washed with water, separated, dried (MgSO$_4$), filtered, and the solvent was evaporated, yielding 0.13 g (81%) of fraction F1. This fraction was taken up in diethyl ether. The precipitate was filtered off and dried in a vacuum, yielding 0.1 g (63%) of 5-(3-chlorophenyl)-4,5-dihydro-α-(4-iodophenyl)-α-(4-methyl-4H-1,2,4-triazol-3-yl)-tetrazolo[1,5-a]quinazoline-7-methanol, mp. 201° C.

The following compounds were prepared analogous to one of the above examples (the example number analogous to which they were prepared is indicated between square brackets).

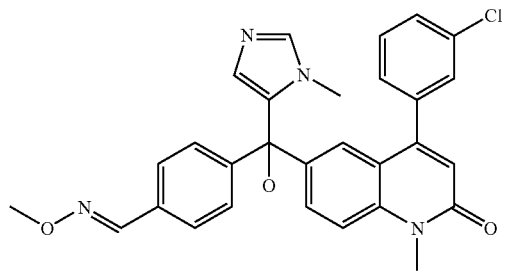
[B2], mp. 169° C.
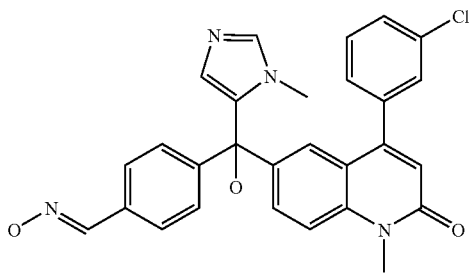
[B2], mp. 266° C.
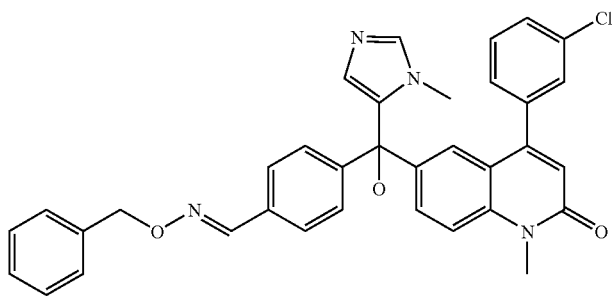
[B2], mp. 200° C.
[B11] ms. 647 649
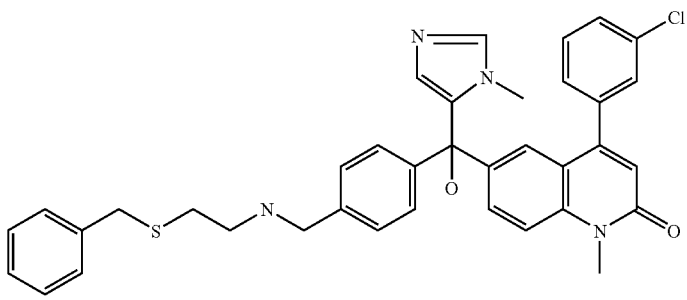
[B11] ms. 635 637
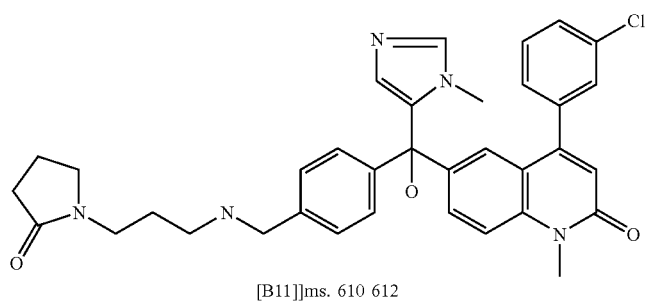
[B11]]ms. 610 612

-continued
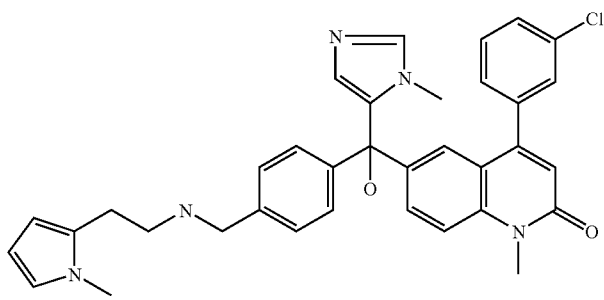
[B11] ms. 592 594
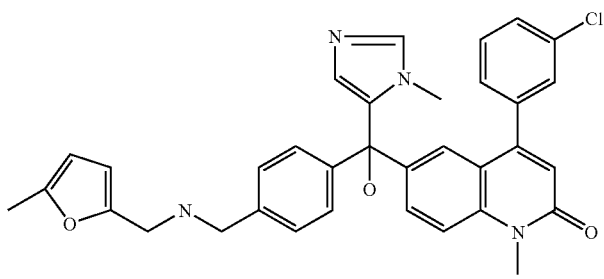
[B11] ms. 579 581
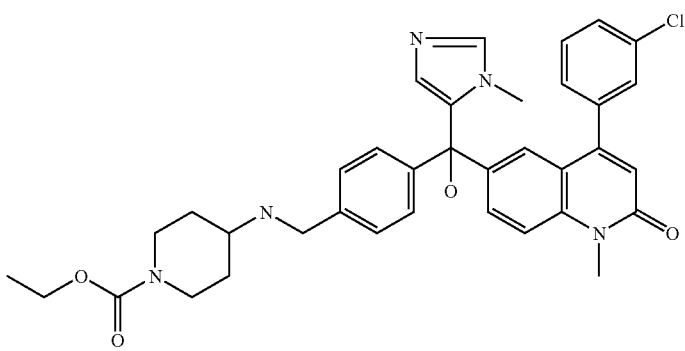
[B11] ms. 640 642
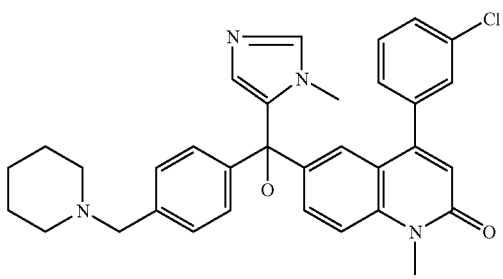
[B11] ms. 553 555
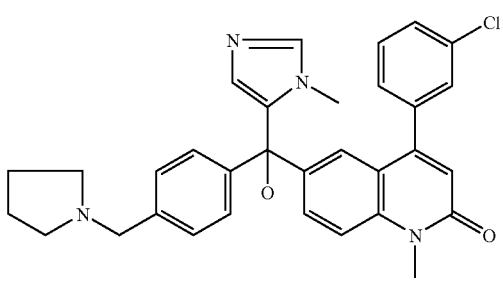
[B11] ms. 539 541

-continued
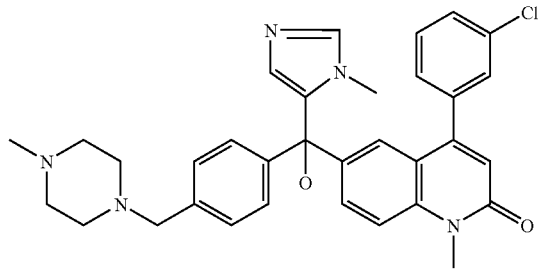
[B11] ms. 568 570
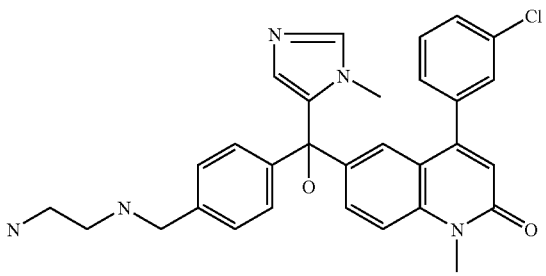
[B11] ms. 528 530
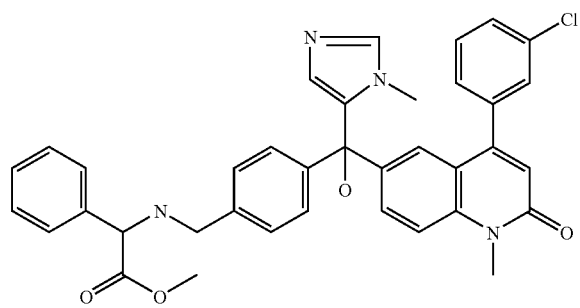
[B11] ms. 633 635
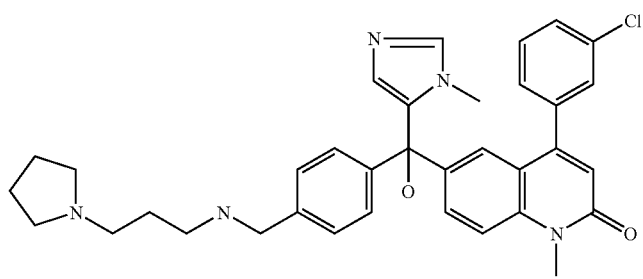
[B11] ms. 596 598
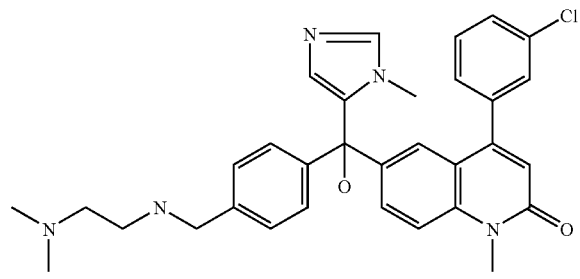
[B11] ms. 556 558

-continued
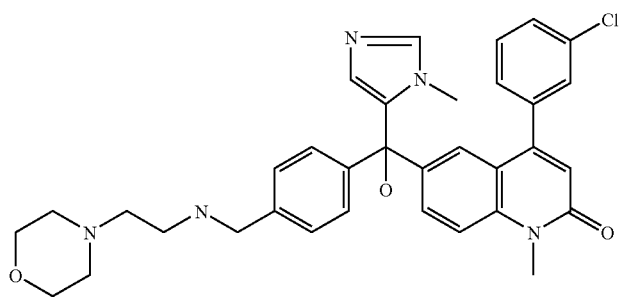
[B11] ms. 596 600
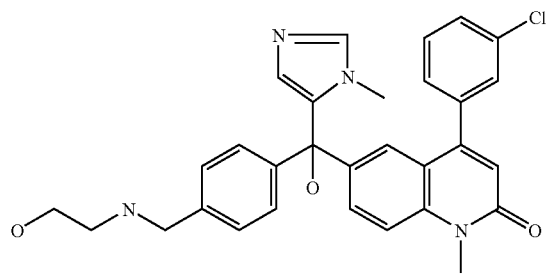
[B11] ms. 529 531
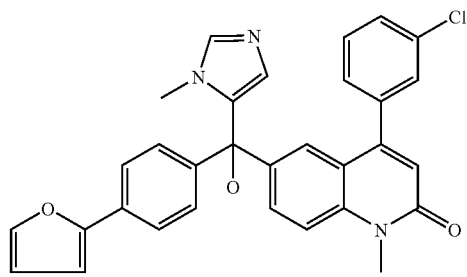
[B10], mp. 182° C.
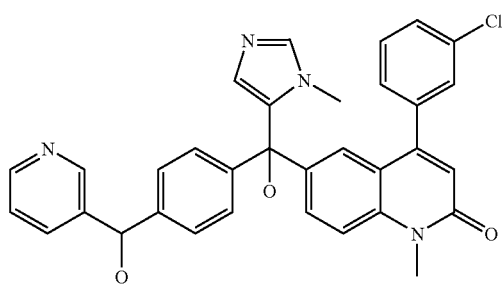
[B17] ms. 563 564
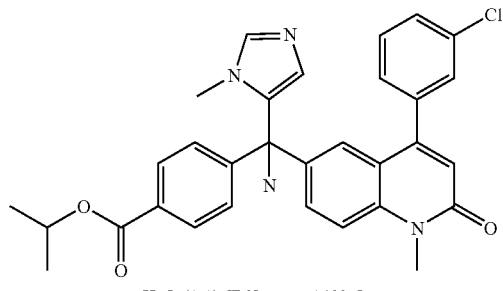
H₂O (1:1) [B8], mp. 140° C.

-continued
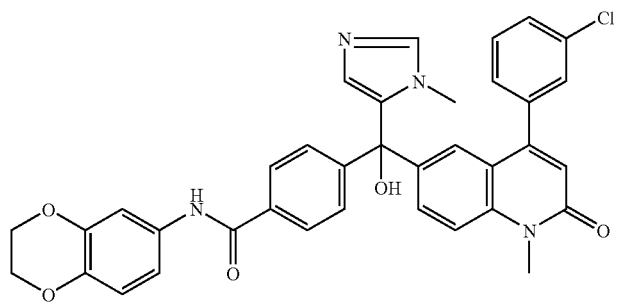
[B21] ms. 633 635
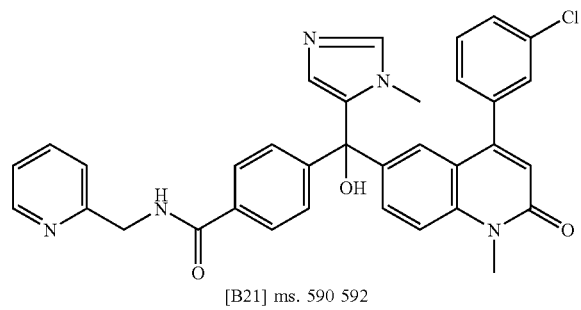
[B21] ms. 590 592
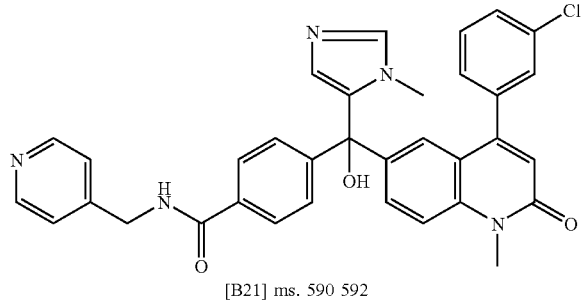
[B21] ms. 590 592
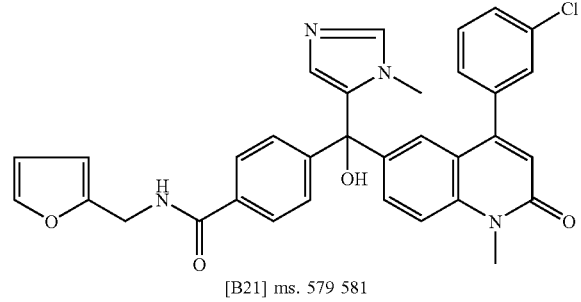
[B21] ms. 579 581
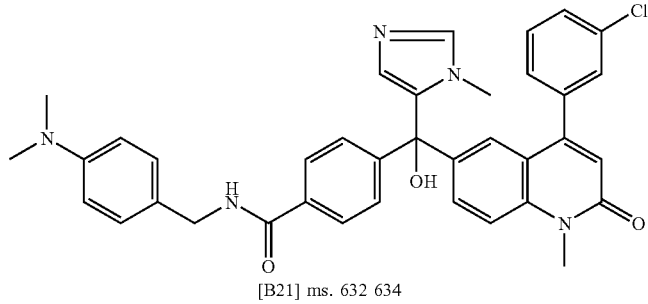
[B21] ms. 632 634

-continued
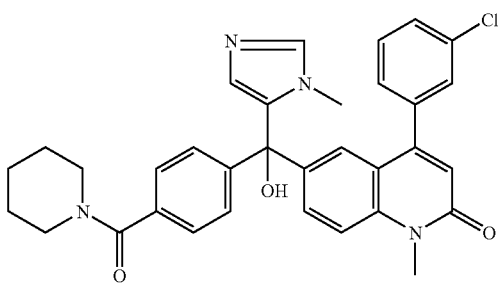
[B21] ms. 567 579
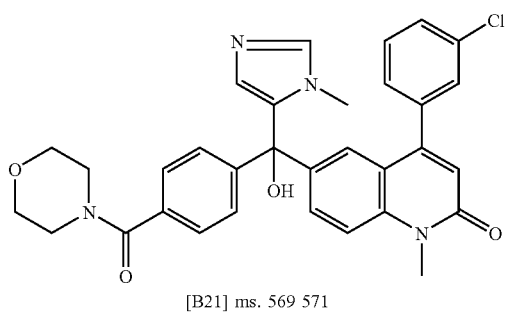
[B21] ms. 569 571
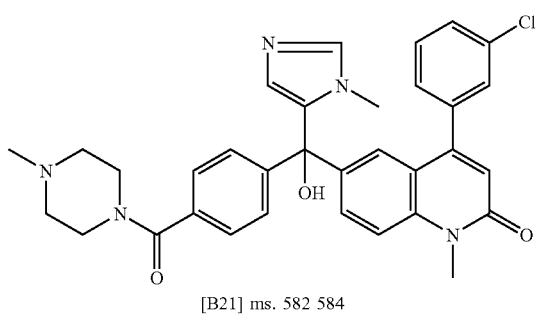
[B21] ms. 582 584
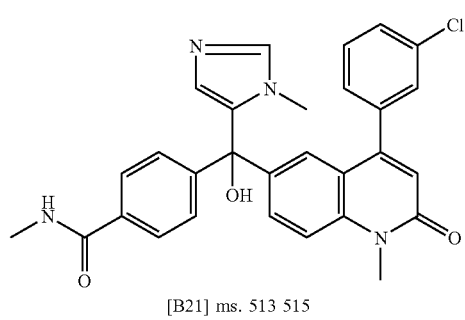
[B21] ms. 513 515
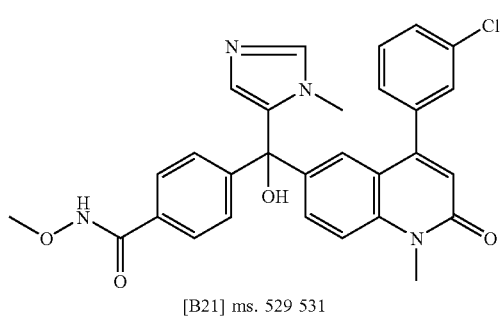
[B21] ms. 529 531

-continued
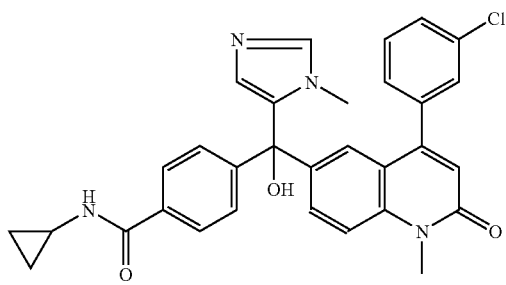
[B21] ms. 539 541
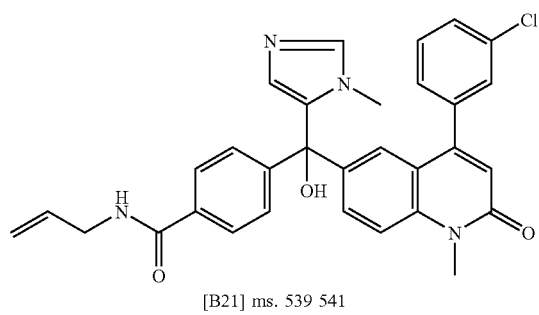
[B21] ms. 539 541
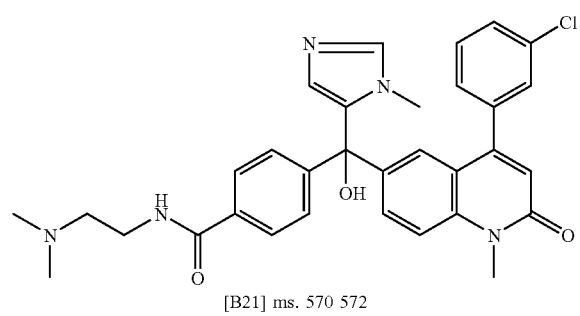
[B21] ms. 570 572
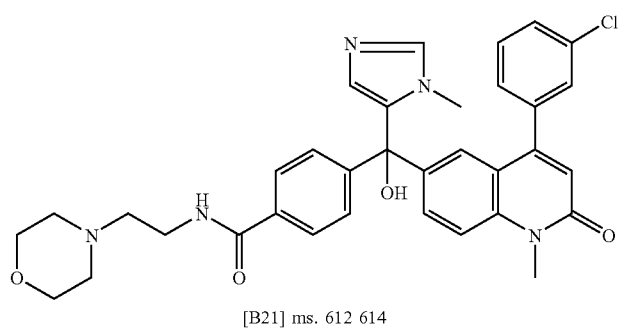
[B21] ms. 612 614
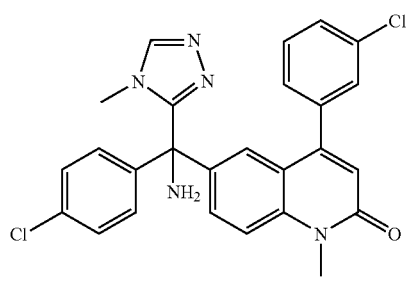
[B8] mp. 210° C.

-continued
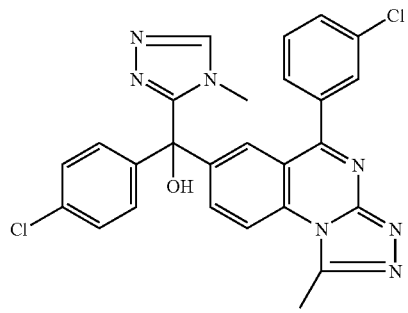
[B20], mp. 220° C.
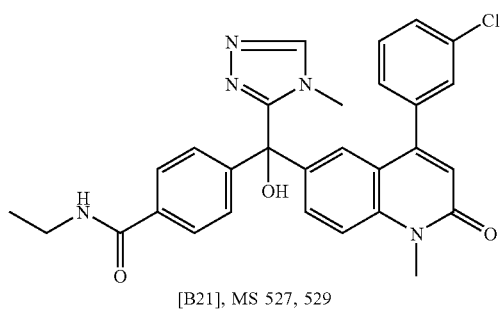
[B21], MS 527, 529
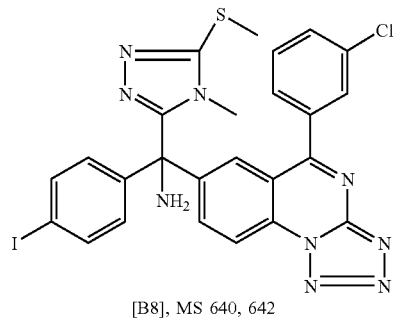
[B8], MS 640, 642
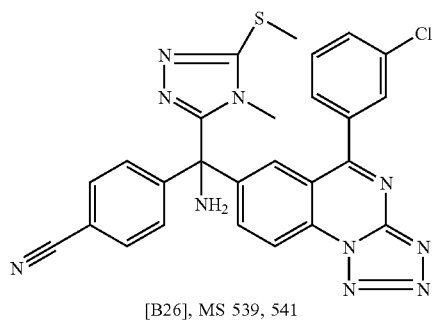
[B26], MS 539, 541
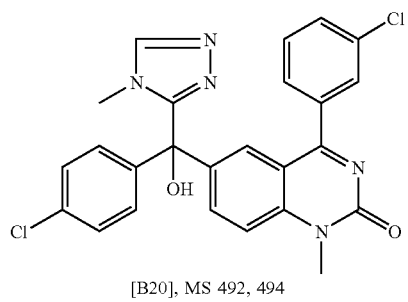
[B20], MS 492, 494

-continued
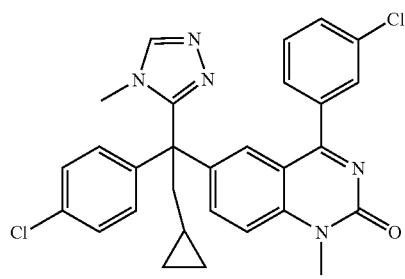
[B31], mp. 125° C.
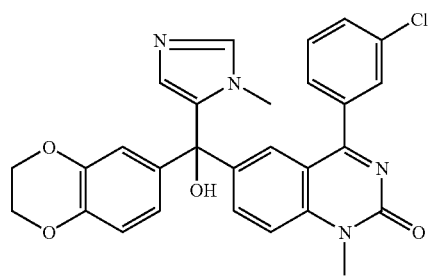
[B6], MS 515, 517
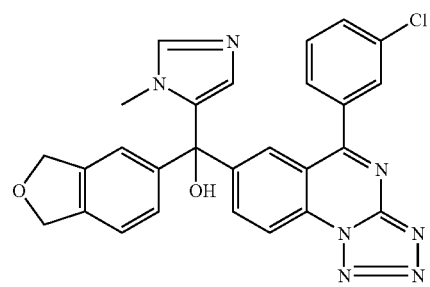
[B36], mp. 190° C.
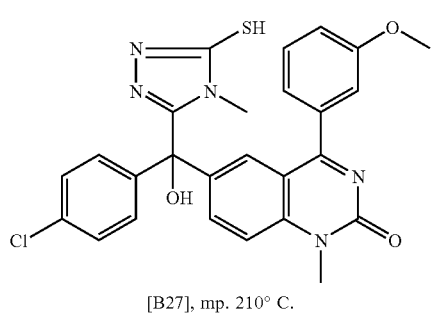
[B27], mp. 210° C.
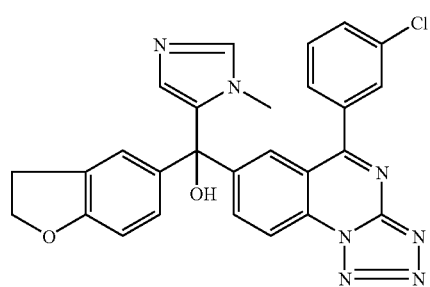
[B36], mp. 235° C.

-continued
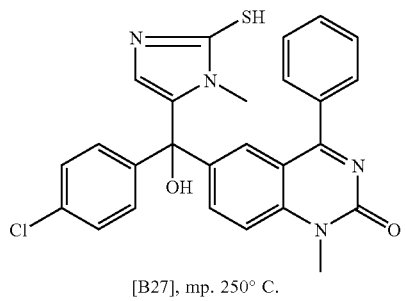
[B27], mp. 250° C.
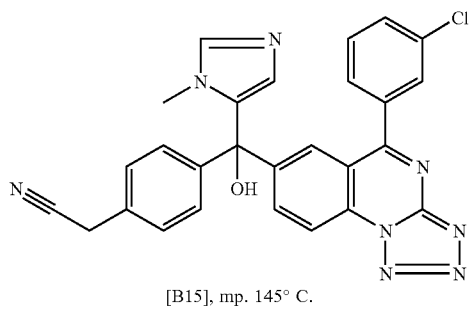
[B15], mp. 145° C.
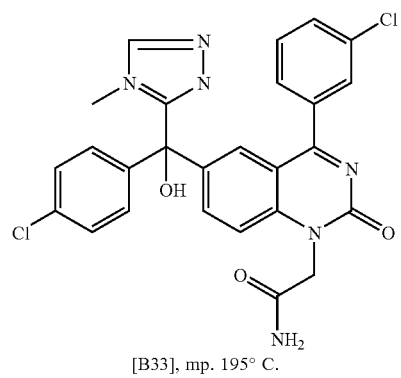
[B33], mp. 195° C.
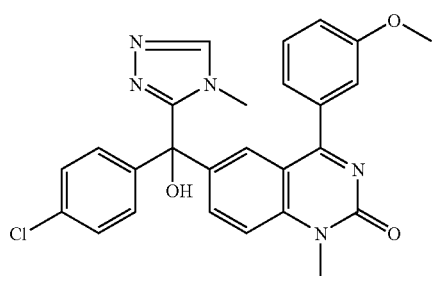
[B20], mp. 173° C.
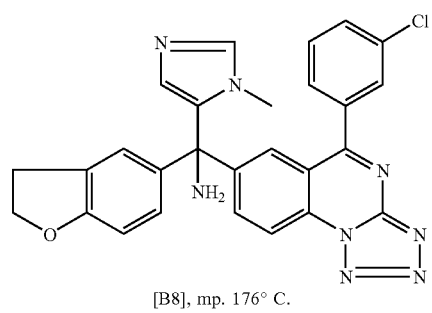
[B8], mp. 176° C.

-continued
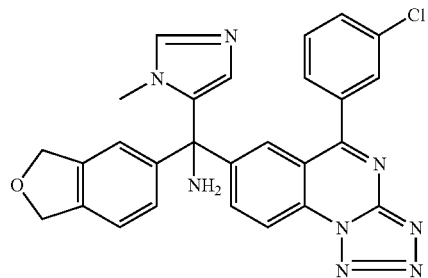
[B8], MS 509, 511
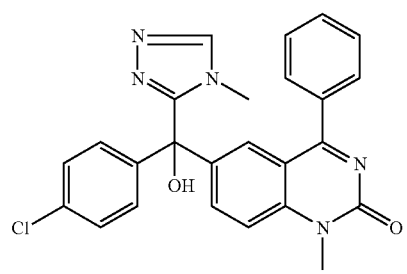
[B20], mp. 174° C.
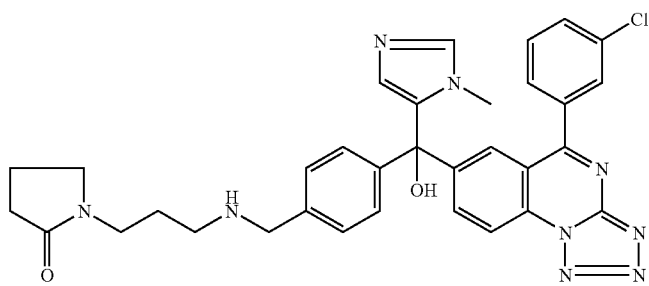
[B11], MS 622, 624
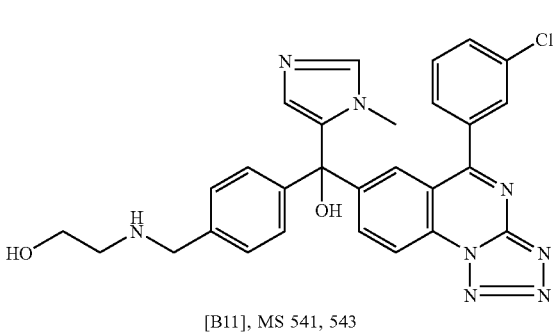
[B11], MS 541, 543
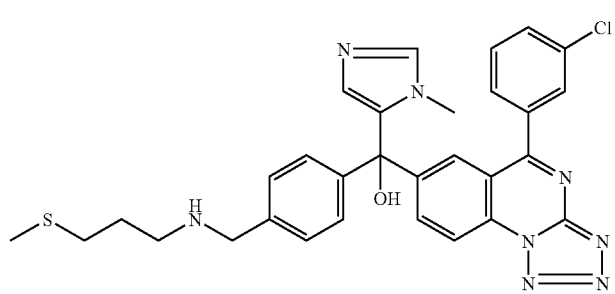
[B11], MS 585, 587

-continued
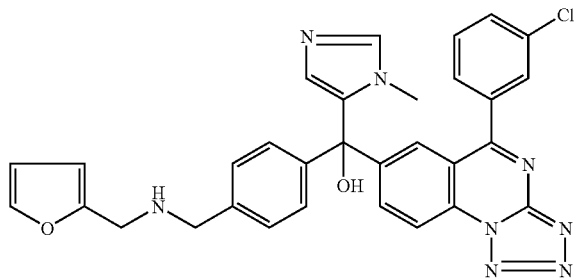
[B11], MS 577, 579
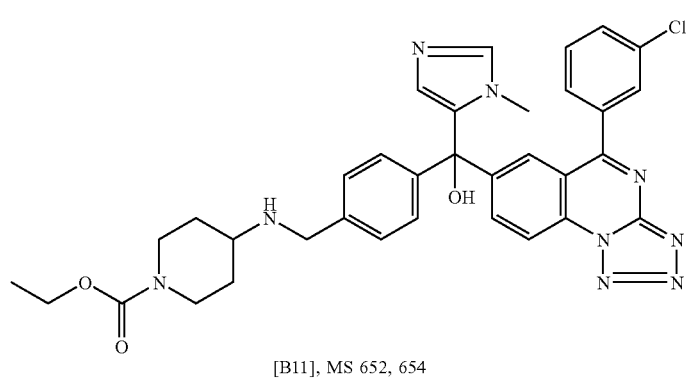
[B11], MS 652, 654
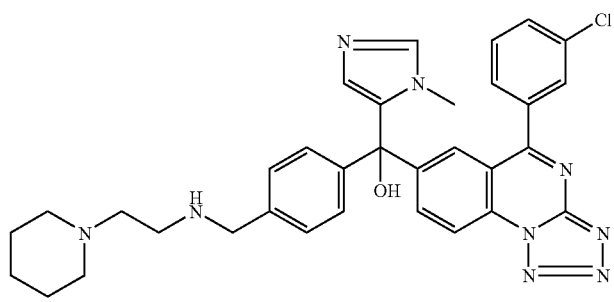
[B11], MS 608, 610
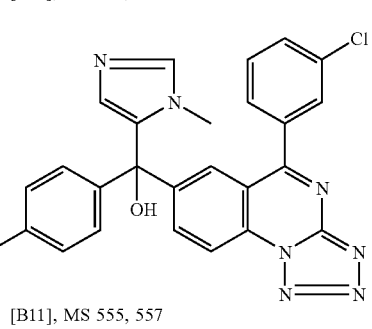
[B11], MS 555, 557
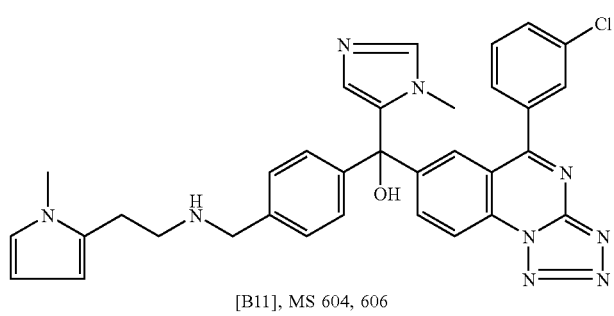
[B11], MS 604, 606

-continued
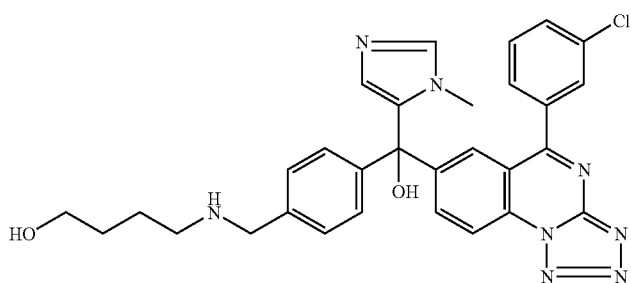
[B11], MS 569, 571
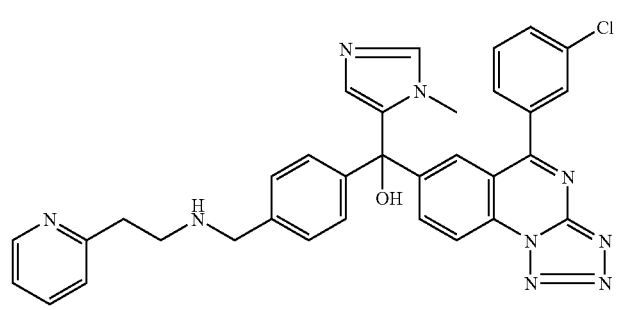
[B11], MS 602, 604
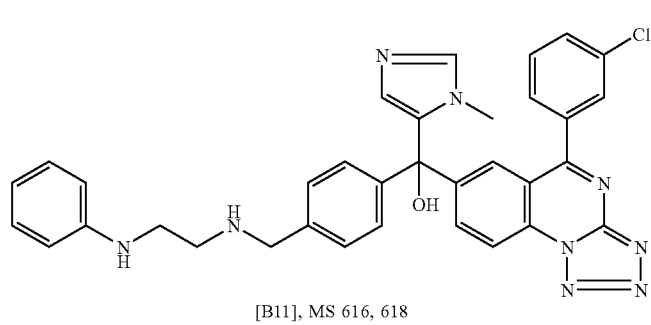
[B11], MS 616, 618
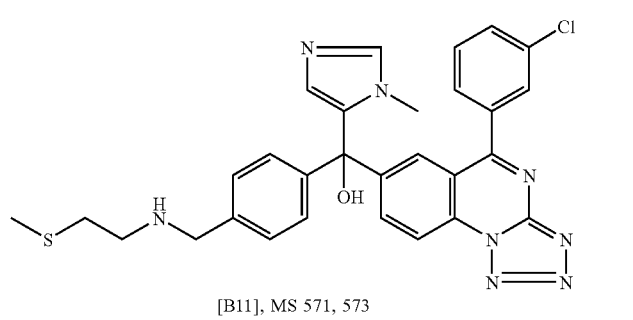
[B11], MS 571, 573
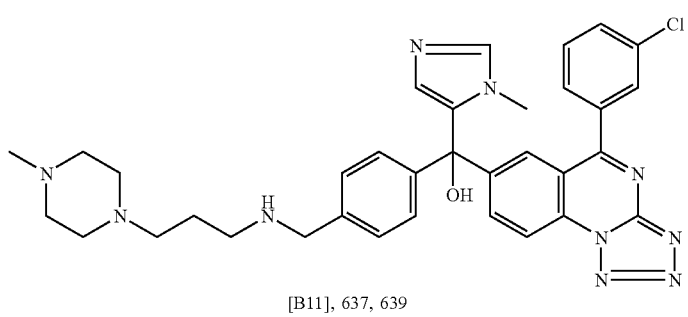
[B11], 637, 639

-continued
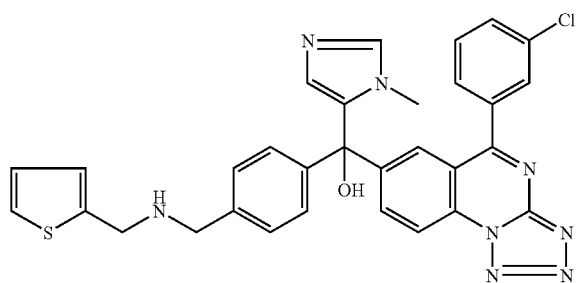
[B11], MS 593, 595
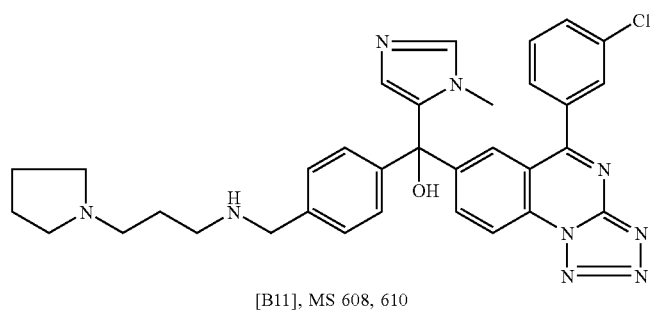
[B11], MS 608, 610
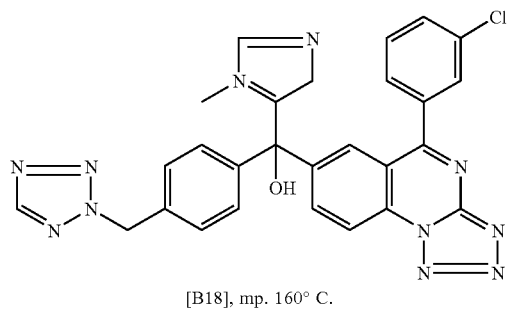
[B18], mp. 160° C.
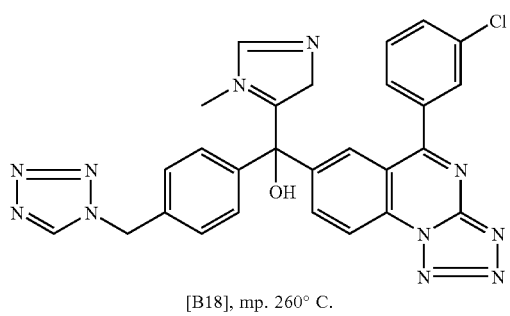
[B18], mp. 260° C.
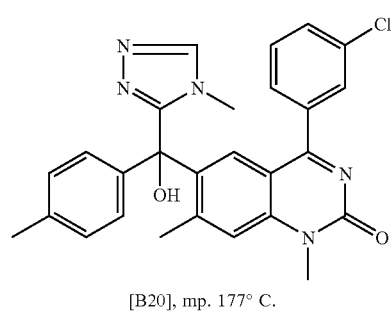
[B20], mp. 177° C.

-continued
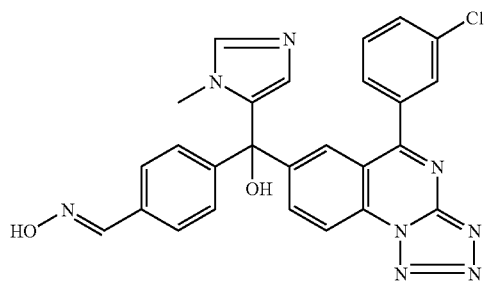
[B2], (E), mp. 130° C.
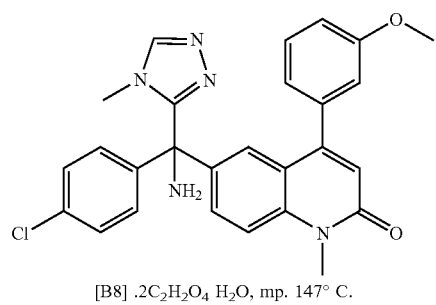
[B8] .2C₂H₂O₄ H₂O, mp. 147° C.
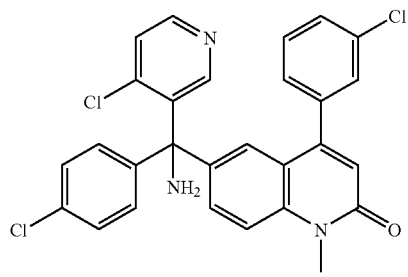
[B8], mp. 180° C.
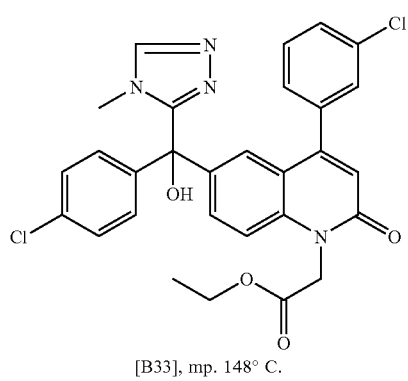
[B33], mp. 148° C.
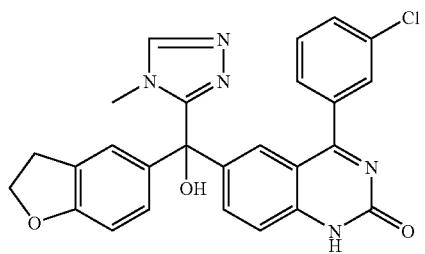
[B30], mp. 215° C.

-continued
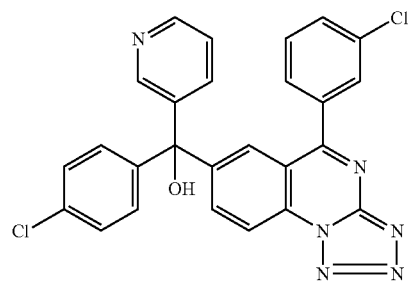
[B36], mp. 140° C.
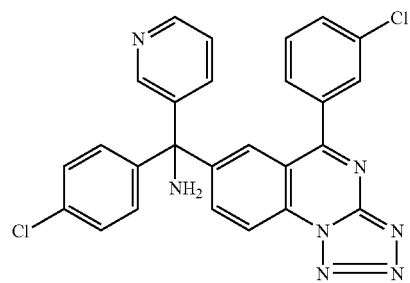
[B8], MS 498, 500, 502
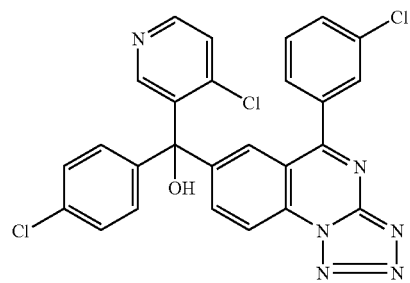
[B39], MS 533, 535, 537, 539
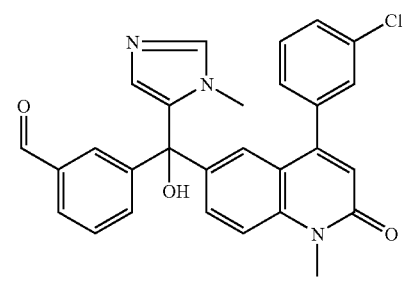
[B38], .H$_2$O mp. 150° C.
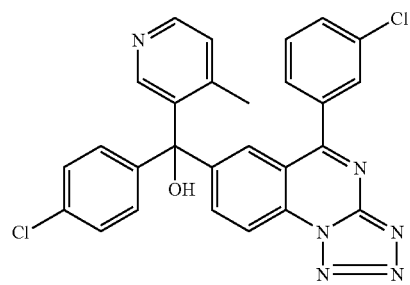
[B36], mp. 155° C.

-continued
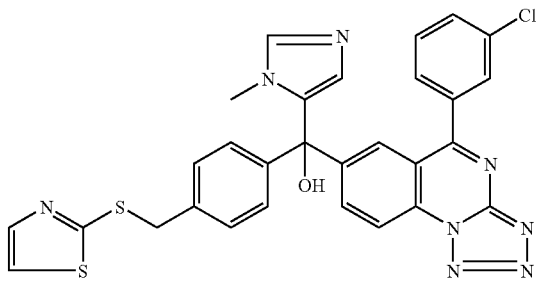
[B25], mp. 140° C.
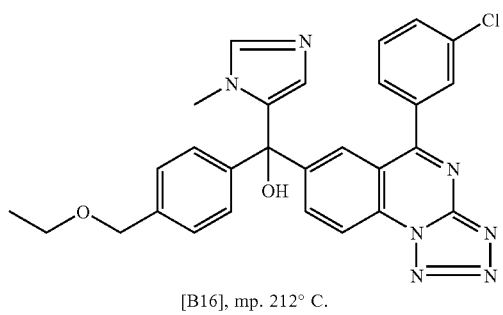
[B16], mp. 212° C.
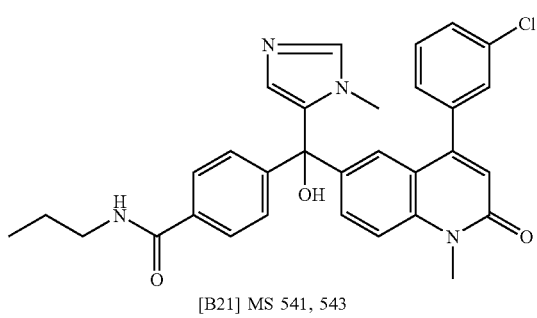
[B21] MS 541, 543
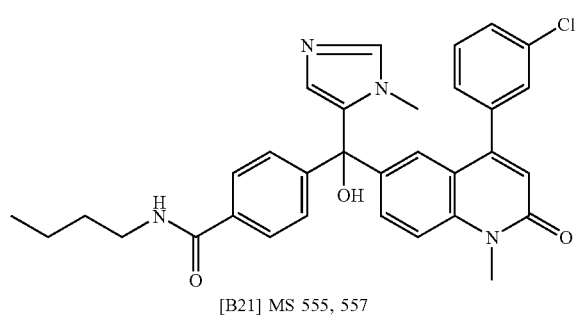
[B21] MS 555, 557
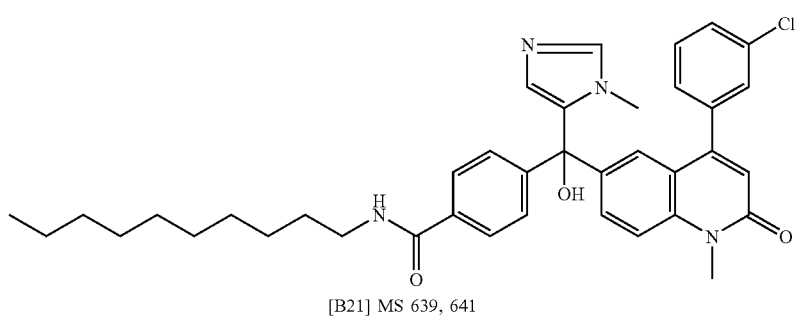
[B21] MS 639, 641

-continued
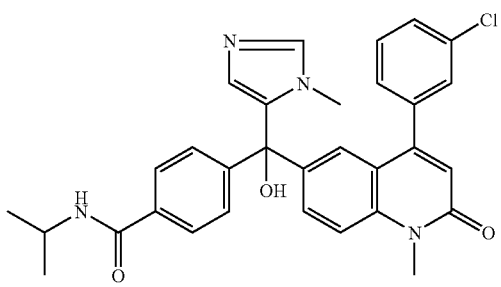
[B21] MS 541, 543
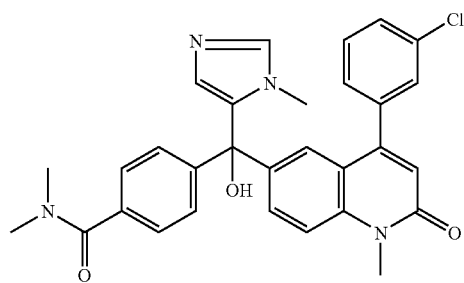
[B21] MS 527, 529
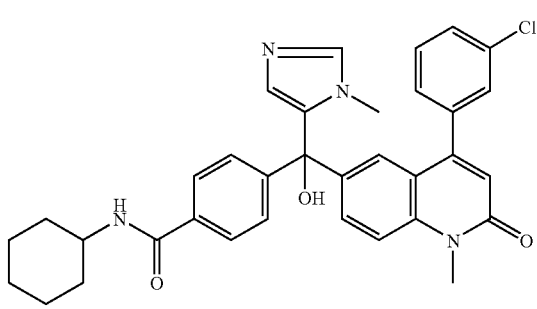
[B21] MS 581, 583
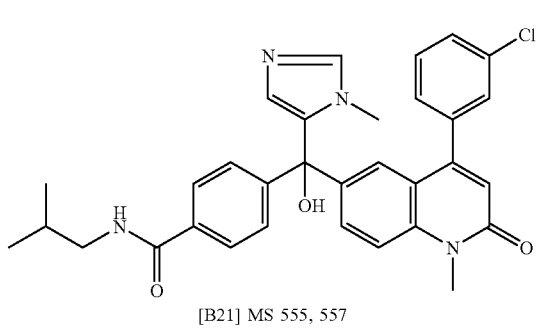
[B21] MS 555, 557
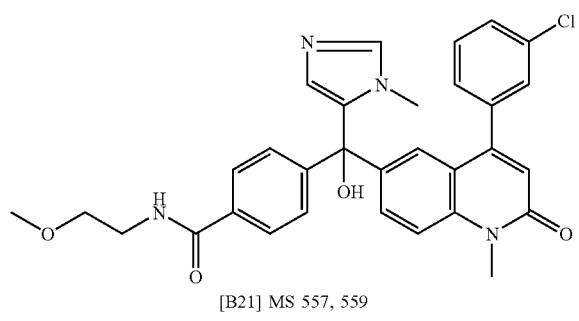
[B21] MS 557, 559

-continued
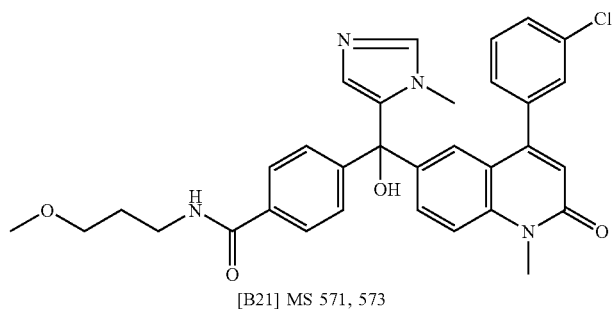
[B21] MS 571, 573
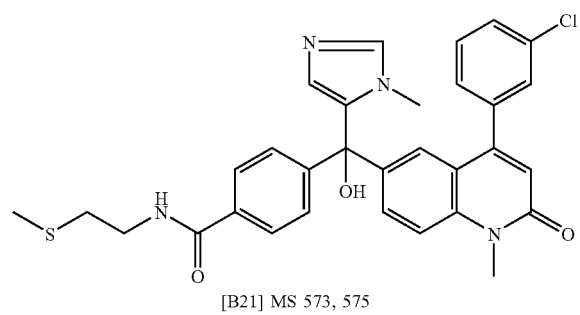
[B21] MS 573, 575
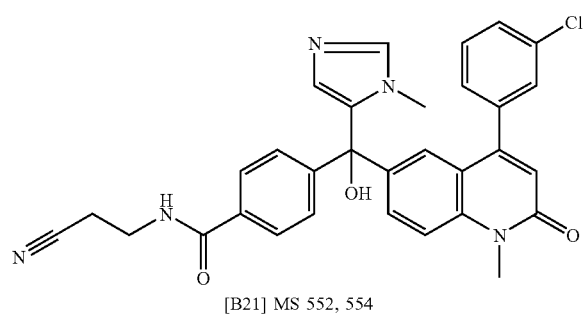
[B21] MS 552, 554
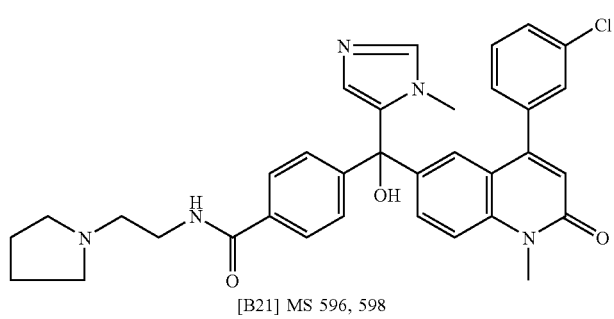
[B21] MS 596, 598
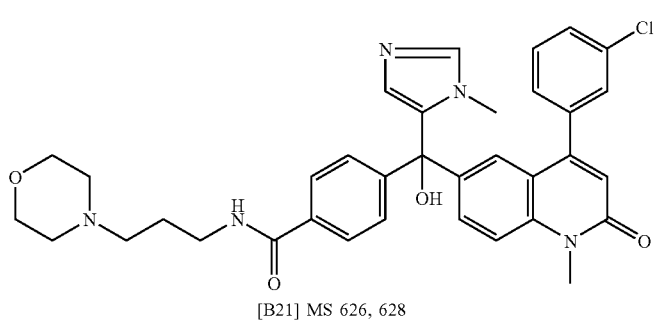
[B21] MS 626, 628

-continued
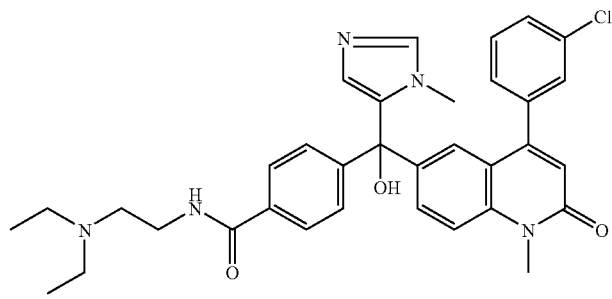
[B21] MS 598, 600
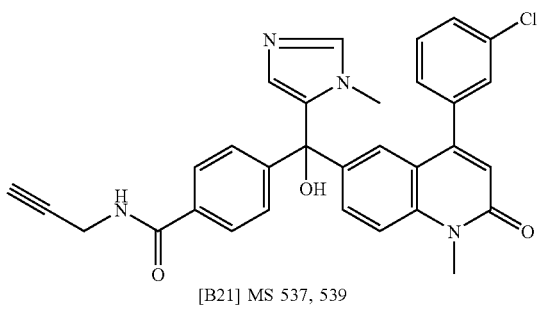
[B21] MS 537, 539
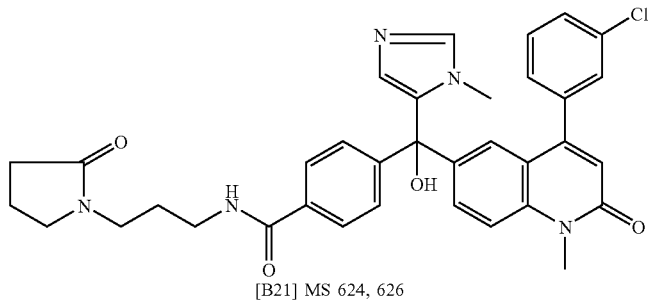
[B21] MS 624, 626
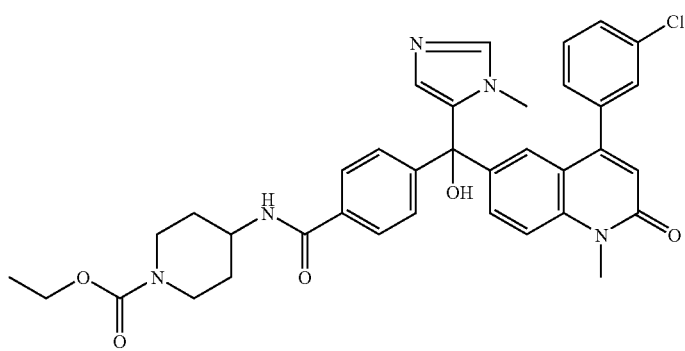
[B21] MS 654, 656
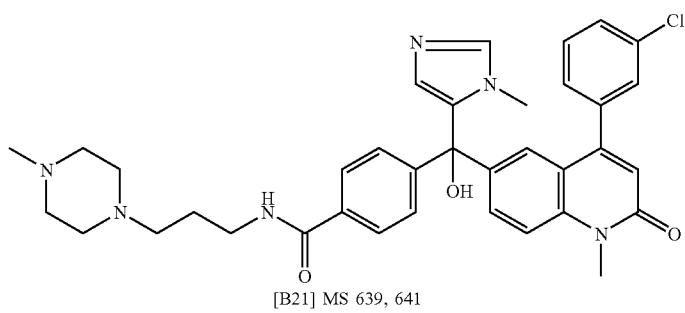
[B21] MS 639, 641

-continued
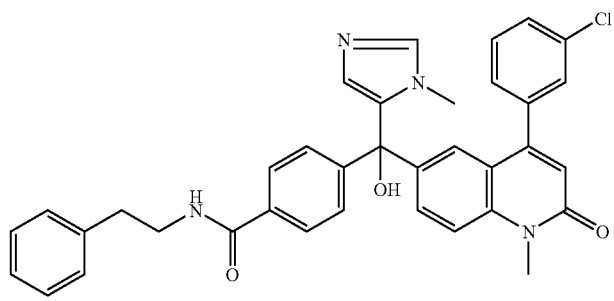
[B21] MS 603, 605
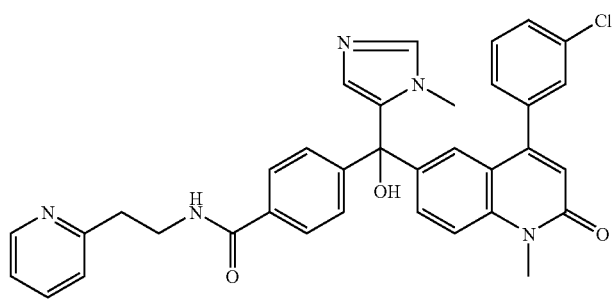
[B21] MS 604, 606
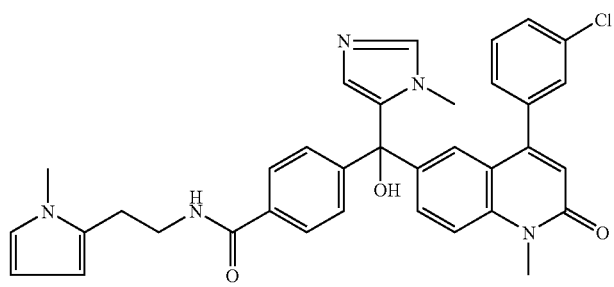
[B21] MS 606, 608
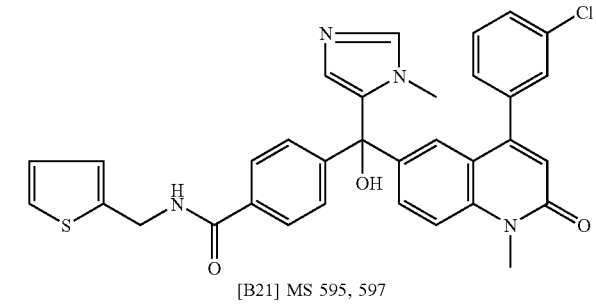
[B21] MS 595, 597
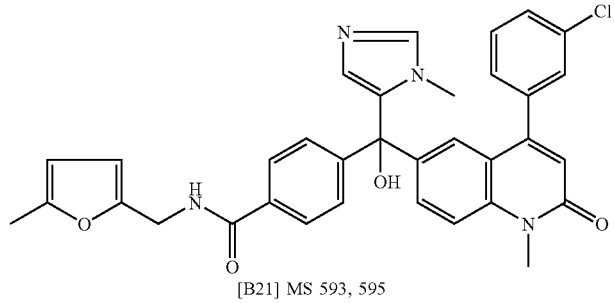
[B21] MS 593, 595

-continued
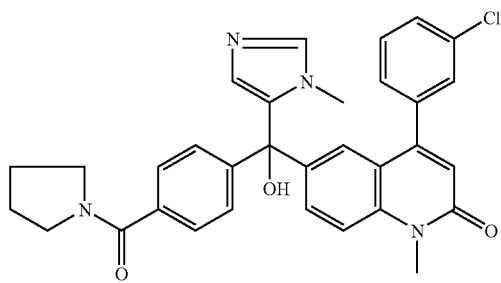
[B21] MS 553, 555
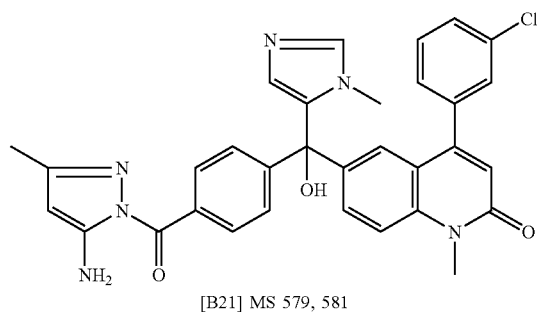
[B21] MS 579, 581
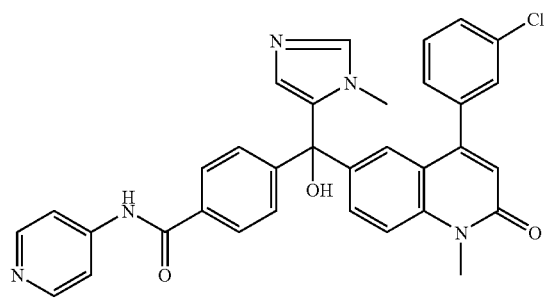
[B21] MS 576, 578
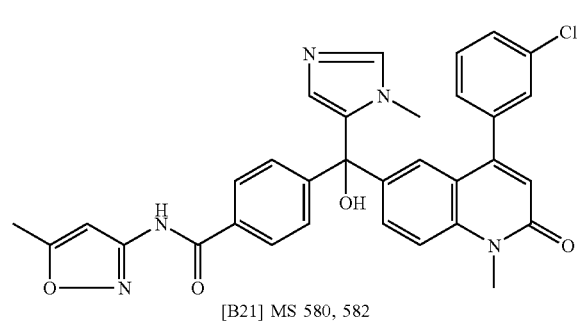
[B21] MS 580, 582
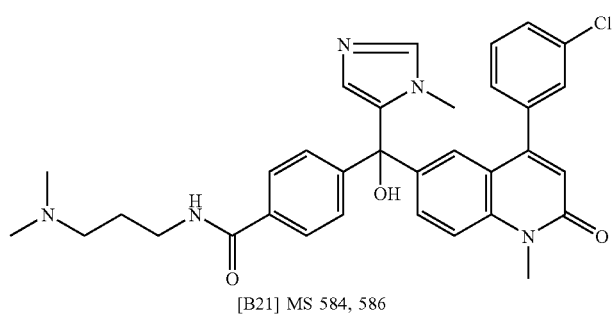
[B21] MS 584, 586

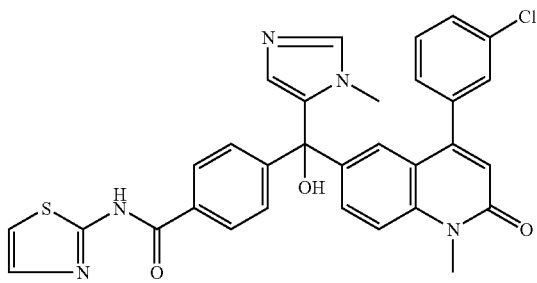
[B21] MS 582, 584
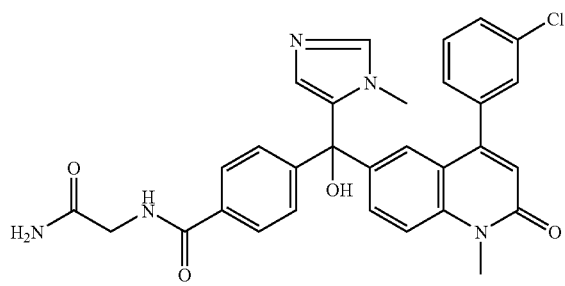
[B21] MS 556, 558
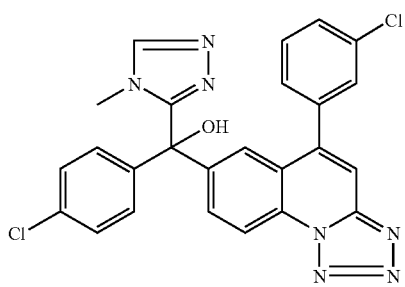
[B13] mp. 199° C.
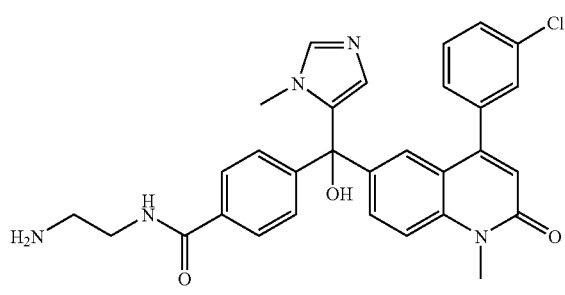
[B21] MS 542, 544
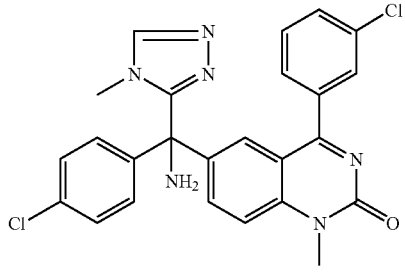
[B22] mp. 135° C.

-continued
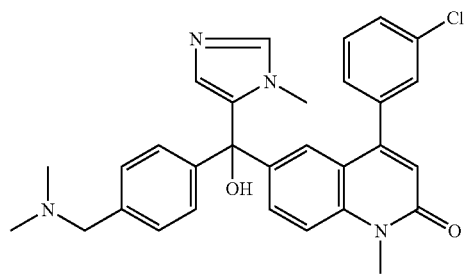
[B37] MS 513, 515
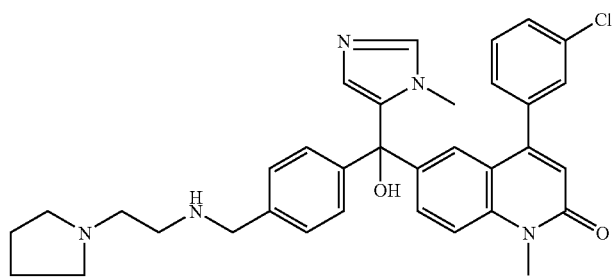
[B37] MS 582, 584
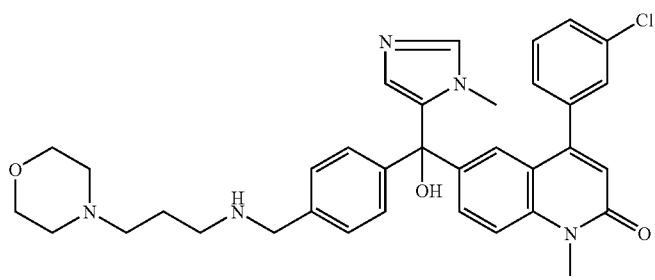
[B37] MS 612, 614
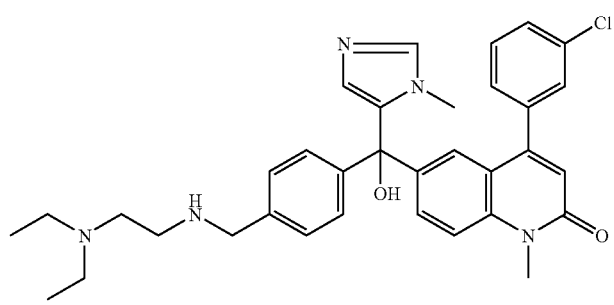
[B37] MS 584, 586
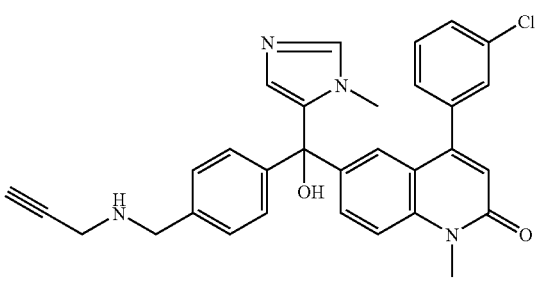
[B37] MS 523, 525

-continued
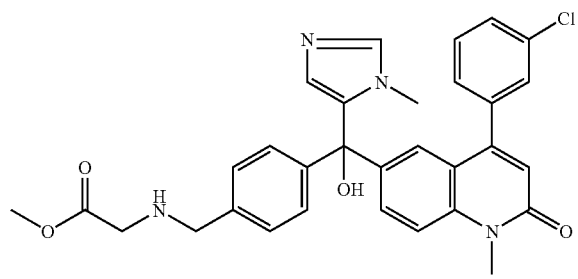
[B37] MS 557, 559
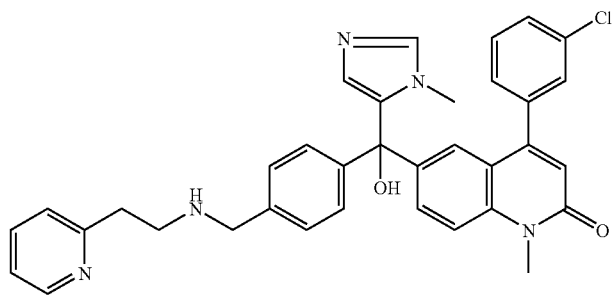
[B37] MS 590, 592
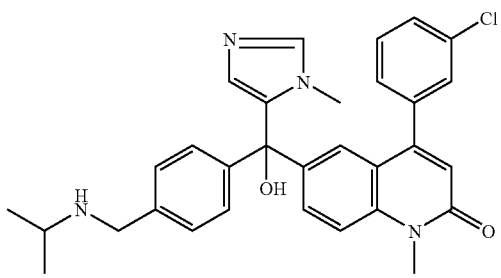
[B37] MS 527, 529
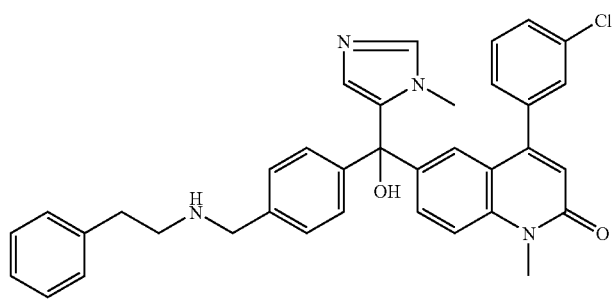
[B37] MS 589, 591
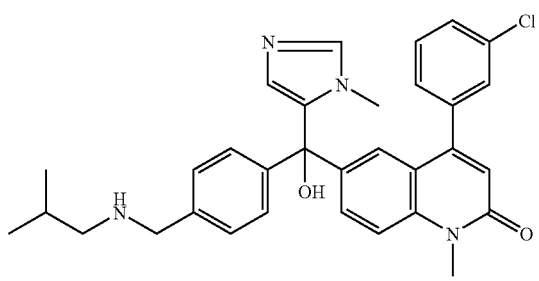
[B37] MS 541, 543

-continued
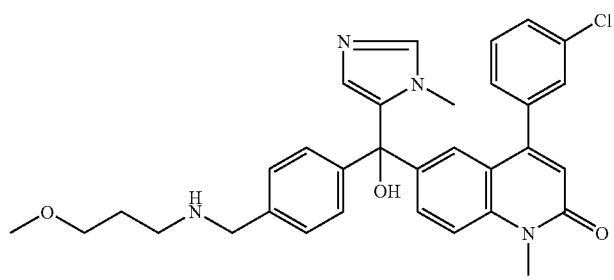
[B37] MS 557, 559
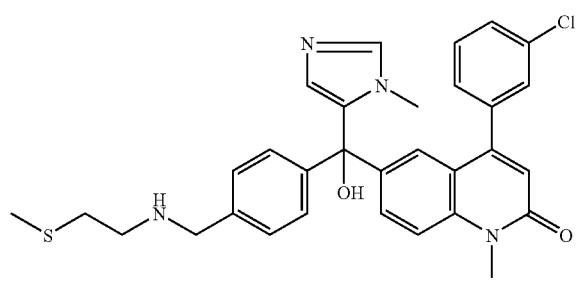
[B37] MS 559, 561
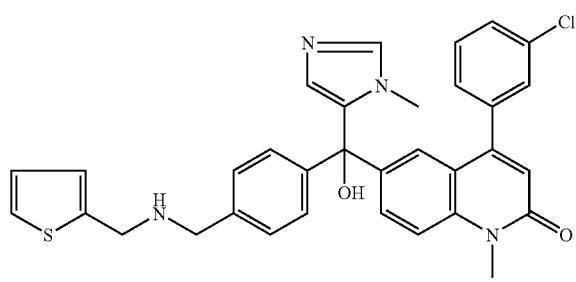
[B37] MS 581, 583
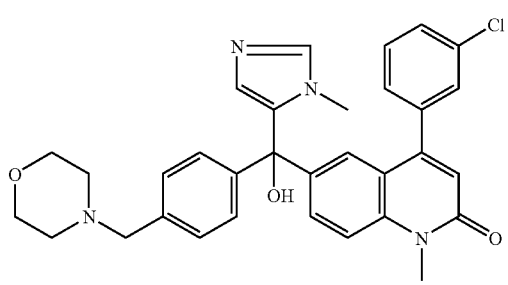
[B37] MS 555, 557
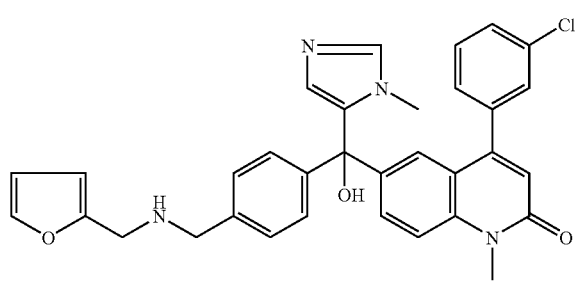
[B37] MS 565, 567

-continued
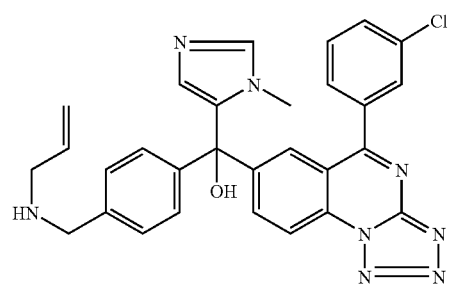
[B11] MS 537, 539
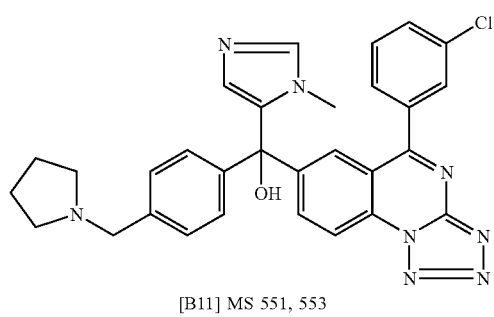
[B11] MS 551, 553
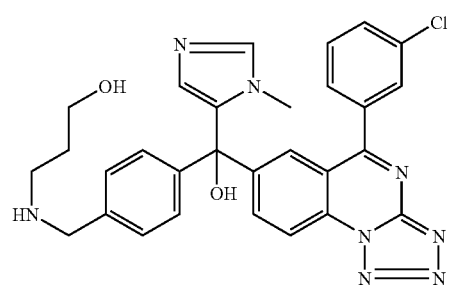
[B11] MS 555, 557
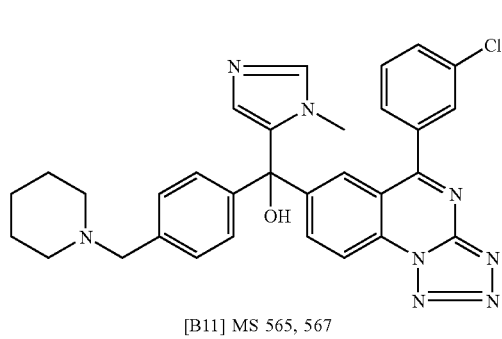
[B11] MS 565, 567
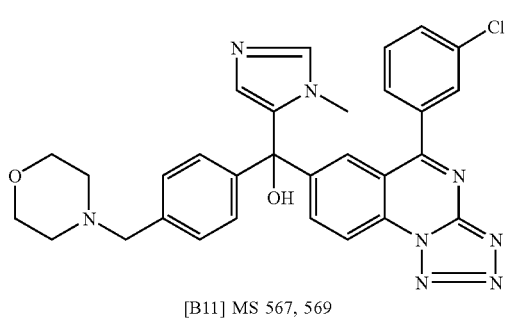
[B11] MS 567, 569

-continued
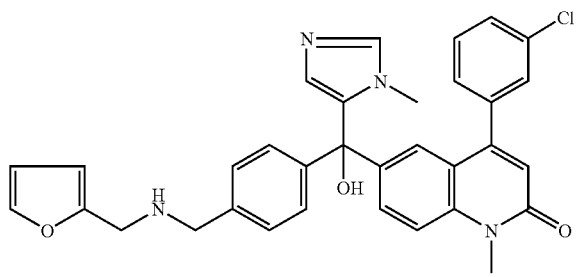
[B11] MS 574, 576
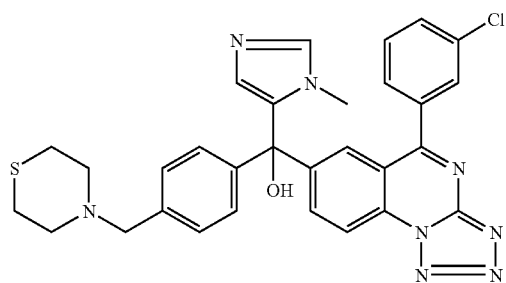
[B11] MS 583, 585
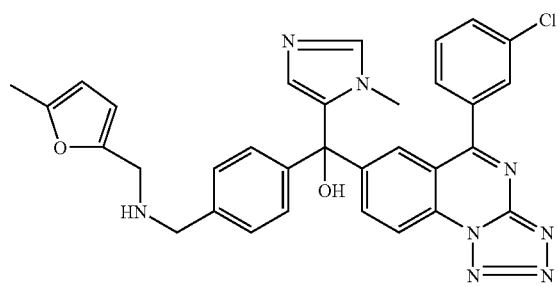
[B11] MS 591, 593
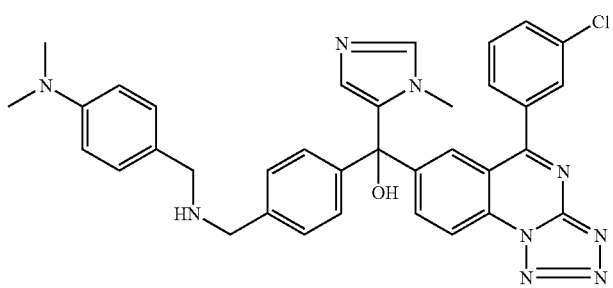
[B11] MS 630, 632
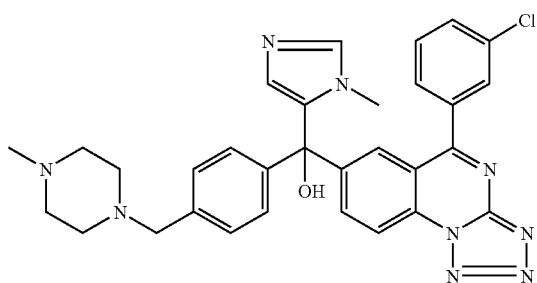
[B11] MS 580, 582

-continued

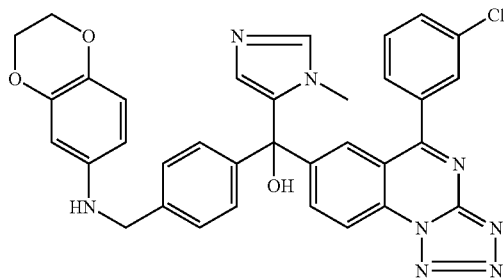

[B11] MS 631, 633

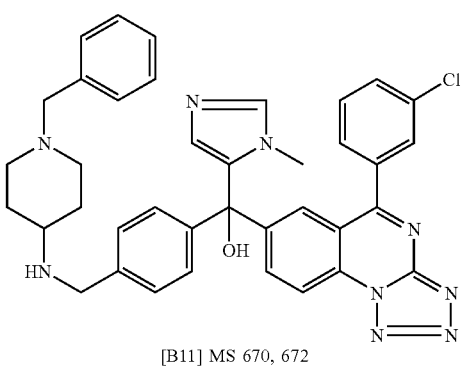

[B11] MS 670, 672

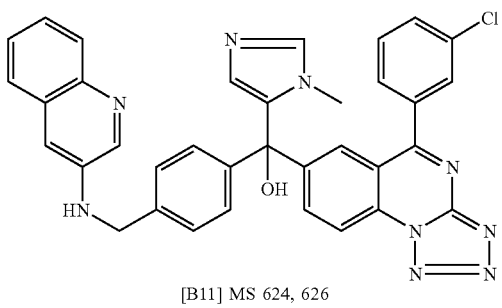

[B11] MS 624, 626

C. Pharmacological Examples.

EXAMPLE C.1

In Vitro Assay for Inhibition of Farnesyl Protein Transferase

An in vitro assay for inhibition of farnesyl transferase was performed essentially as described in WO 98/40383, pages 33–34.

EXAMPLE C.2

Ras-Transformed Cell Phenotype Reversion Assay

The ras-transformed cell phenotype reversion assay was performed essentially as described in WO 98/40383, pages 34–36.

EXAMPLE C.3

Farnesyl Protein Transferase Inhibitor Secondary Tumor Model

The farnesyl protein transferase inhibitor secondary tumor model was used as described in WO 98/40383, page 37.

D. Composition Example: Film-Coated Tablets

Preparatin of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I):

or a pharmaceutically acceptable salt or N-oxide or stereochemically isomeric form thereof, wherein
r and s are each independently 0, 1 or 2;
t is 0 or 1;
$>Y^1-Y^2-$ is a trivalent radical of formula $$>C=N- \quad (y\text{-}1);$$

$R^1$ is halo, $C_{1-6}$alkyl, $-(CR^{20}R^{21})_p-C_{3-10}$cycloalkyl, trihalomethyl, $C_{1-6}$alkyloxy, hydroxy$C_{1-6}$alkyloxy, trihalomethoxy, $C_{1-6}$alkylthio, $C_{2-6}$alkenyl, hydroxycarbonyl$C_{2-6}$alkenyl, $C_{2-6}$alkynyl, hydroxycarbonyl, $C_{1-6}$alkyloxycarbonyl, $-CONR^{22}R^{23}$, $-CH=N-OR^{25}$; or
two $R^1$ substituents adjacent to one another on the phenyl ring may form together a bivalent radical of formula $$-O-CH_2-O- \quad (a\text{-}1)$$

or $$-O-CH_2-CH_2-O- \quad (a\text{-}2);$$

p is 0 to 5;
$R^{20}$ and $R^{21}$ are independently hydrogen or $C_{1-6}$ alkyl and are independently defined for each iteration of p in excess of 1;
$R^{22}$ and $R^{23}$ are independently hydrogen, $C_{1-6}$ alkyl or $-(CR^{20}R^{21})_p-C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, $OCF_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;
$R^2$ is nitro, cyano$C_{1-6}$alkyl, hydroxy$C_{1-6}$alkyl, $C_{1-6}$alkyloxy$C_{1-6}$alkyl, $Het^2C_{1-6}$alkyl (in which the $C_{1-6}$alkyl moiety is optionally substituted by hydroxy), $Het^2SC_{1-6}$alkyl,
$-C_{1-6}$alkyl$NR_{22}$-$Het^2$, $-C_{1-6}$alkyl$NR^{22}$-$C_{1-6}$alkyloxy$C_{1-6}$alkyl, $-C_{1-6}$alkyl$NR^{22}$-$C_{1-6}$alkyl-$S-C_{1-6}$alkyl-$Ar^2$, $-C_{1-6}$alkyl$NR^{22}$-$C_{1-6}$alkyl-$S-C_{1-6}$alkyl, $-C_{1-6}$alkyl$NR^{22}$-$C_{1-6}$alkyl (in which the terminal $C_{1-6}$alkyl moiety is substituted by hydroxy), $-C_{1-6}$alkyl$NR^{22}C_{2-6}$alkenyl, $-C_{1-6}$alkyl$NR^{22}C_{1-6}$alkyl-$NR^{22}R^{23}$, $-C_{1-6}$alkyl$NR_{22}C_{1-6}$alkyl-$Ar^2$ (in which the $C_{1-6}$alkyl moiety adjacent to the $Ar^2$ is optionally substituted by $C_{1-6}$alkyloxycarbonyl), $-C_{1-6}$alkyl$NR^{22}C_{1-6}$alkyl-$Het^2$. $-C_{1-6}$alkyl$NR^{22}C_{1-6}$alkylC(O)O$C_{1-6}$alkyl, $-CHO$, $-CONR^{22}-C_{1-6}$alkyl-$Het^2$, $-CONR_{22}-C_{1-6}$alkyl-$Ar^2$, $-CONR^{22}-O-C_{1-6}$alkyl, $-CONR^{22}-C_{1-6}$alkenyl, $-CR^{24}=N-OR^{25}$ or halo, cyano, $C_{1-6}$alkyl or $C_{1-6}$alkyloxy;
and when $R^7$ below represents oxygen or sulphur, then $R^2$ may additionally represent—hydroxycarbonyl, $C_{1-6}$alkyloxycarbonyl, $-CONR^{22}R^{23}$, $R^{24}$ and $R^{25}$ are independently hydrogen, $C_{1-6}$alkyl, $-(CR_{20}R_{21})p$-$C_{3-10}$ cycloalkyl or aryl$C_{1-6}$alkyl;
$R^3$ is hydrogen, $C_{1-6}$alkyl, $-(CR^{20}R^{21})_p-C_{3-10}$cycloalkyl, halo$C_{1-6}$alkyl, cyano$C_{1-6}$alkyl, hydroxy$C^{1-6}$alkyl, $C_{1-6}$alkyloxy$C_{1-6}$alkyl, $-C^{1-6}$alkyl-$NR^{22}R^{23}$, $Het^2C_{1-6}$alkyl, $-C_{2-6}$alkenyl $NR^{22}R^{23}$, or $Het^2$; or
a radical of formula $$-O-R^{10} \quad (b\text{-}1)$$

or $$-NR^{11}R^{12} \quad (b\text{-}3)$$

wherein $R^{10}$ is hydrogen, $C_{1-6}$alkyl, $-(CR^{20}R^{21})_p-C_{3-10}$ cycloalkyl, or a radical of formula -Alk-$OR^{13}$ or -Alk-$NR^{14}R^{15}$;
$R^{11}$ is hydrogen or $C_{1-6}$alkyl; $R^{12}$ is hydrogen, hydroxy, $C_{1-6}$alkyl, $-(CR^{20}R^{21})_p-C_{3-10}$cycloalkyl, $C_{1-6}$alkyloxy, $C_{1-6}$alkylcarbonyl, aryl$C_{1-6}$alkylcarbonyl, $Het^2C_{1-6}$alkylcarbonyl, aminocarbonyl, mono- or di($C_{1-6}$alkyl)amino$C_{1-6}$alkylcarbonyl, or a radical of formula -Alk-$OR^{13}$ or Alk-$NR^{14}R^{15}$;
wherein Alk is $C_{1-6}$alkanediyl;
$R^{13}$ is hydrogen, $C_{1-6}$alkyl or $-(CR^{20}R^{21})_p-C_{3-10}$cycloalkyl; $R^{14}$ is hydrogen, $C_{1-6}$alkyl or $-(CR^{20}R^{21})_p-C_{3-10}$cycloalkyl; $R^{15}$ is hydrogen or $C_{1-6}$alkyl;
$R^4$ is a radical of formula wherein $R^{18}$ is hydrogen, $C_{1-6}$alkyl or $-(CR^{20}R^{21})_p-C_{3-10}$cycloalkyl; $R^{15a}$ is hydrogen;
$R^5$ is cyano, halo, $C_{1-6}$alkyl, $C_{2-6}$alkynyl, $C_{1-6}$alkyloxy or $C_{1-6}$alkyloxycarbonyl;
$R^8$ is hydrogen, $C_{1-6}$alkyl, $-(CR^{20}R^{21})_p-C_{3-10}$cycloalkyl, $-C_{1-6}$alkyl$CO_2R^{24}$, aminocarbonyl$C_{1-6}$alkyl -Alk-$Ar^2$ or Alk$Het^2$;
$R^7$ is oxygen or sulphur; or $R^6$ and $R^7$ together form a trivalent radical of formula:

$$-CR^{30}=CR^{31}-N= \quad (x\text{-}1)$$

$$-CR^{30}=N-N= \quad (x\text{-}2)$$

$$-C(=O)-NH-N= \quad (x\text{-}3)$$

$$-N=N-N= \quad (x\text{-}4)$$

or $$-N=N-CR^{30}= \quad (x\text{-}9)$$

wherein each $R^{30}$ and $R^{31}$ are independently hydrogen, $C_{1-6}$alkyl, $-OR^{24}$, $-CHO$, $-COOR^{24}$, $-NR^{22}R^{23}$,

119

—$C_{1-6}$alkylOR$^{24}$, —$C_{1-6}$alkylSR$^{24}$, R$^{23}$R$^{22}$NC$_{1-6}$ alkyl-, CONR$^{22}$R$^{23}$, $C_{2-6}$alkenyl, $C_{2-6}$alkenylAr$^2$, $C_{2-6}$alkenylHet$^2$, cyano, amino, thio, $C_{1-6}$alkylthio, —O—Ar$^2$, —S—Ar$^2$, Ar$^2$, Het$^2$ or $C_{1-6}$alkylHet$^2$;

Ar$^2$ is phenyl, naphthyl or phenyl or naphthyl substituted by one to five substituents each independently selected from halo, hydroxy, cyano, nitro, $C_{1-6}$alkyl, haloC$_{1-6}$alkyl, -alkylNR$^{22}$R$^{23}$, $C_{1-6}$alkyloxy, OCF$_3$, hydroxycarbonyl, $C_{1-6}$alkyloxycarbonyl, aryloxy, —NR$^{22}$R$^{23}$, $C_{1-6}$alkylsulfonylamino, oxime or phenyl, or a bivalent substituent of formula —O—CH$_2$—O— or —O—CH$_2$—CH$_2$—O—;

Het$^2$ is a 5- or 6-membered monocyclic heterocyclic ring containing one, two or three heteroatoms selected from oxygen, sulphur or nitrogen, or a 9- or 10-membered bicyclic heterocyclic ring and optionally substituted by one or two substituents each independently selected from halo, hydroxy, cyano, nitro, $C_{1-6}$alkyl, haloC$_{1-6}$alkyl, -alkylNR$^{22}$R$^{23}$, $C_{1-6}$alkyloxy, OCF$_3$, hydroxycarbonyl, $C_{1-6}$alkyloxycarbonyl, —CONR$^{22}$R$^{23}$, —NR$^{22}$R$^{23}$, $C_{1-6}$alkylsulfonylamino, oxime or phenyl;

provided that when R$^1$ is a group of formula —CH=NOR$^{25}$, or $C_{2-6}$alkynyl and/or R$^3$ is a triazolyl group optionally substituted as defined for Het$^2$ and/or R$^6$ is —(CR$^{20}$R$^{21}$)$_p$—C$_{3-10}$cycloalkyl, then R$^6$ and R$^7$ together form a trivalent radical selected from formulae (x-1), (x-2), (x-3), (x-4) or (x-9).

2. A compound according to claim 1 in which:

r is 0, 1 or 2;

s is 0 or 1;

t is 0;

R$^1$ is halo, $C_{1-6}$alkyl, $C_{2-6}$alkenyl, $C_{2-6}$alkynyl or two R$^1$ substituents ortho to one another on the phenyl ring may independently form together a bivalent radical of formula (a-1);

R$^2$ is nitro, cyano, halo, $C_{1-6}$alkyl, cyanoC$_{1-6}$alkyl, hydroxyC$_{1-6}$alkyl, $C_{1-6}$alkyloxyC$_{1-6}$alkyl, Het$^2$C$_{1-6}$alkyl (in which the $C_{1-6}$alkyl moiety is optionally substituted by hydroxy), Het$^2$SC$_{1-6}$alkyl, —C$_{1-6}$alkylNR$^{22}$-Het$^2$, —C$_{1-6}$alkylNR$^{22}$—C$_{1-6}$alkyloxyC$_{1-6}$alkyl, —C$_{1-6}$alkylNR$^{22}$—C$_{1-6}$alkyl-S—C$_{1-6}$alkyl-Ar$^2$, —C$_{1-6}$alkylNR$^{22}$—C$_{1-6}$alkyl (in which the terminal $C_{1-6}$alkyl moiety is substituted by hydroxy), —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{1-6}$alkyl-Ar$^2$ (in which the $C_{1-6}$alkyl moiety adjacent to the Ar$^2$ is optionally substituted by $C_{1-6}$alkyloxycarbonyl), —C$_{1-6}$alkylNR$^{22}$C$_{1-6}$alkyl-Het$^2$, —C$_{1-6\ alkylNR}$$^{22}$C$_{1-6}$alkylC(O)OC$_{1-6}$alkyl, —CHO, hydroxycarbonyl, C$_{1-6}$alkyloxycarbonyl, —CONR$^{22}$R$^{23}$, —CONR$^{22}$—C$_{1-6}$alkyl-Het$^2$, —CONR$^{22}$—C$_{1-6}$alkyl-Ar$^2$, —CONR$^{22}$—O—C$_{1-6}$alkyl, —CONR$^{22}$—C$_{1-6}$alkenyl, or —CR$^{24}$=N—OR$^{25}$, in which the above Het$^2$ groups are independently selected from 5- or 6-membered monocyclic heterocyclic rings;

R$^3$ is Het$^2$ or a group of formula (b-1) or (b-3) wherein R$^{10}$ is hydrogen or a group of formula -Alk-OR$^{13}$;

R$^{11}$ is hydrogen;

R$^{12}$ is hydrogen, $C_{1-6}$alkyl, $C_{1-6}$alkylcarbonyl, hydroxy, $C_{1-6}$alkyloxy or mono- or di($C_{1-6}$alkyl)aminoC$_{1-6}$alkylcarbonyl;

Alk is $C_{1-6}$alkanediyl and R$^{13}$ is hydrogen;

R$^4$ is a group of formula (c-3) wherein

R$^{18}$ is hydrogen or $C_{1-6}$alkyl;

R$^{18a}$ is hydrogen;

120

R$^6$ is (CR$^{20}$R$^{21}$)$_p$—$C_{3-10}$cycloalkyl, —$C_{1-6}$alkylCO$_2$R$^{24}$, aminocarbonylC$_{1-6}$alkyl, -Alk-Ar$^2$ or -AlkHet$^2$ or $C_{1-6}$alkyl;

R$^7$ is oxygen; or R$^6$ and R$^7$ together form a trivalent radical of formula (x-1), (x-2), (x-3), (x-4) or (x-9); and aryl is phenyl.

3. A compound according to claim 1 in which:

r is 0 or 1, s is 1, t is 0, R$^1$ is halo, C$_{(1-4)}$alkyl or forms a bivalent radical of formula (a-1), R$^2$ is nitro, cyano, halo, $C_{1-6}$alkyl, cyanoC$_4$alkyl, $C_{1-6}$alkyloxyC$_{1-6}$alkyl, Het$^2$C$_{1-6}$alkyl (in which the $C_{1-6}$alkyl moiety is optionally substituted by hydroxy), Het$^2$SC$_{1-6}$alkyl, —C$_{1-6}$alkyl NR$^{22}$—C$_{1-6}$alkyl-S—C$_{1-6}$alkyl, —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{1-6}$alkyl-Ar$^2$, —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl, —CHO, CH$_2$OH or —CR$^{24}$=N—OR$^{25}$ in which R$^{24}$ is hydrogen and R$^{25}$ is hydrogen or a methyl group; R$^3$ is hydrogen or a radical of formula (b-1) or (b-3), R$^{10}$ is hydrogen or -Alk-OR$^{13}$, R$^{11}$ is hydrogen and R$^{12}$ is hydrogen or $C_{1-6}$alkylcarbonyl and R$^{13}$ is hydrogen; R$^4$ is a radical of formula (c-3), wherein R$^{18}$ is $C_{1-6}$alkyl, R$^{18a}$ is hydrogen;

R$^6$ is $C_{1-6}$alkyl, —CH$_2$—$C_{3-10}$cycloalkyl, —C$_{1-6}$alkylCO$_2$R$^{24}$(R$^{24}$=H,Et), aminocarbonylC$_{1-6}$alkyl, -Alk-Ar$^2$ or -AlkHet$^2$;

R$^7$ is oxygen; or R$^6$ and R$^7$ together form a trivalent radical of formula (x-2), (x-3), or (x-4).

4. A compound according to claim 1 in which:

r is 0 or 1, s is 1, t is 0, R$^1$ is halo, R$^2$ is nitro, cyano, halo C$_{1-6}$alkyl, cyanoC$_{1-6}$alkyl, $C_{1-6}$alkyloxyC$_{1-6}$alkyl, Het$^2$C$_{1-6}$alkyl (in which the $C_{1-6}$alkyl moiety is optionally substituted by hydroxy), Het$^2$SC$_{1-6}$alkyl, —C$_{1-6}$alkylNR$^{22}$—C$_{1-6}$alkyl-S—C$_{1-6}$alkyl, —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{1-6}$alkyl-Ar$^2$, —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl, CHO, CH$_2$OH or —CR$^{24}$=N—OR$^{25}$ in which R$^{24}$ is hydrogen and R$^{25}$ is hydrogen or a methyl group; R$^3$ is hydrogen or a radical of formula (b-1) or (b-3), R$^{10}$ is hydrogen, R$^{11}$ is hydrogen and R$^{12}$ is hydrogen, R$^4$ is a radical of formula (c-3), wherein R$^{18}$ is $C_{1-6}$alkyl, R$^{18a}$ is hydrogen;

R$^6$ is $C_{1-6}$alkyl, —CH$_2$—$C_{3-10}$cycloalkyl or —$C_{1-6}$alkylAr$^2$;

R$^7$ is oxygen; or R$^6$ and R$^7$ together form a trivalent radical of formula (x-2) or (x-4).

5. A compound according to claim 1 in which:

r and s are 1, t is 0, R$^1$ is halo or $C_{1-4}$alkyl, R$^2$ is nitro, cyano, halo, $C_{1-6}$alkyl, cyanoC$_{1-6}$alkyl, $C_{1-6}$alkyloxyC$_{1-6}$alkyl, Het$^2$C$_{1-6}$alkyl in which Het$^2$ is 1-tetrazolyl, Het$^2$SC$_{1-6}$alkyl in which Het$^2$ is 2-thiazolyl, —C$_{1-6}$alkylNR$^{22}$—C$_{1-6}$alkyl-S—C$_{1-6}$alkyl, —C$_{1-6}$alkylNR$^{22}$C$_{2-6}$alkynyl, —C$_{1-6}$alkylNR$^{22}$C$_{1-6}$alkyl-NR$^{22}$R$^{23}$, —C$_{1-6}$alkylNR$^{22}$C$_{1-6}$alkyl-Ar$^2$, —C$_{1-6}$alkylNR$^{22}$C$_{1-6}$alkyl-Het$^2$, —C$_{1-6}$alkylNR$^{22}$C$_{1-6}$alkylC(O)OC$_{1-6}$alkyl, —CHO, CH$_2$OH or —CR$^{24}$=N—OR$^{25}$ in which R$^{24}$ is hydrogen and R$^{25}$ is hydrogen or a methyl group; R$^3$ is a radical of formula (b-1) or (b-3), R$^{10}$ and R$^{11}$ are hydrogen and R$^{12}$ is hydrogen or hydroxy, R$^4$ is a radical of formula (c-3), wherein R$^{18}$ is $C_{1-6}$alkyl , R$^{18a}$ is hydrogen;

R$^6$ is $C_{1-6}$alkyl, —CH$_2$—$C_{3-10}$cycloalkyl or -alkylAr$^2$; R$^7$ is oxygen; or R$^6$ and R$^7$ together form a trivalent radical of formula (x-4).

6. A compound according to claim 1 selected from:
4-[[5-(3-chlorophenyl)tetrazolo[1,5-a]quinazolin-7-yl](4-methyl-4H-1,2,4-triazol-3-yl)methyl]-benzonitrile,
5-(3-chlorophenyl)-α-(4-chlorophenyl)-α-(4methyl-4H-1,2,4-triazol-3-yl)-tetrazolo[1,5-a]quinazoline-7-methanamine,
4-[amino[5-(3-chlorophenyl)tetrazolo[1,5-a]quinazolin-7-yl](4-methyl-4H-1,2,4-triazol-3-yl)methyl]-benzonitrile, and their pharmaceutically acceptable salts.

7. A method for treating colon and pancreatic cancers comprising administering an effective amount of a compound according to claim 1 to a subject in need of such treatment.

8. A method of treating colon and pancreatic cancers in a subject in need thereof which comprises administering an effective amount of a compound as claimed in claim 1 to the subject in combination with administration of irradiation.

* * * * *